(12) United States Patent
Dixon et al.

(10) Patent No.: US 8,420,889 B2
(45) Date of Patent: Apr. 16, 2013

(54) EPICATECHIN GLUCOSYLTRANSFERASE

(75) Inventors: Richard A. Dixon, Ardmore, OK (US);
Yongzhen Pang, Ardmore, OK (US);
Gregory J. Peel, Sacramento, CA (US)

(73) Assignee: The Samuel Roberts Noble Foundation, Ardmore, OK (US)

( * ) Notice: Subject to any disclaimer, the term of this patent is extended or adjusted under 35 U.S.C. 154(b) by 470 days.

(21) Appl. No.: 12/549,248

(22) Filed: Aug. 27, 2009

(65) Prior Publication Data
US 2010/0064387 A1 Mar. 11, 2010

Related U.S. Application Data

(60) Provisional application No. 61/093,006, filed on Aug. 29, 2008.

(51) Int. Cl.
*A01H 5/00* (2006.01)
*C12N 15/52* (2006.01)
*C12N 15/85* (2006.01)
*C12N 9/10* (2006.01)

(52) U.S. Cl.
USPC .......... 800/284; 800/298; 800/282; 536/23.2; 530/370; 435/91.1; 435/468; 435/419; 435/320.1

(58) Field of Classification Search ........................ None
See application file for complete search history.

(56) References Cited

U.S. PATENT DOCUMENTS

| | | | | |
|---|---|---|---|---|
| 7,709,701 | B2 | 5/2010 | Dixon et al. | 800/295 |
| 2005/0233346 | A1* | 10/2005 | Dixon et al. | 435/6 |
| 2009/0083874 | A1 | 3/2009 | Dixon et al. | 800/282 |

FOREIGN PATENT DOCUMENTS

WO  WO 2006/010096  1/2006

OTHER PUBLICATIONS

Guo et al., 2004, Protein tolerance to random amino acid change, PNAS 101(25):9205-9210.*
Pang et al, A transcript profiling approach reveals an epicatechin-specific glycosyltransferas expressed in the seed coat of *Medicago truncatula*, 2008, PNAS 105:14210-14215.*
Modolo et al., "A functional genomics approach to (iso)flavonoid glycosylation in the model legume *Medicago truncatula*," *Plant Mol. Biol.*, 64:499-518, 2007.
Pang et al., "Early steps in proanthocyanidin biosynthesis in the model legume *Medicago truncatula*," *Plant Physiol.*, 145:601-615, 2007.
Aziz et at, "Transcriptome analysis of alfalfa glandular trichomes," *Planta*, 221:28-38, 2005.
Baudry et al., "TT2, TT8 and TTG1 synergistically specify the expression of BANYULS and proanthocyanidin biosynthesis in *Arabidopsis thaliana*," *The Plant J.*, 39:366:380, 2004.
Baxter et al., "A plasma membrane H+-ATPase is required for the formation of proanthocyanidins in the seed coat endothelium of *Arabidopsis thaliana*," *PNAS*, 102(7):2649-2654, 2005.
Benedito et al., "A gene expression atlas of the model legume *Medicago truncatula*," *The Plant J.*, 55:504-513, 2008.
Borevitz et al., "Activation tagging identifies a conserved MYB regulator of phenylpropanoid biosynthesis," *The Plant Cell*, 12:2383-2393, 2000.
Brazier-Hicks et al., "Characterization and engineering of the bifunctional N- and O- glucosyltransferase involved in xenobiotic metabolism in plants," *PNAS*, 104(51):20238-20243, 2007.
Broderick, "Desirable characteristics of forage legumes for improving protein utilization in ruminants," *J. Anim. Sci.*, 73:2760-2773, 1995.
Database EMBL Accession No. AC1249766, dated Jun. 21, 2002.
Deavours et al., "Metabolic engineering of isoflavonoid biosynthesis in alfalfa," *Plant Physiology*, 138:2245-2259, 2005.
Debeaujon et al., "The transparent TESTA12 gene of *Arabidopsis* encodes a multidrug secondary transporter-like protein required for flavonoid sequestration in vacules of the seed coat endothelium," *The Plant Cell*, 13:853-871, 2001.
di Guan et al., "Vectors that facilitate the expression and purification of foreign peptides in *Escherichia coli* by fusion to maltose-binding protein," *Gene*, 67:21-30, 1988.
GenBank Accession No. AAK53551, dated Dec. 16, 2005.
GenBank Accession No. AAL92460, dated Dec. 16, 2005.
GenBank Accession No. AAW56092, dated Mar. 7, 2005.
GenBank Accession No. AB194020, dated Dec. 12, 2007.
GenBank Accession No. AB194021, dated Dec. 12, 2007.
GenBank Accession No. AB194022, dated Dec. 12, 2007.
GenBank Accession No. AB194023, dated Dec. 12, 2007.
GenBank Accession No. AB194024, dated Dec. 12, 2007.
GenBank Accession No. AB194025, dated Dec. 12, 2007.
GenBank Accession No. AF190298, dated Jan. 25, 2002.
GenBank Accession No. AJ133743, dated Nov. 14, 2006.
GenBank Accession No. AJ277509, dated Nov. 2, 2000.
GenBank Accession No. AJ294464, dated Apr. 30, 2001.
GenBank Accession No. AJ299452, dated Nov. 14, 2006.
GenBank Accession No. CAC35167, dated Mar. 29, 2001.
GenBank Accession No. DQ875465, dated Jul. 2, 2007.
GenBank Accession No. EU434684, dated Sep. 23, 2008.
Grotewold, "The challenges of moving chemicals within and out of cells: insights into the transport of plant natural products," *Planta*, 219:906-909, 2004.
Kitamura et al., "Transparent TESTA 19 is involved in the accumulation of both anthocyanins and proanthocyanidins in arabidopsis," *The Plant J.*, 37:104-114, 2004.

(Continued)

*Primary Examiner* — Brent T Page
*Assistant Examiner* — Lee A Visone
(74) *Attorney, Agent, or Firm* — SNR Denton US LLP

(57) ABSTRACT

The invention provides methods and compositions for the modulation of epicatechin glucosyltransferase activity in plants. Increased expression of epicatechin glucosides, and ultimately anthocyanins and proanthocyanidins, in plants may be used to increase the nutritional value of food plants for both human and animal consumption. Increased proanthocyanidin content also reduces the potential for bloat in animals fed certain forage plants low in condensed tannin content.

39 Claims, 22 Drawing Sheets

OTHER PUBLICATIONS

Lees, "Condensed tannins in some forage legumes: Their role in the prevention of ruminant pasture bloat," In: Plant Polyphenols Basic Life Science, Hemingway eds., Plenum Press, pp. 915-934, 1992.

Lepiniec et al., "Genetics and biochemistry of seed flavonoids," *Ann. Rev. Plant Biol.*, 57:405-530, 2006.

Liu et al., "Resistance to the macrolide antibiotic tylosin is conferred by single methylations at 23S rRNA nucleotides G748 and A2058 acting in synergy," *PNAS*, 99(23):14658-14663, 2002.

Mueller et al., "AN9, a petunia glutathione S-transferase required for anthocyanin sequestration, is a flavonoid-binding protein," *Plant Physiology*, 123:1561-1570, 2000.

NCBI Accession No. NP_192016, dated Aug. 21, 2009.

Nesi et al., "The arabidopsis TT2 gene encodes an R2R3 MYB domain protein that acts as a key determinant for proanthocyanidin accumulation in developing seed," *The Plant Cell*, 13:2099-2114, 2001.

Nesi et al., "The TT8 gene encodes a basic helix-loop-helix domain protein required for expression of DFR and BAN genes in Arabidopsis siliques," *The Plant Cell*, 12:1863-1878, 2000.

Pang et al., "A transcript profiling approach reveals an epicatechin-specific glucosyltransferase expressed in the seed coat of *Medicago truncatula*,"*PNAS*, 105(37):14210-14215, 2008.

Peel et al., "Detection and quantification of engineered proanthocyandins in transgenic plants," *Natural Product Communications*, 2(10):1009-1014, 2007.

Sharma et al., "Metabolic engineering of proanthocyanidins by ectopic expression of transcription factors in *Arabidopsis thaliana*," *The Plant J.*, 44:62-75, 2005.

Shimoda et al., "Glycosylation and malonylation of quercetin, epicatechin, and catechin by cultured plant cells," *Chemistry Letters*, 36(10):1292-1293, 2007.

Snyder et al., "Synthesis of phytoalexins in *Sorghum* as a site-specific response to fungal ingress," *Science*, 248:1637-1639, 1990.

Zhang et al., "A network of redundant bHLH proteins functions in all TTG1-dependent pathways of *Arabidopsis*," *Development*, 130:4859-4869, 2003.

\* cited by examiner

FIG. 11A

```
                170        180        190        200        210        220        230        240
GT22D    FNMHNFHVNN -MAEIMANK- ---------ES EYFELPGIPD KIEMTIAQTG LGGLKGEVWK QFNDDLLEAE IGSYGMLVNS
GT99D    SAMNSIEQFE PHAKVKSNS- ---------VS -FLLPGLPH NVEMTRLQLP DWLRAPNGYT YLMKMIKDSE KKSYGSLFDS
UGT72L1  AWSFYLPKLD EETTCEYRD- ---------LP EPIKVPGCVP LHGRDLLTI- VQDRSSQAYK YFLQHVKSLS F-ADGVLVNS
RsAS     SLFFHLPKLD QMVSCEYRD- ---------VP EPLQIPGCIP IHGKDFLDP- AQDRKNDAYK CLLHQAKRYR L-AEGIMVNT
GT22E09  CLFLNFPTFH KNATIPIKDY ---------NMH TPIELPGLPR LSKEDYPDE- GKDPSSPSYQ VLLQSAKSLR E-SDGIIVNT
GT29C    AVFLQLPTIH QSTTKSLKEF ---------HMY P-RIPGLPL VPIVDMPDE- VKDRESKSYK VFLDMATSMR E-SDGVIINT
UGT71G1  SLMLSLKNRQ IEEVFDDSD- ---------RDH QLNIPGISN QVPSNVLPD- ACFNKDGGYI AYYKLAERFR D-TKGIIVNT
GT63G    TICYDYHKL LPFPSNEEP- ---------Y IDVQLNSSIV LKYNEIPDFI HPFCRYPILG TLTTAQIKDM SKVFCVLVDT
GT67A    LNMHFRSFV ERGIIPFKDE SYLTNGCLET KVDWIPGLKN FRLKDIVDFI RTTNPNDIML EFFIEVADRV NKDTTILLNT
GT83F    LTHVYTDLIR EKTGSKEVHD ---------VK SIDVLPGFPE LKASDLPEGV IKDIDVPFAT MLHKMGLELP R-ANAVAINS 250        260        270        280        290        300        310        320
GT22D    FEELEPTYAR DYKKVRNDKV WCIGPVSLS- NTDYLDKVQR GNNNNKVSND EWEHLKWLDS HKQGSVIYAC FGSLCN-LTP
GT99D    YYEIEGTYED YYKIAWGSKS WSVGPVSLWM NKDDSDKAGR G-HGKEEDE EEGVLKWLDS KKYDSVLYVS FGSMNK-FPT
UGT72L1  FLEME--MG PINALTE--- -EGSGNPSVY PVGPIIQTVT GS-VDDAN GLECLSWLDK QQSCSVLYVS FGSGGT-LSH
RsAS     FNDLE--PG PLKALQE--- -EDQGKPPVY PIGPLIRADS SSK--VDDC- --ECLKWLDD QPRGSVLFIS FGSGGA-VSH
GT22E09  FDAIE---KK AIKALRNGLC VPDGTPLLF CIGPVVSTSC E-----EDKS G--CLSWLDS QPGQSVVLLS FGSLGR-FSK
GT29C    FDAIE---GR AAKALKAGLC LPEGTTPPLF CIGPMISPPC KG---EDER GSSCLSWLDS QPSQSVVLLS FGSMGR-FSR
UGT71G1  FSDLE---QS SIDALYD--- -HDEKIPPIY AVGPLLDLKG QPNPKLDQAQ HDLILKWLDE QPDKSVVFLC FGSMGVSFGP
GT63G    FEELE---HD FIDYISEKSI AIRPVGPLFK NPKANGASWN ILGDFTKSND DCNITEWLNT KPKGSVVYIS FGTVVY-LPQ
GT67A    FNELESDVIN ALSSTIPSIY PIGPLPSLLK QTPQIHQLDS LDSN-LWKE DTECLDWLES KEPGSVVYVN FGSITV-MTP
GT83F    FATIHPLIEN ELN------- ----SKFKLLL NVGPFNLTTP QR-----KVSD EHGCLEWLDQ HENSSVVYIS FGSVVT-PPP
```

FIG. 11B

```
                330        340        350        360        370        380        390        400
GT22D     PQLIELGLAL EATKRPFIWV LREGNQLE-- ---------- -------E LKKWLEESGF EGRINGR--G -LVIKGWAPQ LLILSHLAIG
GT99D     PQLVEIAHAL EDSGHDFIWV VRKIEDAE-- ---------- -------D GDDGF-LSEF EKRMKERNKG -YLIWGWAPQ LLILEHGAVG
UGT72L1   EQIVELALGL ELSNQKFLWV VRAPSSSSSN AAYLSAQNDV DALQFLPSGF LERTKEEG-- ---------- -FVITSWAPQ IQILSHSSVG
RsAS      NQFIELALGL EMSEQRFLWV VRSPNDKIAN ATYFSIQNQN DALAYLPEGF LERTKGRC-- ---------- -LLVPSWAPQ TEILSHGSTG
GT22E09   AQINQIAIGL EKSEQRFLWI VRSDMES--- ---------- -----EEL SLDELLPEGF LERTKEKG-- ---------- -MVVRNWAPQ GSILRHSSVG
GT29C     AQLNQIAIGL EKSEQRFLWV VRSEPDS--- ---------- -----DKL SLDELFPEGF LERTKDKG-- ---------- -MVVRNWAPQ VAILSHNSVG
UGT71G1   SQIRETALGL KHSGVRFLWS N--------- ---------- -------S AEKKVFPEGF LEWMELEG-- ---------- KGMICGWAPQ VEVLAHKAIG
GT63G     ELVYEIAYGL LDSQVTFLWA KKQHDD---- ---------- ---------- -------- -LPYGF LEETSGRG-- ---------- -KVVNWSPQ EQVLAHPSVA
GT67A     EQLLEFAWGL ANCKKSFLWI IRPDLVIG-- ---------- ---------- -------- -GSVIFSSEF TNEIADRG-- ---------- -LIASWCPQ DKVLNHPSIG
GT83F     HELTALAESL EECGFPFIWS FRGDPKEK-- ---------- ---------- -------- -LPKGF LERTKTKG-- ---------- -KIVAWAPQ VEILKHSSVG 410        420        430        440        450        460        470        480
GT22D     GFLTHCGWNS TLEAICAGVP MVTWPLFADQ FLNESFVVQI LKVGVKIGVK SPMKWGEEED GVLVKKEDIE RGIEKLMDET
GT99D     AVVTHCGWNT IMESVNAGLP LATWPLFAEQ FFNERLLVDV LKIGVAVGAK EWRMNNEFGD DV-VKREDIG KAIGLLMGGG
UGT72L1   GFLSHCGWNS TLESVVHGVP LITNPMFAEQ GMNAVLVTEG LKVGLRPRVN E--------- ---------- NGIVERVEVA KVIKRLM-EG
RsAS      GFLTHCGWNS ILESVVNGVP LIAWPLYAEQ KMNAVMLTEG LKVALRPKAG E--------- ---------- NGLIGRVEIA NAVKGLM-EG
GT22E09   VLEAICEGVP MITWPLYAEQ KMNRLILVQE MKVALELNES K--------- ---------- DGFVSENELG ERVKELM-ES
GT29C     GFVTHCGWNS VLEAICEGVP MIAWPLFAEQ RLNRLVLVDE MKVALKVNQS E--------- ---------- NRFVSGTELG ERVKELM-ES
UGT71G1   GFVSHCGWNS ILESMMFGVP ILTWPIYAEQ QLNAFRLVKE WGVGLGLRVD YRK------G SDVVAAEEIE KGLKDLM-DK
GT63G     CFITHCGWNS SMEALTLGVP MLTFPTFGDQ LTNAKFLVDV PTDCRFICNE WEIGMEIDTN VK-------- ---------- RKLVRRDDLK KCLLEVT-TG
GT67A     GFLTHCGWNS TTESICAGVP MLCWPFFADQ PTDCRFICNE WEIGMEIDTN VK-------- ---------- ------REELA KLINEVI-AG
GT83F     VFLTHSGWNS VLECIVGGVP MISRPFFGDQ GLNTILTESV LEIGVGDNG V--------- ---------- ---LTKESIK KALELTM-SS
```

FIG. 11C

```
             490        500        510        520        530
GT22D    SECKERRKRI RELAEMAKKA VEKGGSSHSN ISLFIQDIMK KNKDMMSSFI HGNANSK
GT99D    EECLEMRKRV KALSGAAKKA IEVGGSSYTK LKELIEELKS FKLEKINKKL VSVT---
UGT72L1  EECEKLHNNM KELKEVASNA LKEDGSSTKT ISQLTKMRN  LVQKNQI---
RsAS     EEGKKFRSTM KDLKOAASRA LSDDGSSTKA LAELACKMEN KISST---
GT22E09  EKGKEVRETI LKMKISAKEA RGGGGSSLVD LKKLGDSNRE HASMTSVSPN SPFLFA-
GT29C    DRGKDIKERI LKMKISAKEA RGGGGSSLVD LKKLGDSNRE HASMNSLSPN SPFLLR-
UGT71G1  D--SIVHKKV QEMKEMSRNA VVDGGSSLIS VGKLIDDITG SN---
GT63G    EKAETLKKNA TKLKKAAEEA VAVGGSSDRH LDAFMEDIKK HKRC---
GT67A    DKGKKWKQKA MELKKKAEEN TRPGGCSYMN LNKVIKDVLL KQN---
GT83F    EKGGIMRQKI VKLKESAFKA VEQNGTSAMD FTTLIQIVTS
```

EPICATECHIN GLUCOSYLTRANSFERASE

This application claims priority to U.S. Provisional Application No. 61/093,006, filed on Aug. 29, 2008, which is incorporated herein by reference in its entirety.

INCORPORATION-BY-REFERENCE OF SEQUENCE LISTING IN COMPUTER READABLE FORM

The Sequence Listing, which is a part of the present disclosure, includes a computer readable form 118 kb file entitled "NBLE063US_ST25.TXT" comprising nucleotide and/or amino acid sequences of the present invention submitted via EFS-Web. The subject matter of the Sequence Listing is incorporated herein by reference in its entirety.

FIELD OF THE INVENTION

The present invention generally relates to plant genetics. More specifically, the invention relates to genes and enzymes involved in the biosynthesis of anthocyanins, proanthocyanidins, and tannins, and methods for use thereof.

DESCRIPTION OF THE RELATED ART

Proanthocyanidins (PAs), also known as condensed tannins (CTs), are oligomeric/polymeric flavonoid compounds that provide protective functions in the fruits, bark, leaves and seeds of many plants. The building blocks of most PAs are (+)-catechin and (−)-epicatechin. (−)-Epicatechin has 2,3-cis stereochemistry and (+)-catechin has 2,3-trans-stereochemistry. The most common anthocyanidins produced are cyanidin (leading to procyanidins) and delphinidin (leading to prodelphinidins). PAs may contain from 2 to 50 or more flavonoid units. PA polymers have complex structures because of variations in the flavonoid units and the sites for interflavan bonds. Depending on their chemical structure and degree of polymerization, PAs may or may not be soluble in aqueous or organic solvents.

Realization of the beneficial qualities of PAs has increased the interest in these compounds. PAs benefit human health through their antioxidant, anticancer, anti-inflammatory and cardioprotective activities. The presence of PAs is also a positive trait in forage crops. PAs bind to proteins and slow their fermentation in the rumen, reducing generation of methane and thereby protecting the animal from potentially lethal pasture or feedlot bloat. Pasture bloat occurs in ruminants when they are fed with a high protein diet such as alfalfa (lucerne; *Medicago sativa*) or clover (*Trifolium* spp), species that lack PAs in their aerial portions. PAs also preserve proteins during the ensiling process, increasing the feed value of silage and reducing the amount of nitrogen that is lost to the environment as feedlot waste.

An attractive alternative for forage improvement lies in genetically transferring the capability to synthesize PAs to non PA-accumulators. However, relatively little is known of the proteins necessary for polymerization of tannins and their ultimate accumulation in vacuoles or cell walls. Even if anthocyanin production and downstream enzymes (for PA synthesis) are expressed, tannins have not necessarily accumulated. Thus, additional techniques for the production of novel plants with improved phenotypes, and methods for the use thereof, are needed. Such techniques may allow the creation and use of plants with improved nutritional quality, thereby benefiting both human and animal health and representing a substantial benefit in the art.

SUMMARY OF THE INVENTION

In one aspect, the invention provides an isolated nucleic acid sequence selected from the group consisting of: (a) a nucleic acid sequence encoding the polypeptide sequence of SEQ ID NO:1, or SEQ ID NO:3; (b) a nucleic acid sequence comprising a sequence selected from the group consisting of SEQ ID NO:2 and SEQ ID NO:4; (c) a nucleic acid sequence that hybridizes to SEQ ID NO:2 or SEQ ID NO:4, under conditions of 1×SSC, and 65° C. and encodes a polypeptide with epicatechin glucosylase activity; (d) a nucleic acid sequence encoding a polypeptide with at least 85% amino acid identity to SEQ ID NO:1 or SEQ ID NO:3, and encodes a polypeptide with epicatechin glucosylase activity; (e) a nucleic acid sequence with at least 85% identity to SEQ ID NO:2 or SEQ ID NO:4 and encodes a polypeptide with epicatechin glucosylase activity; and (f) a complement of a sequence of (a)-(e), wherein the nucleic acid sequence is operably linked to a heterologous promoter.

The invention further provides a recombinant vector comprising such an isolated nucleic acid sequence is provided. The recombinant vector may further comprise at least one additional sequence chosen from the group consisting of: a regulatory sequence, a sequence that encodes a polypeptide that activates anthocyanin or proanthocyanidin biosynthesis, a selectable marker, a leader sequence and a terminator. In particular embodiments, the polypeptide that activates anthocyanin or proanthocyanidin biosynthesis is selected from the group consisting of: phenylalanine ammonia-lyase (PAL), cinnamate 4-hydroxylase (C4H), 4-coumarate:CoA ligase (4CL), chalcone synthase (CHS), chalcone isomerase (CHI), flavanone 3-hydroxylase (F3H), dihydroflavonol reductase (DFR), anthocyanidin synthase (ANS), leucoanthocyanidin reductase (LAR), anthocyanidin reductase (ANR), a proanthocyanidin or anthocyanidin glucosyltransferase (GT), LAP1, LAP2, LAP3, LAP4, or AtPAP1 (production of anthocyanin pigment). The recombinant vector may further be defined as comprising a promoter, wherein the promoter is a plant developmentally-regulated, organelle-specific, inducible, tissue-specific, constitutive, or cell-specific promoter. The recombinant vector may, in certain embodiments, be defined as an isolated expression cassette.

Another aspect of the invention comprises an isolated polypeptide having at least 85% amino acid identity to the amino acid sequence of SEQ ID NO:1, or SEQ ID NO:3, or a fragment thereof, having epicatechin glucosyltransferase activity. In certain embodiments the isolated polypeptide may comprise the amino acid sequence of SEQ ID NO:1, or SEQ ID NO:3, or a fragment thereof, having epicatechin glucosyltransferase activity.

Yet another aspect of the invention comprises a transgenic plant transformed with a nucleic acid selected from the group consisting of: (a) a nucleic acid sequence encoding the polypeptide sequence of SEQ ID NO:1, or SEQ ID NO:3; (b) a nucleic acid sequence comprising a sequence selected from the group consisting of SEQ ID NO:2 and SEQ ID NO:4; (c) a nucleic acid sequence that hybridizes to SEQ ID NO:2 or SEQ ID NO:4, under conditions of 1×SSC, and 65° C. and encodes a polypeptide with epicatechin glucosylase activity; (d) a nucleic acid sequence encoding a polypeptide with at least 85% amino acid identity to SEQ ID NO:1 or SEQ ID NO:3, and encodes a polypeptide with epicatechin glucosylase activity; (e) a nucleic acid sequence with at least 85% identity to SEQ ID NO:2 or SEQ ID NO:4 and encodes a polypeptide with epicatechin glucosylase activity; and (f) a complement of a sequence of (a)-(e), wherein the nucleic acid sequence is operably linked to a heterologous promoter. Seed of such a plant, and progeny of such a plant of any subsequent generation, each comprising the selected DNA, are another aspect of the invention. In certain embodiments the invention provides such a transgenic plant, wherein the plant is a forage crop. In particular embodiments the plant is a legume. In more particular embodiments, the plant is a *Medicago* plant, such as an alfalfa plant. A plant that expresses the selected DNA and exhibits increased proanthocyanidin biosynthesis in selected tissues relative to those tissues in a second plant that differs from the transgenic plant only in that the selected DNA is absent is also provided.

The transgenic plant may further be defined, in certain embodiments, as one that is transformed with a selected DNA encoding an epicatechin glucosyltransferase polypeptide selected from the group consisting of SEQ ID NO:1, or SEQ ID NO:3, or a fragment thereof, having anthocyanin or proanthocyanidin biosynthesis activity. In other embodiments, the transgenic plant may further be defined as transformed with a selected DNA sequence complementary to a sequence encoding an epicatechin glucosyltransferase active in proanthocyanidin biosynthesis. In particular embodiments, the transgenic plant is further defined as transformed with a DNA sequence complementary to UGT72L1. In certain embodiments, the transgenic plant comprises the complement of SEQ ID NO:1 or SEQ ID NO:3, or a fragment thereof. In other embodiments, the transgenic plant is further defined as transformed with a DNA sequence encoding the polypeptide of SEQ ID NO:1. The invention also provides such a transgenic plant, wherein the plant is a forage legume. In particular embodiments, the plant is a *Medicago* plant. In particular embodiments, the plant is alfalfa (*Medicago sativa*).

In other embodiments, the transgenic plant is further defined as comprising a transgenic coding sequence encoding an anthocyanin reductase polypeptide selected from the group consisting of: SEQ ID NO:21 and SEQ ID NO:22.

In other embodiments, the transgenic plant comprising a nucleic acid selected from the group consisting of: (a) a nucleic acid sequence encoding the polypeptide sequence of SEQ ID NO:1, or SEQ ID NO:3; (b) a nucleic acid sequence comprising a sequence selected from the group consisting of SEQ ID NO:2 and SEQ ID NO:4; (c) a nucleic acid sequence that hybridizes to SEQ ID NO:2 or SEQ ID NO:4, under conditions of 1×SSC, and 65° C. and encodes a polypeptide with epicatechin glucosylase activity; (d) a nucleic acid sequence encoding a polypeptide with at least 85% amino acid identity to SEQ ID NO:1 or SEQ ID NO:3, and encodes a polypeptide with epicatechin glucosylase activity; (e) a nucleic acid sequence with at least 85% identity to SEQ ID NO:2 or SEQ ID NO:4 and encodes a polypeptide with epicatechin glucosylase activity; and (f) a complement of a sequence of (a)-(e), wherein the nucleic acid sequence is operably linked to a heterologous promoter, is further defined as comprising at least one additional transgenic coding sequence chosen from the group consisting of: a regulatory sequence, a sequence that encodes a polypeptide that activates anthocyanin or proanthocyanidin biosynthesis, a selectable marker, a leader sequence and a terminator.

In particular embodiments, the polypeptide that activates anthocyanin or proanthocyanidin biosynthesis is selected from the group consisting of: phenylalanine ammonia-lyase (PAL), cinnamate 4-hydroxylase (C4H), 4-coumarate:CoA ligase (4CL), chalcone synthase (CHS), chalcone isomerase (CHI), flavanone 3-hydroxylase (F3H), dihydroflavonol reductase (DFR), anthocyanidin synthase (ANS), leucoanthocyanidin reductase (LAR), anthocyanidin reductase (ANR), a proanthocyanidin or anthocyanidin glucosyltransferase (GT), LAP1, LAP2, LAP3, LAP4, or AtPAP1 (production of anthocyanin pigment). The transgenic plant may further be defined as a fertile $R_0$ transgenic plant, or as a progeny plant of any generation of a fertile $R_0$ transgenic plant, wherein the transgenic plant comprises the selected DNA.

In other embodiments, the transgenic plant is further defined as comprising a transgenic sequence that down-regulates UGT72L1 expression.

Also provided by the invention is a cell transformed with the nucleic acid of claim 1. In certain embodiments, the cell is a plant cell. In other embodiments, the cell is a bacterial cell.

The invention also provides a method of producing a plant with increased proanthocyanidin biosynthesis, comprising expressing in the plant an isolated nucleic acid sequence selected from the group consisting of: (a) a nucleic acid sequence encoding the polypeptide sequence of SEQ ID NO:1, or SEQ ID NO:3; (b) a nucleic acid sequence comprising a sequence selected from the group consisting of SEQ ID NO:2 and SEQ ID NO:4; (c) a nucleic acid sequence that hybridizes to SEQ ID NO:2 or SEQ ID NO:4, under conditions of 1×SSC, and 65° C. and encodes a polypeptide with epicatechin glucosylase activity; (d) a nucleic acid sequence encoding a polypeptide with at least 85% amino acid identity to SEQ ID NO:1 or SEQ ID NO:3, and encodes a polypeptide with epicatechin glucosylase activity; (e) a nucleic acid sequence with at least 85% identity to SEQ ID NO:2 or SEQ ID NO:4 and encodes a polypeptide with epicatechin glucosylase activity; and (f) a complement of a sequence of (a)-(e), wherein the nucleic acid sequence is operably linked to a heterologous promoter.

In some embodiments of the method the plant further comprises a recombinant vector, wherein the polypeptide that activates anthocyanin or proanthocyanidin biosynthesis is selected from the group consisting of: phenylalanine ammonia-lyase (PAL), cinnamate 4-hydroxylase (C4H), 4-coumarate:CoA ligase (4CL), chalcone synthase (CHS), chalcone isomerase (CHI), flavanone 3-hydroxylase (F3H), dihydroflavonol reductase (DFR), anthocyanidin synthase (ANS), leucoanthocyanidin reductase (LAR), anthocyanidin reductase (ANR), a proanthocyanidin or anthocyanidin glucosyltransferase (GT), LAP1, LAP2, LAP3, LAP4, or AtPAP1 (production of anthocyanin pigment). In certain embodiments, the nucleic acid sequence is introduced into the plant by plant breeding. In other embodiments, the nucleic acid sequence is introduced into the plant by genetic transformation of the plant. Further, in other embodiments the recombinant vector comprises a promoter which is a constitutive or tissue specific promoter. In some embodiments, the plant is further defined as a forage crop. In particular embodiments the plant is a forage legume. In even more particular embodiments the plant is alfalfa.

The invention also provides a method further defined as comprising the preparation of a transgenic progeny plant of any generation of the plant, wherein the progeny plant comprises the selected nucleic acid sequence. A plant or plant part prepared by this method is also provided.

Yet another aspect of the invention is a method of making food or feed for human or animal consumption comprising: (a) obtaining the plant comprising the selected nucleic acid; (b) growing the plant under plant growth conditions to produce plant tissue from the plant; and (c) preparing food or feed for human or animal consumption from the plant tissue. In certain embodiments, preparing food or feed comprises harvesting the plant tissue. In particular embodiments, the food or feed is hay, silage, starch, protein, meal, flour or grain.

BRIEF DESCRIPTION OF THE DRAWINGS

The following drawings form part of the present specification and are included to further demonstrate certain aspects of the invention. The invention may be better understood by reference to one or more of these drawings in combination with the detailed description of specific embodiments presented herein:

FIG. 11A-D: Multiple sequence alignment of the open reading frames of UGT72L1 (SEQ ID NO:1) and other UGTs active with flavonoid substrates. The PSPG box, representing the binding site of UDP-glucose, extends between amino acid positions 309 to 314 and 387 to 430. Residues His-22 and Asp-121 (in UGT71G1) are marked with asterisks. Residues defining the acceptor binding site of UGT71G1 are marked with arrows. The alignment was performed using ClustalX (Thompson et al., 1997). AS, arbutin synthase (GenBank AJ310148; SEQ ID NO:29) from *Rauvolfia serpentina*. GT22D (ABI94020; SEQ ID NO:30), GT22E09 (ABI94021; SEQ ID NO:31), GT29C (ABI94022; SEQ ID NO:32), UGT71G1 (GT29H; AAW56092; SEQ ID NO:33), GT63G (ABI94023; SEQ ID NO:34), GT67A (ABI94024; SEQ ID NO:35), GT83F (ABI94025; SEQ ID NO:36) and GT99D (ABI94020; SEQ ID NO:37) were from *M. truncatula* (Modolo et al., 2007).

BRIEF DESCRIPTION OF THE SEQUENCES

Figure 1A:
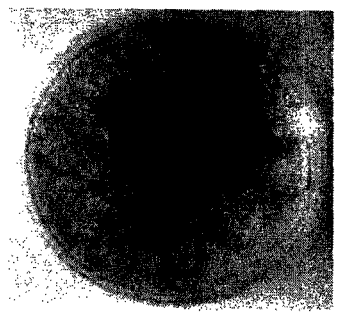
FIG. 1A-D: Phenotypic appearance of transgenic *M. truncatula* hairy roots. (A) Unstained TT2-expressing roots. (B) Unstained vector control roots. (C) DMACA-stained TT2-expressing roots. (D) DMACA-stained empty vector control roots.

SEQ ID NO:1 Amino acid sequence of *M. truncatula* UGT72L1.
SEQ ID NO:2 Nucleotide sequence encoding *M. truncatula* UGT72L1.
SEQ ID NO:3 Amino acid sequence of MBP-UGT72L1 fusion protein.
SEQ ID NO:4 Nucleotide sequence encoding MBP-UGT72L1 fusion protein.
SEQ ID NO:5 Nucleotide sequence encoding *M. truncatula* ANR.
SEQ ID NO:6 *M. truncatula* Dihydroflavonol Reductase (DFR) nucleotide sequence.
SEQ ID NO:7 *M. truncatula* Dihydroflavonol Reductase (DFR) nucleotide sequence.
SEQ ID NO:8 *Medicago sativa* Chalcone Isomerase (CHI) nucleotide sequence.
SEQ ID NO:9 *Medicago sativa* Chalcone Isomerase (CHI) nucleotide sequence.
SEQ ID NO:10 *Medicago sativa* Chalcone Isomerase (CHI) nucleotide sequence.
SEQ ID NO:11 *Medicago sativa* Chalcone Isomerase (CHI) nucleotide sequence.
SEQ ID NO:12 *A. thaliana* PAP1 nucleotide sequence.
SEQ ID NO:13 *A. thaliana* TTG1 nucleotide sequence
SEQ ID NO:14 *A. thaliana* TTG1 amino acid sequence
SEQ ID NO:15 *A. thaliana* TT1 nucleotide sequence
SEQ ID NO:16 *A. thaliana* TT1 amino acid sequence
SEQ ID NO:17 *A. thaliana* TT2 amino acid sequence
SEQ ID NO:18 *A. thaliana* TT8 amino acid sequence.
SEQ ID NO:19 *A. thaliana* TT12 amino acid sequence.
SEQ ID NO:20 *A. thaliana* ANR nucleotide sequence.
SEQ ID NO:21 *A. thaliana* ANR amino acid sequence.
SEQ ID NO:22 *M. truncatula* ANR amino acid sequence.
SEQ ID NO:23 *A. thaliana* TT2 nucleotide sequence.
SEQ ID NO:24 *A. thaliana* TT8 nucleotide sequence.
SEQ ID NO:25-26 Synthetic primers MtUGT72L1CF and MtUGT72L1R.
SEQ ID NO:27-28 Synthetic primers MtUGT72L1BF and MtUGT72L1PR.
SEQ ID NO:29 *Rauvolfia serpentina* Arbutin Synthase amino acid sequence.
SEQ ID NO:30 *M. truncatula* GT22D UGT amino acid sequence.
SEQ ID NO:31 *M. truncatula* GT22E09 UGT amino acid sequence.
SEQ ID NO:32 *M. truncatula* GT29C UGT amino acid sequence.
SEQ ID NO:33 *M. truncatula* GT29H (UGT71G1) UGT amino acid sequence.
SEQ ID NO:34 *M. truncatula* GT63G UGT amino acid sequence.
SEQ ID NO:35 *M. truncatula* GT67A UGT amino acid sequence.
SEQ ID NO:36 *M. truncatula* GT83F UGT amino acid sequence.
SEQ ID NO:37 *M. truncatula* GT99D UGT amino acid sequence.
SEQ ID NO:38 *M. truncatula* MtLAP1 amino acid sequence.
SEQ ID NO:39-66 Primers for amplification of AtTT2, MtANR and other PA biosynthesis related genes and sequences as described in Sharma and Dixon (2005) (SEQ ID NOs:39-40: for amplification of BAN (ANR); SEQ ID. NOs:41-42: TT12; SEQ ID NOs:43-44: DFR; SEQ ID NOs:45-46:LDOX; SEQ ID NOs:47-48:TT19; SEQ ID NOs:49-50: CHS; SEQ ID NOs:51-52: PAP1; SEQ ID NOs:53-54: ACT; SEQ ID NOs:55-56: TT2; SEQ ID NOs:57-58: TT1; SEQ ID NOs:59-60: TT8; SEQ ID NOs:61-62: TT16; SEQ ID NOs:63-64: TTG1; SEQ ID NOs:65-66: TTG2).

DETAILED DESCRIPTION OF THE INVENTION

The invention overcomes the limitations of the prior art by providing novel methods and compositions for the modification of anthocyanin and proanthocyanidin (PA) metabolism in plants, such as in legume plants and plant tissues that otherwise lack significant anthocyanin or PA content, and including, for example, aerial portions of alfalfa plants, by identification of a novel glucosyltransferase highly specific for epicatechin. Biochemical evidence indicates that this enzyme, termed UGT72L1 (amino acid sequence given at SEQ ID NO:1; coding sequence given at SEQ ID NO:2), has a high specificity for epicatechin. Its expression kinetics in developing seeds are also comparable to that of other genes, such as ANR and CHS, involved in PA biosynthesis. This glycosyltransferase is induced by TT2 and expressed primarily in the *Medicago* seed coat and is important for PA and tannin biosynthesis.

The bulk of the PAs that accumulate in TT2-expressing *Medicago* hairy roots are insoluble polymers. Thus, TT2 and/or a corresponding *M. truncatula* gene product activates genes for precursor synthesis, transport, oligomerization and ultimate accumulation as high molecular weight polymers, unless some of these functions are already expressed in control roots. *Medicago* genes with similarity to the MATE transporter TT12, the glutathione S-transferase TT19, and the proton pumping ATPase AHA10, all of which are implicated in PA transport and/or accumulation (Debeaujon et al., 2001; Kitamura et al., 2004, Baxter et al, 2005), were only weakly induced by TT2 in the hairy roots. These genes are regulated by TT2 in *Arabidopsis* (Lepiniec et al., 2006; Sharma et al., 2005). Epicatechin glucoside is transported into the vacuole by the TT12 transporter (FIG. 7); and transport of the glucoside may also be important in regulating PA synthesis. The glucoside may also act as a starter unit or a terminator unit for tannin biosynthesis, or influence polymerization of subunits with the linkages in the correct position. Thus the production and accumulation of PA can be induced, altered, or enhanced.

It is shown herein that the *Medicago truncatula* UGT72L1 shows specificity for glycosylation of epicatechin. This is unexpected given that other glycosyltransferases active on related flavonoid substrates are generally quite promiscuous in their catalytic specificity.

Alfalfa lacks significant levels of PAs in the aerial portions, although high levels are found in the seed coat (Koupai-Abyazani et al., 1993), and DMACA-reactive material that may represent PAs is also present in trichomes of glandular haired varieties (Aziz et al., 2005). To date, classical breeding approaches have failed to introduce PAs into alfalfa foliage, and it has been accepted that such introduction will likely require a biotechnological solution (Lees, 1992). As the anthocyanin precursors of PAs are also essentially absent from unstressed alfalfa foliage, introducing the PA trait requires increasing, or introducing de novo, the activities of at least ten known biosynthetic enzymes, plus a requirement for several additional functions associated with transport and sequestration of intermediates and products.

Many forage crops are low in PAs and may promote bloat, including Medicago spp such as alfalfa (Medicago sativa) and annual medics, white clover, ball clover, Persian clover, red clover, crimson clover, berseem clover, arrowleaf clover, alsike clover, subterranean clovers, fenugreek, and sweetclover (Melilotus spp.). "Pasture bloat" can be caused by grazing of wheat pastures and other lush foliage such as fast-growing monocots. "Feedlot bloat" also occurs in cattle fed high-grain rations that may or may not contain legume forage, green-chopped legumes, or other finely ground feed. In these cases, direct engineering of PA accumulation in the forage plant may be used in accordance with the invention to prevent bloat. Further, PA modification could be engineered into feed components that are blended or added to bloat-causing components to reduce the bloat incidence in animals consuming the mixed feed.

One application of the invention is thus the modification of PA biosynthesis in plants with low. PA content, resulting in plants, plant parts, or products such as silage or hay, with enhanced value. Alfalfa is one such plant. PAs are made in alfalfa (Medicago sativa), as in Arabidopsis, in the seed coat, but do not accumulate in the leaves (Koupai-Abyazani et al., 1993; Skadhauge et al., 1997). Nonetheless, alfalfa is the world's major forage legume. Therefore, introducing PA biosynthesis to the leaves or other tissues of alfalfa or other low PA plants would substantially improve the utility of this crop for feed by reduction of its potential for causing pasture bloat. Forage crops that accumulate PAs in leaves have low bloating potential; these include Lotus corniculatus, Leucaena leucocephala, Hedysarum sulfurescens and Robinia spp, among others. Thus, an application of the invention is to alter tannin composition, amount, and/or chain length, for instance resulting in qualitative or quantitative alterations in tannin content in transgenic plants expressing epicatechin glucosyltransferase UGT72L1.

Technology that could result in constitutive expression of PAs in high protein forage crops would also greatly improve the agronomic value of crops in addition to alfalfa. In addition, the potential importance of anthocyanins and PAs in human health makes methods for their facile production in plants necessary for the full development of their therapeutic potential, for instance allowing their production and use as nutraceuticals or as food colorants.

At least 45 genes are up-regulated in M. truncatula tissues at least 2-fold in response to constitutive expression of TT2, most of which are apparently involved in anthocyanin biosynthesis. The present invention provides methods and compositions for increasing PA production comprising introducing transgenic epicatechin glucosyltransferase coding sequences, e.g., UGT72L1. In certain aspects, this may be provided in combination with a sequence that encodes a polypeptide that activates anthocyanin or proanthocyanidin synthesis, such as an anthocyanidin reductase (ANR) coding sequence, which functions to direct precursors from the anthocyanin pathway into the formation of proanthocyanidins, or other PA biosynthesis coding sequence(s), such as an anthocyanidin glucosyltransferase.

I. APPLICATION OF THE INVENTION

As indicated above, one application of the invention is the introduction or increase of PA biosynthesis in plants. Such applications may result in forage improvement and nutritional improvement of foods. In accordance with the invention this may be carried out by introduction of a gene encoding UGT72L1 alone or in combination with other PA biosynthesis genes. The invention may be used to improve the nutritional quality of plants. Catechins and similar flavonoids have been reported to behave as strong antioxidants and have other properties which may make their consumption beneficial to human and animal health. Also, such compounds are generally antimicrobial, and their presence may improve food quality by preventing pre- and post-harvest damage. Accordingly, increases in PA biosynthesis may be used to achieve the associated health benefits.

Figure 7:
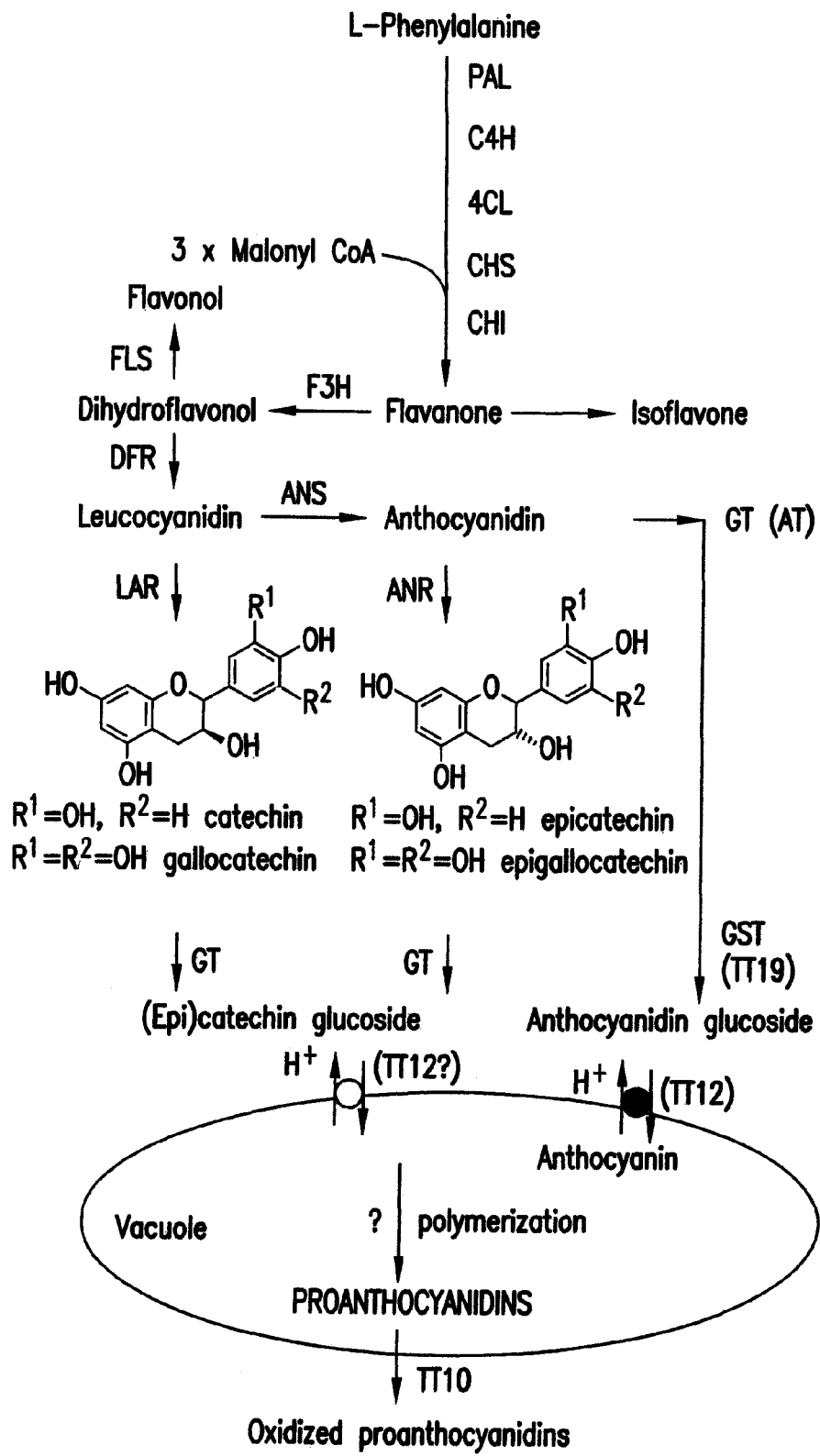
FIG. 7: Simplified scheme for the biosynthesis of anthocyanins and PAs. Enzymes are: PAL, L-phenylalanine ammonia-lyase; C4H, cinnamate 4-hydroxylase; 4CL, 4-coumarate CoA ligase; CHS, chalcone synthase; CHI chalcone isomerase; F3H, flavanone 3-β-hydroxylase; FLS, flavonol synthase; DFR, dihydroflavonol reductase; LAR, leucoanthocyanidin reductase; ANS, anthocyanidin synthase; ANR, anthocyanidin reductase; GST, glutathione S-transferase; GT, glucosyltransferase; AT, acyl transferase.

In addition, other genes may be used in conjunction with UGT72L1 to enhance the accumulation of proanthocyanidins, for instance by providing a gene encoding ANR (E.C. 1.3.1.77), or other enzyme in the PA synthesis pathway. An ANR or other proanthocyanidin biosynthesis gene may be isolated by PCR, for instance by utilizing a nucleotide primer such as a BAN primer for instance as found in U.S. Patent Publn. 2004/0093632. Thus, an ANR (BAN) homolog, for instance from Medicago truncatula (e.g., encoded by SEQ ID NO:5) may be utilized. Other anthocyanin synthetic enzyme activities as shown in FIG. 7 may also be utilized in conjunction with the UGT72L1 gene, such as dihydroflavonol reductase (DFR; E.C. 1.1.1.219)) coding sequences (SEQ ID NOs: 6-7). The UGT72L1 gene may thus find use as part of a combination of genes to introduce or increase condensed tannin biosynthesis in numerous species, for forage improvement and nutritional improvement of foods. PA expression could also be modulated using a transgenic chalcone isomerase coding sequence (e.g., McKhann and Hirsch, 1994; Liu et al., 2002; (e.g., SEQ ID NOs:8-11)).

The invention also relates to feed products containing one or more of the sequences of the present invention. Such products produced from a recombinant plant or seed containing one or more of the nucleotide sequences of the present invention are specifically contemplated as embodiments of the present invention. A feed product containing one or more of the sequences of the present invention is intended to include, but not be limited to, feed, harvested hay, silage, crushed or whole grains or seeds of a recombinant plant or seed containing one or more of the sequences of the present invention.

Over-expression of Medicago chalcone isomerase may increase flavonoid biosynthesis in Arabidopsis (e.g., Liu et al., 2002). This could thus be used in combination with UGT72L1 to produce more PA. An Arabidopsis or other PAP-1 (Borevitz, 2000; e.g., SEQ ID NO:12), or a sequence that encodes LAP1, or that encodes MtLAP1-like polypeptide (e.g., SEQ ID NO:38) could also be used to increase flux into the pathway. UGT72L1 could also be used in conjunction with any one or more other regulatory gene products such as TTG1 (GenBank Accession No. AJ133743, SEQ ID NO: 13, SEQ ID NO:14); TT1 (GenBank Accession No. AF190298; SEQ ID NO:15, SEQ ID NO:16); TT2 (GenBank accession number AJ299452, SEQ ID NO:17, SEQ ID NO:23); and TT8 (GenBank Accession No. AJ277509; SEQ ID NO:18). Benefit may also be obtained from use of UGT72L1 in conjunction with a sequence encoding TT12 (GenBank Accession No. AJ294464; e.g., SEQ ID NO: 19) for transport of PA to the vacuole. Any combination of the foregoing sequences may therefore be used with the invention.

A UGT72L1 encoding sequence may be used in conjunction with a sequence encoding an ANR (BAN) homolog, for example as described in U.S. patent application Ser. No. 12/108,332, which is herein incorporated by reference in it entirety. For instance, ANR sequences which may be utilized include those from M. truncatula (e.g., SEQ ID NO:5) or A. thaliana (e.g., SEQ ID NO:20). The corresponding encoded peptides are given in SEQ ID NO:22 and SEQ ID NO:21. One aspect of the invention thus provides a UGT72L1-encoding sequence, such as SEQ ID NO:1, used in conjunction with another PA biosynthesis sequence. Also provided are nucleic acids hybridizing to a nucleic acid sequence encoding a polypeptide conferring epicatechin glucosylase activity, or their complements.

Modulation of the phenotype of a plant or plant tissue may be obtained in accordance with the invention by introduction of recombinant nucleic acids comprising a UGT72L1 coding sequence. Other aspects of the invention are sequences that hybridize to UGT72L1 coding sequence provided herein under moderate or high stringency conditions. Such sequences may display, for example, at least 75%, 80%, 85%, 90%, 95%, 98%, or 99% sequence similarity with SEQ ID NO: 1. As used herein, "hybridization" or "hybridizes" is understood to mean the forming of a double or triple stranded molecule or a molecule with partial double or triple stranded nature. As used herein "stringent condition(s)" or "high stringency" are those conditions that allow hybridization between or within one or more nucleic acid strand(s) containing complementary sequence(s), but precludes hybridization of random sequences.

Stringent conditions tolerate little mismatch between a nucleic acid and a target strand. Such conditions are well known to those of ordinary skill in the art, and are preferred for applications requiring high selectivity. Medium stringent conditions may comprise relatively low salt and/or relatively high temperature conditions, such as provided by about 1×SSC, and 65° C. High stringency may be defined as 0.02M to 0.10M NaCl and 50° C. to 70° C. Specific examples of such conditions include 0.02M NaCl and 50° C.; 0.02M NaCl and 60° C.; and 0.02M NaCl and 70° C.

Alterations of the native amino acid sequence to produce variant polypeptides can be prepared by a variety of means known to those ordinarily skilled in the art. For instance, amino acid substitutions can be conveniently introduced into the polypeptides by changing the sequence of the nucleic acid molecule at the time of synthesis. Site-specific mutations can also be introduced by ligating into an expression vector a synthesized oligonucleotide comprising the modified sequence. Alternately, oligonucleotide-directed, site-specific mutagenesis procedures can be used, such as disclosed in Walder et al. (1986); and U.S. Pat. Nos. 4,518,584 and 4,737,462.

In making such changes, the hydropathic index of amino acids may be considered. The importance of the hydropathic amino acid index in conferring interactive biological function on a protein is generally understood in the art (e.g., Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid may be assigned a hydropathic index on the basis of their hydrophobicity and charge characteristics. These are, for instance: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate/glutamine/aspartate/asparagine (−3.5); lysine (−3.9); and arginine (−4.5). It is known in the art that certain amino acids may be substituted by other amino acids having a similar hydropathic index or score and still result in a protein with similar biological activity, i.e., still obtain a biologically functional protein. In making such changes, the substitution of amino acids whose hydropathic indices are within +/−2 is preferred, those within +/−1 are more preferred, and those within +/−0.5 are most preferred.

It is also understood in the art that the substitution of like amino acids may be made effectively on the basis of hydrophilicity. U.S. Pat. No. 4,554,101 states that the greatest local average hydrophilicity of a protein, as governed by the hydrophilicity of its adjacent amino acids, correlates with a biological property of the protein. The following hydrophilicity values have been assigned to amino acids: arginine/lysine (+3.0); aspartate/glutamate (+3.0.+-0.1); serine (+0.3); asparagine/glutamine (+0.2); glycine (0); threonine (−0.4); proline (−0.5.+-0.1); alanine/histidine (−0.5); cysteine (−1.0); methionine (−1.3); valine (−1.5); leucine/isoleucine (−1.8); tyrosine (−2.3); phenylalanine (−2.5); and tryptophan (−3.4).

It is understood that an amino acid may be substituted by another amino acid having a similar hydrophilicity score and still result in a protein with similar biological activity, i.e., still obtain a biologically functional protein. In making such changes, the substitution of amino acids whose hydropathic indices are within .+−0.2 is preferred, those within .+−0.1 are more preferred, and those within .+−.0.5 are most preferred.

As outlined above, amino acid substitutions are therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine, and isoleucine.

It is understood that the temperature and ionic strength of a desired stringency are determined in part by the length of the particular nucleic acid(s), the length and nucleobase content of the target sequence(s), the charge composition of the nucleic acid(s), and to the presence or concentration of formamide, tetramethylammonium chloride or other solvent(s) in a hybridization mixture. It is also understood that compositions and conditions for hybridization are mentioned by way of non-limiting examples only, and that the desired stringency for a particular hybridization reaction in a plant cell is often determined empirically by comparison to one or more positive or negative controls. Depending on the application envisioned it is preferred to employ varying conditions of hybridization to achieve varying degrees of selectivity of a nucleic acid towards a target sequence. Thus, nucleotide sequences displaying 90%, 95%, 98%, 99%, or greater similarity over the length of their coding regions to the UGT72L1 coding sequences (SEQ ID NOs:2 or 4) provided herein, and that encode a functional UGT72L1 protein, are also an aspect of the invention, as is a UGT72L1 protein encoded by such a gene.

II. PLANT TRANSFORMATION CONSTRUCTS

Certain embodiments of the current invention concern plant transformation constructs. For example, one aspect of the current invention is a plant transformation vector comprising a epicatechin glucosyltransferase coding sequence alone, or in combination with one or more PA biosynthesis gene(s). Examples of PA biosynthesis genes include BAN (i.e., ANR), PAP-1, TTG1, TT2, TT1, TT8, and/or TT12. Exemplary PA biosynthesis coding sequences for use with the invention also include the *Arabidopsis* 172 coding sequence (SEQ ID NO:23), which encodes the polypeptide sequence of SEQ ID NO:17, as well as a *Medicago truncatula* or *A. thaliana* BAN DNA sequence or encoded BAN polypeptide (e.g., SEQ ID NO:5, SEQ ID NOs:20-22). Such UGT72L1 coding sequences may encode a polypeptide of SEQ ID NOs:1 or 3, or fragment thereof, displaying epicatechin glucosylase activity, for instance comprising the nucleotide sequence of SEQ ID NOs:2 or 4. Such coding sequences may be present in one or more plant expression cassettes and/or transformation vectors for introduction to a plant cell.

In certain embodiments of the invention, coding sequences are provided operably linked to a heterologous promoter, in either sense or antisense orientation. Expression constructs are also provided comprising these sequences, as are plants and plant cells transformed with the sequences.

The construction of vectors which may be employed in conjunction with plant transformation techniques using these or other sequences according to the invention will be known to those of skill of the art in light of the present disclosure (see, for example, Sambrook et al., 1989; Gelvin et al., 1990). The techniques of the current invention are thus not limited to any particular nucleic acid sequences.

One important use of the sequences provided by the invention will be in the alteration of plant phenotypes by genetic transformation with sense or antisense PA biosynthesis genes. The PA biosynthesis gene may be provided with other sequences. Where an expressible coding region that is not necessarily a marker coding region is employed in combination with a marker coding region, one may employ the separate coding regions on either the same or different DNA segments for transformation. In the latter case, the different vectors are delivered concurrently to recipient cells to maximize cotransformation.

The choice of any additional elements used in conjunction with the PA biosynthesis coding sequences will often depend on the purpose of the transformation. One of the major purposes of transformation of crop plants is to add commercially desirable, agronomically important traits to the plant. As PAs are known to confer many beneficial effects on health, one such trait is increased biosynthesis of tannins. Alternatively, plants may be engineered to decrease synthesis of PA and increase anthocyanin content, for instance to promote production of a food colorant. Identification and engineered expression of epicatechin glucosyltransferase coding sequences as well as sequences from additional anthocyanin and PA biosynthesis-related functions allows for rational manipulation of the biosynthetic flux through these pathways.

Particularly useful for transformation are expression cassettes which have been isolated from such vectors. DNA segments used for transforming plant cells will, of course, generally comprise the cDNA, gene or genes which one desires to introduce into and have expressed in the host cells. These DNA segments can further include structures such as promoters, enhancers, polylinkers, or even regulatory genes as desired. The DNA segment or gene chosen for cellular introduction will often encode a protein which will be expressed in the resultant recombinant cells resulting in a screenable or selectable trait and/or which will impart an improved phenotype to the resulting transgenic plant. However, this may not always be the case, and the present invention also encompasses transgenic plants incorporating non-expressed transgenes. Preferred components likely to be included with vectors used in the current invention are as follows.

A. Regulatory Elements

Exemplary promoters for expression of a nucleic acid sequence include plant promoter such as the CaMV 35S promoter (Odell et al., 1985), or others such as CaMV 19S (Lawton et al., 1987), nos (Ebert et al., 1987), Adh (Walker et al., 1987), sucrose synthase (Yang and Russell, 1990), a-tubulin, actin (Wang et al., 1992), cab (Sullivan et al., 1989), PEPCase (Hudspeth and Grula, 1989) or those associated with the R gene complex (Chandler et al., 1989). Tissue specific promoters such as root cell promoters (Conkling et al., 1990) and tissue specific enhancers (Fromm et al., 1986) are also contemplated to be particularly useful, as are inducible promoters such as ABA- and turgor-inducible promoters. In certain embodiments of the invention, the native promoter of a PA biosynthesis gene may be used.

The DNA sequence between the transcription initiation site and the start of the coding sequence, i.e., the untranslated leader sequence, can also influence gene expression. One may thus wish to employ a particular leader sequence with a transformation construct of the invention. Preferred leader sequences are contemplated to include those which comprise sequences predicted to direct optimum expression of the attached gene, i.e., to include a preferred consensus leader sequence which may increase or maintain mRNA stability and prevent inappropriate initiation of translation. The choice of such sequences will be known to those of skill in the art in light of the present disclosure. Sequences that are derived from genes that are highly expressed in plants will typically be preferred.

It is specifically envisioned that PA biosynthesis coding sequences may be introduced under the control of novel promoters or enhancers, etc., or homologous or tissue specific promoters or control elements. Vectors for use in tissue-specific targeting of genes in transgenic plants will typically include tissue-specific promoters and may also include other tissue-specific control elements such as enhancer sequences. Promoters which direct specific or enhanced expression in certain plant tissues will be known to those of skill in the art in light of the present disclosure. These include, for example, the rbcS promoter, specific for green tissue; the ocs, nos and mas promoters which have higher activity in roots or wounded leaf tissue; a truncated (−90 to +8) 35S promoter which directs enhanced expression in roots, and an α-tubulin gene that also directs expression in roots.

B. Terminators

Transformation constructs prepared in accordance with the invention will typically include a 3' end DNA sequence that acts as a signal to terminate transcription and allow for the poly-adenylation of the mRNA produced by coding sequences operably linked to a PA biosynthesis gene. In one embodiment of the invention, the native terminator of a PA biosynthesis gene is used. Alternatively, a heterologous 3' end may enhance the expression of sense or antisense PA biosynthesis genes. Terminators which are deemed to be particularly useful in this context include those from the nopaline synthase gene of *Agrobacterium tumefaciens* (nos 3' end) (Bevan et al., 1983), the terminator for the T7 transcript from the octopine synthase gene of *Agrobacterium tumefaciens*, and the 3' end of the protease inhibitor I or II genes from potato or tomato. Regulatory elements such as an Adh intron (Callis et al., 1987), sucrose synthase intron (Vasil et al., 1989) or TMV omega element (Gallie et al., 1989), may further be included where desired.

C. Transit or Signal Peptides

Sequences that are joined to the coding sequence of an expressed gene, which are removed post-translationally from the initial translation product and which facilitate the transport of the protein into or through intracellular or extracellular membranes, are termed transit (usually into vacuoles, vesicles, plastids and other intracellular organelles) and signal sequences (usually to the endoplasmic reticulum, golgi apparatus and outside of the cellular membrane). By facilitating the transport of the protein into compartments inside and outside the cell, these sequences may increase the accumulation of gene product protecting them from proteolytic degradation. These sequences also allow for additional mRNA sequences from highly expressed genes to be attached to the coding sequence of the genes. Since mRNA being translated by ribosomes is more stable than naked mRNA, the presence of translatable mRNA in front of the gene may increase the overall stability of the mRNA transcript from the gene and thereby increase synthesis of the gene product. Since transit and signal sequences are usually post-translationally removed from the initial translation product, the use of these sequences allows for the addition of extra translated sequences that may not appear on the final polypeptide. It further is contemplated that targeting of certain proteins may be desirable in order to enhance the stability of the protein (U.S. Pat. No. 5,545,818, incorporated herein by reference in its entirety).

Additionally, vectors may be constructed and employed in the intracellular targeting of a specific gene product within the cells of a transgenic plant or in directing a protein to the extracellular environment. This generally will be achieved by joining a DNA sequence encoding a transit or signal peptide sequence to the coding sequence of a particular gene. The resultant transit, or signal, peptide will transport the protein to a particular intracellular, or extracellular destination, respectively, and will then be post-translationally removed.

D. Marker Genes

By employing a selectable or screenable marker protein, one can provide or enhance the ability to identify transformants. "Marker genes" are genes that impart a distinct phenotype to cells expressing the marker protein and thus allow such transformed cells to be distinguished from cells that do not have the marker. Such genes may encode either a selectable or screenable marker, depending on whether the marker confers a trait which one can "select" for by chemical means, i.e., through the use of a selective agent (e.g., a herbicide, antibiotic, or the like), or whether it is simply a trait that one can identify through observation or testing, i.e., by "screening" (e.g., the green fluorescent protein). Of course, many examples of suitable marker proteins are known to the art and can be employed in the practice of the invention.

Included within the terms "selectable" or "screenable markers" also are genes which encode a "secretable marker" whose secretion can be detected as a means of identifying or selecting for transformed cells. Examples include markers which are secretable antigens that can be identified by antibody interaction, or even secretable enzymes which can be detected by their catalytic activity. Secretable proteins fall into a number of classes, including small, diffusible proteins detectable, e.g., by ELISA; small active enzymes detectable in extracellular solution (e.g., α-amylase, β-lactamase, phosphinothricin acetyltransferase); and proteins that are inserted or trapped in the cell wall (e.g., proteins that include a leader sequence such as that found in the expression unit of extensin or tobacco PR-S).

With regard to selectable secretable markers, the use of a gene that encodes a protein that becomes sequestered in the cell wall, and which protein includes a unique epitope is considered to be particularly advantageous. Such a secreted antigen marker would ideally employ an epitope sequence that would provide low background in plant tissue, a promoter-leader sequence that would impart efficient expression and targeting across the plasma membrane, and would produce protein that is bound in the cell wall and yet accessible to antibodies. A normally secreted wall protein modified to include a unique epitope would satisfy all such requirements.

Many selectable marker coding regions are known and could be used with the present invention including, but not limited to, neo (Potrykus et al., 1985), which provides kanamycin resistance and can be selected for using kanamycin, G418, paromomycin, etc.; bar, which confers bialaphos or phosphinothricin resistance; a mutant EPSP synthase protein (Hinchee et al., 1988) conferring glyphosate resistance; a nitrilase such as bxn from *Klebsiella ozaenae* which confers resistance to bromoxynil (Stalker et al., 1988); a mutant acetolactate synthase (ALS) which confers resistance to imidazolinone, sulfonylurea or other ALS inhibiting chemicals (European Patent Application 154,204, 1985); a methotrexate resistant DHFR (Thillet et al., 1988), a dalapon dehalogenase that confers resistance to the herbicide dalapon; or a mutated anthranilate synthase that confers resistance to 5-methyl tryptophan.

An illustrative embodiment of selectable marker capable of being used in systems to select transformants are those that encode the enzyme phosphinothricin acetyltransferase, such as the bar gene from *Streptomyces hygroscopicus* or the pat gene from *Streptomyces viridochromogenes*. The enzyme phosphinothricin acetyl transferase (PAT) inactivates the active ingredient in the herbicide bialaphos, phosphinothricin (PPT). PPT inhibits glutamine synthetase, (Murakami et al., 1986; Twell et al., 1989) causing rapid accumulation of ammonia and cell death.

Screenable markers that may be employed include a β-glucuronidase (GUS) or uidA gene which encodes an enzyme for which various chromogenic substrates are known; an R-locus gene, which encodes a product that regulates the production of anthocyanin pigments (red color) in plant tissues (Dellaporta et al., 1988); a β-lactamase gene (Sutcliffe, 1978), which encodes an enzyme for which various chromogenic substrates are known (e.g., PADAC, a chromogenic cephalosporin); a xylE gene (Zukowsky et al., 1983) which encodes a catechol dioxygenase that can convert chromogenic catechols; an α-amylase gene (Ikuta et al., 1990); a tyrosinase gene (Katz et al., 1983) which encodes an enzyme capable of oxidizing tyrosine to DOPA and dopaquinone which in turn condenses to form the easily-detectable compound melanin; a β-galactosidase gene, which encodes an enzyme for which there are chromogenic substrates; a luciferase (lux) gene (Ow et al., 1986), which allows for bioluminescence detection; an aequorin gene (Prasher et al., 1985) which may be employed in calcium-sensitive bioluminescence detection; or a gene encoding for green fluorescent protein (Sheen et al., 1995; Haseloff et al., 1997; Reichel et al., 1996; Tian et al., 1997; WO 97/41228).

Another screenable marker contemplated for use in the present invention is firefly luciferase, encoded by the lux gene. The presence of the lux gene in transformed cells may be detected using, for example, X-ray film, scintillation counting, fluorescent spectrophotometry, low-light video cameras, photon counting cameras or multiwell luminometry. It also is envisioned that this system may be developed for populational screening for bioluminescence, such as on tissue culture plates, or even for whole plant screening. The gene which encodes green fluorescent protein (GFP) is also contemplated as a particularly useful reporter gene (Sheen et al., 1995; Haseloff et al., 1997; Reichel et al., 1996; Tian et al., 1997; WO 97/41228). Expression of green fluorescent protein may be visualized in a cell or plant as fluorescence following illumination by particular wavelengths of light.

III. ANTISENSE AND RNAi CONSTRUCTS

Antisense treatments represent one way of altering PA biosynthesis in accordance with the invention. In this manner, the accumulation of PA precursors, including anthocyanidins, could also be achieved. As such, antisense technology may be used to "knock-out" the function of an anthocyanin biosynthesis gene or homologous sequences thereof, such as UGT78G1, to increase the pool of anthocyanidin available for PA formation.

Antisense methodology takes advantage of the fact that nucleic acids tend to pair with "complementary" sequences. By complementary, it is meant that polynucleotides are those which are capable of base-pairing according to the standard Watson-Crick complementarity rules. That is, the larger purines will base pair with the smaller pyrimidines to form combinations of guanine paired with cytosine (G:C) and adenine paired with either thymine (A:T) in the case of DNA, or adenine paired with uracil (A:U) in the case of RNA. Inclusion of less common bases such as inosine, 5-methylcytosine, 6-methyladenine, hypoxanthine and others in hybridizing sequences does not interfere with pairing.

Antisense constructs may be designed to bind to the promoter and other control regions, exons, introns or even exon-intron boundaries of a gene. It is contemplated that the most effective antisense constructs will include regions complementary to intron/exon splice junctions. Thus, it is proposed that a preferred embodiment includes an antisense construct with complementarity to regions within 50-200 bases of an intron-exon splice junction. It has been observed that some exon sequences can be included in the construct without seriously affecting the target selectivity thereof. The amount of exonic material included will vary depending on the particular exon and intron sequences used. One can readily test whether too much exon DNA is included simply by testing the constructs in vitro to determine whether normal cellular function is affected or whether the expression of related genes having complementary sequences is affected.

As stated above, "complementary" or "antisense" means polynucleotide sequences that are substantially complementary over their entire length and have very few base mismatches. For example, sequences of fifteen bases in length may be termed complementary when they have complementary nucleotides at thirteen or fourteen positions. Naturally, sequences which are completely complementary will be sequences which are entirely complementary throughout their entire length and have no base mismatches. Other sequences with lower degrees of homology also are contemplated. For example, an antisense construct which has limited regions of high homology, but also contains a non-homologous region (e.g., ribozyme; see above) could be designed. These molecules, though having less than 50% homology, would bind to target sequences under appropriate conditions.

It may be advantageous to combine portions of genomic DNA with cDNA or synthetic sequences to generate specific constructs. For example, where an intron is desired in the ultimate construct, a genomic clone will need to be used. The cDNA or a synthesized polynucleotide may provide more convenient restriction sites for the remaining portion of the construct and, therefore, would be used for the rest of the sequence.

RNA interference (RNAi) is a process utilizing endogenous cellular pathways whereby a double stranded RNA (dsRNA) specific target gene results in the degradation of the mRNA of interest. In recent years, RNAi has been used to perform gene "knockdown" in a number of species and experimental systems, from the nematode C. elegans, to plants, to insect embryos and cells in tissue culture (Fire et al., 1998; Martinez et al., 2002; McManus and Sharp, 2002). RNAi works through an endogenous pathway including the Dicer protein complex that generates ~21-nucleotide small interfering RNAs (siRNAs) from the original dsRNA and the RNA-induced silencing complex (RISC) that uses siRNA guides to recognize and degrade the corresponding mRNAs. Only transcripts complementary to the siRNA are cleaved and degraded, and thus the knock-down of mRNA expression is usually sequence specific. One of skill in the art would routinely be able to identify portions of, for instance, the UGT78G1 sequence, as targets for RNAi-mediated gene suppression to increase proanthocyanidin levels in alfalfa.

IV. TISSUE CULTURES

Tissue cultures may be used in certain transformation techniques for the preparation of cells for transformation and for the regeneration of plants therefrom. Maintenance of tissue cultures requires use of media and controlled environments. "Media" refers to the numerous nutrient mixtures that are used to grow cells in vitro, that is, outside of the intact living organism. The medium usually is a suspension of various categories of ingredients (salts, amino acids, growth regulators, sugars, buffers) that are required for growth of most cell types. However, each specific cell type requires a specific range of ingredient proportions for growth, and an even more specific range of formulas for optimum growth. Rate of cell growth also will vary among cultures initiated with the array of media that permit growth of that cell type.

Nutrient media is prepared as a liquid, but this may be solidified by adding the liquid to materials capable of providing a solid support. Agar is most commonly used for this purpose. Bacto™ agar (Difco-BD, Franklin Lakes, N.J.), Hazleton agar (Hazleton, Lenexa, Kans., USA), Gelrite® (Sigma, St. Louis, Mo.), PHYTAGEL (Sigma-Aldrich, St. Louis, Mo.), and GELGRO (ICN-MP Biochemicals, Irvine, Calif., USA) are specific types of solid support that are suitable for growth of plant cells in tissue culture.

Some cell types will grow and divide either in liquid suspension or on solid media. As disclosed herein, plant cells will grow in suspension or on solid medium, but regeneration of plants from suspension cultures typically requires transfer from liquid to solid media at some point in development. The type and extent of differentiation of cells in culture will be affected not only by the type of media used and by the environment, for example, pH, but also by whether media is solid or liquid.

Tissue that can be grown in a culture includes meristem cells, callus, immature embryos, hairy root cultures, and gametic cells such as microspores, pollen, sperm and egg cells. Callus may be initiated from tissue sources including, but not limited to, immature embryos, seedling apical meristems, root, leaf, microspores and the like. Those cells which are capable of proliferating as callus also are candidate recipient cells for genetic transformation.

Somatic cells are of various types. Embryogenic cells are one example of somatic cells which may be induced to regenerate a plant through embryo formation. Non-embryogenic cells are those which typically will not respond in such a fashion. Certain techniques may be used that enrich recipient cells within a cell population, for example by manual selection and culture of friable, embryogenic tissue. Manual selection techniques which can be employed to select target cells may include, e.g., assessing cell morphology and differentiation, or may use various physical or biological means. Cryopreservation also is a possible method of selecting for recipient cells.

Where employed, cultured cells may be grown either on solid supports or in the form of liquid suspensions. In either instance, nutrients may be provided to the cells in the form of media, and environmental conditions controlled. There are many types of tissue culture media comprised of various amino acids, salts, sugars, growth regulators and vitamins. Most of the media employed in the practice of the invention will have some similar components, but may differ in the composition and proportions of their ingredients depending on the particular application envisioned. For example, various cell types usually grow in more than one type of media, but will exhibit different growth rates and different morphologies, depending on the growth media. In some media, cells survive but do not divide. Various types of media suitable for culture of plant cells previously have been described. Examples of these media include, but are not limited to, the N6 medium described by Chu et al., (1975) and MS media (Murashige and Skoog, 1962).

V. METHODS FOR GENETIC TRANSFORMATION

Suitable methods for transformation of plant or other cells for use with the current invention are believed to include virtually any method by which DNA can be introduced into a cell, such as by direct delivery of DNA such as by PEG-mediated transformation of protoplasts (Omirulleh et al., 1993), by desiccation/inhibition-mediated DNA uptake (Potrykus et al., 1985), by electroporation (U.S. Pat. No. 5,384,253, specifically incorporated herein by reference in its entirety), by agitation with silicon carbide fibers (Kaeppler et al., 1990; U.S. Pat. No. 5,302,523, specifically incorporated herein by reference in its entirety; and U.S. Pat. No. 5,464,765, specifically incorporated herein by reference in its entirety), by *Agrobacterium*-mediated transformation (U.S. Pat. No. 5,591,616 and U.S. Pat. No. 5,563,055; both specifically incorporated herein by reference) and by acceleration of DNA coated particles (U.S. Pat. No. 5,550,318; U.S. Pat. No. 5,538,877; and U.S. Pat. No. 5,538,880; each specifically incorporated herein by reference in its entirety), etc. Through the application of techniques such as these, the cells of virtually any plant species may be stably transformed, and these cells developed into transgenic plants.

A. *Agrobacterium*-Mediated Transformation

*Agrobacterium*-mediated transfer is a widely applicable system for introducing genes into plant cells because the DNA can be introduced into whole plant tissues, thereby bypassing the need for regeneration of an intact plant from a protoplast. The use of *Agrobacterium*-mediated plant integrating vectors to introduce DNA into plant cells is well known in the art. See, for example, the methods described by Fraley et al., (1985), Rogers et al., (1987) and U.S. Pat. No. 5,563,055, specifically incorporated herein by reference in its entirety.

*Agrobacterium*-mediated transformation is most efficient in dicotyledonous plants and is the preferable method for transformation of dicots, including *Arabidopsis*, tobacco, tomato, alfalfa and potato. Indeed, while *Agrobacterium*-mediated transformation has been routinely used with dicotyledonous plants for a number of years, it has only recently become applicable to monocotyledonous plants. Advances in *Agrobacterium*-mediated transformation techniques have now made the technique applicable to nearly all monocotyledonous plants. For example, *Agrobacterium*-mediated transformation techniques have now been applied to rice (Hiei et al., 1997; U.S. Pat. No. 5,591,616), wheat (McCormac et al., 1998), barley (Tingay et al., 1997; McCormac et al., 1998), alfalfa (e.g., Thomas et al., 1990; McKersie et al., 1993) and maize (Ishida et al., 1996).

Modern *Agrobacterium* transformation vectors are capable of replication in *E. coli* as well as *Agrobacterium*, allowing for convenient manipulations as described (Klee et al., 1985). Moreover, recent technological advances in vectors for *Agrobacterium*-mediated gene transfer have improved the arrangement of genes and restriction sites in the vectors to facilitate the construction of vectors capable of expressing various polypeptide coding genes. The vectors described (Rogers et al., 1987) have convenient multi-linker regions flanked by a promoter and a polyadenylation site for direct expression of inserted polypeptide coding genes and are suitable for present purposes. In addition, *Agrobacterium* containing both armed and disarmed Ti genes can be used for the transformations. In those plant strains where *Agrobacterium*-mediated transformation is efficient, it is the method of choice because of the facile and defined nature of the gene transfer.

B. Electroporation

To effect transformation by electroporation, one may employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wounding in a controlled manner. Examples of some species which have been transformed by electroporation of intact cells include maize (U.S. Pat. No. 5,384,253; Rhodes et al., 1995; D'Halluin et al., 1992), wheat (Zhou et al., 1993), tomato (Hou and Lin, 1996), soybean (Christou et al., 1987) and tobacco (Lee et al., 1989).

One also may employ protoplasts for electroporation transformation of plants (Bates, 1994; Lazzeri, 1995). For example, the generation of transgenic soybean plants by electroporation of cotyledon-derived protoplasts is described by Dhir and Widholm in Intl. Patent Appl. Publ. No. WO 9217598 (specifically incorporated herein by reference). Other examples of species for which protoplast transformation has been described include barley (Lazerri, 1995), sorghum (Battraw et al., 1991), maize (Bhattacharjee et al., 1997), wheat (He et al., 1994) and tomato (Tsukada, 1989).

C. Microprojectile Bombardment

Another method for delivering transforming DNA segments to plant cells in accordance with the invention is microprojectile bombardment (U.S. Pat. No. 5,550,318; U.S. Pat. No. 5,538,880; U.S. Pat. No. 5,610,042; and PCT Application WO 94/09699; each of which is specifically incorporated herein by reference in its entirety). In this method, particles may be coated with nucleic acids and delivered into cells by a propelling force. Exemplary particles include those comprised of tungsten, platinum, and preferably, gold. It is contemplated that in some instances DNA precipitation onto metal particles would not be necessary for DNA delivery to a recipient cell using microprojectile bombardment. However, it is contemplated that particles may contain DNA rather than be coated with DNA. Hence, it is proposed that DNA-coated particles may increase the level of DNA delivery via particle bombardment but are not, in and of themselves, necessary.

For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate.

An illustrative embodiment of a method for delivering DNA into plant cells by acceleration is the Biolistics® Particle Delivery System (Dupont), which can be used to propel particles coated with DNA or cells through a screen, such as a stainless steel or nylon screen (e.g., NYTEX screen; Sefar America, Depew, N.Y. USA), onto a filter surface covered with plant cells cultured in suspension. The screen disperses the particles so that they are not delivered to the recipient cells in large aggregates. Microprojectile bombardment techniques are widely applicable, and may be used to transform virtually any plant species. Examples of species for which have been transformed by microprojectile bombardment include monocot species such as maize (PCT Application WO 95/06128), barley (Ritala et al., 1994), wheat (U.S. Pat. No. 5,563,055), and sorghum (Casa et al., 1993); as well as a number of dicots including tobacco (Tomes et al., 1990; Buising and Benbow, 1994), soybean (U.S. Pat. No. 5,322,783), sunflower (Knittel et al., 1994), peanut (Singsit et al., 1997), cotton (McCabe and Martinell, 1993), tomato (VanEck et al., 1995), and legumes in general (U.S. Pat. No. 5,563,055, specifically incorporated herein by reference in its entirety).

D. Other Transformation Methods

Transformation of protoplasts can be achieved using methods based on calcium phosphate precipitation, polyethylene glycol treatment, electroporation, and combinations of these treatments (see, e.g., Potrykus et al., 1985; Lorz et al., 1985; Omirulleh et al., 1993; Fromm et al., 1986; Uchimiya et al., 1986; Callis et al., 1987; Marcotte et al., 1988).

Application of these systems to different plant strains depends upon the ability to regenerate that particular plant strain from protoplasts. Illustrative methods for the regeneration of plants from protoplasts have been described (Toriyama et al., 1986; Yamada et al., 1986; Abdullah et al., 1986; Omirulleh et al., 1993 and U.S. Pat. No. 5,508,184). Examples of the use of direct uptake transformation of protoplasts include transformation of rice (Ghosh-Biswas et al., 1994), sorghum (Battraw and Hall, 1991), barley (Lazerri, 1995), oat (Zheng and Edwards, 1990) and maize (Omirulleh et al., 1993).

To transform plant strains that cannot be successfully regenerated from protoplasts, other ways to introduce DNA into intact cells or tissues can be utilized. For example, regeneration of cereals from immature embryos or explants can be effected as described (Vasil, 1989). Also, silicon carbide fiber-mediated transformation may be used with or without protoplasting (Kaeppler, 1990; Kaeppler et al., 1992; U.S. Pat. No. 5,563,055). Transformation with this technique is accomplished by agitating silicon carbide fibers together with cells in a DNA solution. DNA passively enters as the cells are punctured. This technique has been used successfully with, for example, the monocot cereals maize (PCT Application WO 95/06128; (Thompson, 1995) and rice (Nagatani, 1997).

VI. PRODUCTION AND CHARACTERIZATION OF STABLY TRANSFORMED PLANTS

After effecting delivery of exogenous DNA to recipient cells, the next steps generally concern identifying the transformed cells for further culturing and plant regeneration. In order to improve the ability to identify transformants, one may desire to employ a selectable or screenable marker gene with a transformation vector prepared in accordance with the invention. In this case, one would then generally assay the potentially transformed cell population by exposing the cells to a selective agent or agents, or one would screen the cells for the desired marker gene trait.

A. Selection

It is believed that DNA is introduced into only a small percentage of target cells in any one experiment. In order to provide an efficient system for identification of those cells receiving DNA and integrating it into their genomes one may employ a means for selecting those cells that are stably transformed. One exemplary embodiment of such a method is to introduce into the host cell, a marker gene which confers resistance to some normally inhibitory agent, such as an antibiotic or herbicide. Examples of antibiotics which may be used include the aminoglycoside antibiotics neomycin, kanamycin and paromomycin, or the antibiotic hygromycin. Resistance to the aminoglycoside antibiotics is conferred by aminoglycoside phosphostransferase enzymes such as neomycin phosphotransferase II (NPT II) or NPT I, whereas resistance to hygromycin is conferred by hygromycin phosphotransferase.

Potentially transformed cells then are exposed to the selective agent. In the population of surviving cells will be those cells where, generally, the resistance-conferring gene has been integrated and expressed at sufficient levels to permit cell survival. Cells may be tested further to confirm stable integration of the exogenous DNA.

One herbicide which constitutes a desirable selection agent is the broad spectrum herbicide bialaphos. Bialaphos is a tripeptide antibiotic produced by *Streptomyces hygroscopicus* and is composed of phosphinothricin (PPT), an analogue of L-glutamic acid, and two L-alanine residues. Upon removal of the L-alanine residues by intracellular peptidases, the PPT is released and is a potent inhibitor of glutamine synthetase (GS), a pivotal enzyme involved in ammonia assimilation and nitrogen metabolism (Ogawa et al., 1973). Synthetic PPT, the active ingredient in the herbicide Liberty™ also is effective as a selection agent. Inhibition of GS in plants by PPT causes the rapid accumulation of ammonia and death of the plant cells.

The organism producing bialaphos and other species of the genus *Streptomyces* also synthesizes an enzyme phosphinothricin acetyl transferase (PAT) which is encoded by the bar gene in *Streptomyces hygroscopicus* and the pat gene in *Streptomyces viridochromogenes*. The use of the herbicide resistance gene encoding phosphinothricin acetyl transferase (PAT) is referred to in DE 3642 829 A, wherein the gene is isolated from *Streptomyces viridochromogenes*. In the bacterial source organism, this enzyme acetylates the free amino group of PPT preventing auto-toxicity (Thompson et al., 1987). The bar gene has been cloned (Murakami et al., 1986; Thompson et al., 1987) and expressed in transgenic tobacco, tomato, potato (De Block et al., 1987) *Brassica* (De Block et al., 1989) and maize (U.S. Pat. No. 5,550,318). In previous reports, some transgenic plants which expressed the resistance gene were completely resistant to commercial formulations of PPT and bialaphos in greenhouses.

Another example of a herbicide which is useful for selection of transformed cell lines in the practice of the invention is the broad spectrum herbicide glyphosate. Glyphosate inhibits the action of the enzyme EPSPS which is active in the aromatic amino acid biosynthetic pathway. Inhibition of this enzyme leads to starvation for the amino acids phenylalanine, tyrosine, and tryptophan and secondary metabolites derived thereof. U.S. Pat. No. 4,535,060 describes the isolation of EPSPS mutations which confer glyphosate resistance on the *Salmonella typhimurium* gene for EPSPS, aroA. The EPSPS gene was cloned from *Zea mays* and mutations similar to those found in a glyphosate resistant aroA gene were introduced in vitro. Mutant genes encoding glyphosate resistant EPSPS enzymes are described in, for example, International Patent WO 97/4103. The best characterized mutant EPSPS gene conferring glyphosate resistance comprises amino acid changes at residues 102 and 106, although it is anticipated that other mutations will also be useful (PCT/WO97/4103).

To use the bar-bialaphos or the EPSPS-glyphosate selective system, transformed tissue is cultured for 0-28 days on nonselective medium and subsequently transferred to medium containing from 1-3 mg/l bialaphos or 1-3 mM glyphosate as appropriate. While ranges of 1-3 mg/l bialaphos or 1-3 mM glyphosate will typically be preferred, it is proposed that ranges of 0.1-50 mg/l bialaphos or 0.1-50 mM glyphosate will find utility.

It further is contemplated that the herbicide DALAPON, 2,2-dichloropropionic acid, may be useful for identification of transformed cells. The enzyme 2,2-dichloropropionic acid dehalogenase (deh) inactivates the herbicidal activity of 2,2-dichloropropionic acid and therefore confers herbicidal resistance on cells or plants expressing a gene encoding the dehalogenase enzyme (Buchanan-Wollaston et al., 1992; U.S. Pat. No. 5,508,468).

Alternatively, a gene encoding anthranilate synthase, which confers resistance to certain amino acid analogs, e.g., 5-methyltryptophan or 6-methyl anthranilate, may be useful as a selectable marker gene. The use of an anthranilate synthase gene as a selectable marker was described in U.S. Pat. No. 5,508,468.

An example of a screenable marker trait is the enzyme luciferase. In the presence of the substrate luciferin, cells expressing luciferase emit light which can be detected on photographic or x-ray film, in a luminometer (or liquid scintillation counter), by devices that enhance night vision, or by a highly light sensitive video camera, such as a photon counting camera. These assays are nondestructive and transformed cells may be cultured further following identification. The photon counting camera is especially valuable as it allows one to identify specific cells or groups of cells which are expressing luciferase and manipulate those in real time. Another screenable marker which may be used in a similar fashion is the gene coding for green fluorescent protein.

It further is contemplated that combinations of screenable and selectable markers will be useful for identification of transformed cells. In some cell or tissue types a selection agent, such as bialaphos or glyphosate, may either not provide enough killing activity to clearly recognize transformed cells or may cause substantial nonselective inhibition of transformants and nontransformants alike, thus causing the selection technique to not be effective. It is proposed that selection with a growth inhibiting compound, such as bialaphos or glyphosate at concentrations below those that cause 100% inhibition followed by screening of growing tissue for expression of a screenable marker gene such as luciferase would allow one to recover transformants from cell or tissue types that are not amenable to selection alone. It is proposed that combinations of selection and screening may enable one to identify transformants in a wider variety of cell and tissue types. This may be efficiently achieved using a gene fusion between a selectable marker gene and a screenable marker gene, for example, between an NPTII gene and a GFP gene.

B. Regeneration and Seed Production

Cells that survive the exposure to the selective agent, or cells that have been scored positive in a screening assay, may be cultured in media that supports regeneration of plants. In an exemplary embodiment, MS and N6 media may be modified by including further substances such as growth regulators. One such growth regulator is dicamba or 2,4-D. However, other growth regulators may be employed, including NAA, NAA+2,4-D or picloram. Media improvement in these and like ways has been found to facilitate the growth of cells at specific developmental stages. Tissue may be maintained on a basic media with growth regulators until sufficient tissue is available to begin plant regeneration efforts, or following repeated rounds of manual selection, until the morphology of the tissue is suitable for regeneration, at least 2 wk, then transferred to media conducive to maturation of embryoids. Cultures are transferred every 2 wk on this medium. Shoot development will signal the time to transfer to medium lacking growth regulators.

The transformed cells, identified by selection or screening and cultured in an appropriate medium that supports regeneration, will then be allowed to mature into plants. Developing plantlets are transferred to soiless plant growth mix, and hardened, e.g., in an environmentally controlled chamber, for example, at about 85% relative humidity, 600 ppm $CO_2$, and 25-250 microeinsteins $m^{-2}$ $s^{-1}$ of light. Plants are preferably matured either in a growth chamber or greenhouse. Plants can be regenerated from about 6 wk to 10 months after a transformant is identified, depending on the initial tissue. During regeneration, cells are grown on solid media in tissue culture vessels. Illustrative embodiments of such vessels are petri dishes and Plantcon™ containers (MP-ICN Biomedicals, Solon, Ohio, USA). Regenerating plants are preferably grown at about 19 to 28° C. After the regenerating plants have reached the stage of shoot and root development, they may be transferred to a greenhouse for further growth and testing.

Seeds on transformed plants may occasionally require embryo rescue due to cessation of seed development and premature senescence of plants. To rescue developing embryos, they are excised from surface-disinfected seeds 10-20 days post-pollination and cultured. An embodiment of media used for culture at this stage comprises MS salts, 2% sucrose, and 5.5 g/l agarose. In embryo rescue, large embryos (defined as greater than 3 mm in length) are germinated directly on an appropriate media. Embryos smaller than that may be cultured for 1 wk on media containing the above ingredients along with $10^{-5}$ M abscisic acid and then transferred to growth regulator-free medium for germination.

C. Characterization

To confirm the presence of the exogenous DNA or "transgene(s)" in the regenerating plants, a variety of assays may be performed. Such assays include, for example, "molecular biological" assays, such as Southern and northern blotting and PCR; "biochemical" assays, such as detecting the presence of a protein product, e.g., by immunological means (ELISAs and Western blots) or by enzymatic function; plant part assays, such as leaf or root assays; and also, by analyzing the phenotype of the whole regenerated plant.

D. DNA Integration, RNA Expression and Inheritance

Genomic DNA may be isolated from cell lines or any plant parts to determine the presence of the exogenous gene through the use of techniques well known to those skilled in the art. Note, that intact sequences will not always be present, presumably due to rearrangement or deletion of sequences in the cell. The presence of DNA elements introduced through the methods of this invention may be determined, for example, by polymerase chain reaction (PCR). Using this technique, discreet fragments of DNA are amplified and detected by gel electrophoresis. This type of analysis permits one to determine whether a gene is present in a stable transformant, but does not prove integration of the introduced gene into the host cell genome. It is typically the case, however, that DNA has been integrated into the genome of all transformants that demonstrate the presence of the gene through PCR analysis. In addition, it is not typically possible using PCR™ techniques to determine whether transformants have exogenous genes introduced into different sites in the genome, i.e., whether transformants are of independent origin. It is contemplated that using PCR techniques it would be possible to clone fragments of the host genomic DNA adjacent to an introduced gene.

Positive proof of DNA integration into the host genome and the independent identities of transformants may be determined using the technique of Southern hybridization. Using this technique specific DNA sequences that were introduced into the host genome and flanking host DNA sequences can be identified. Hence the Southern hybridization pattern of a given transformant serves as an identifying characteristic of that transformant. In addition it is possible through Southern hybridization to demonstrate the presence of introduced genes in high molecular weight DNA, i.e., confirm that the introduced gene has been integrated into the host cell genome. The technique of Southern hybridization provides information that is obtained using PCR, e.g., the presence of a gene, but also demonstrates integration into the genome and characterizes each individual transformant.

Whereas DNA analysis techniques may be conducted using DNA isolated from any part of a plant, RNA will only be expressed in particular cells or tissue types and hence it will be necessary to prepare RNA for analysis from these tissues. PCR techniques also may be used for detection and quantitation of RNA produced from introduced genes. In this application of PCR it is first necessary to reverse transcribe RNA into DNA, using enzymes such as reverse transcriptase, and then through the use of conventional PCR techniques amplify the DNA. In most instances PCR techniques, while useful, will not demonstrate integrity of the RNA product. Further information about the nature of the RNA product may be obtained by northern blotting. This technique will demonstrate the presence of an RNA species and give information about the integrity of that RNA. The presence or absence of an RNA species also can be determined using dot or slot blot northern hybridizations. These techniques are modifications of northern blotting and will only demonstrate the presence or absence of an RNA species.

E. Gene Expression

While Southern blotting and PCR may be used to detect the gene(s) in question, they do not provide information as to whether the corresponding protein is being expressed. Expression may be evaluated by determining expression via transcript-profiling techniques such as by use of a microarray, and by specifically identifying the protein products of the introduced genes or evaluating the phenotypic changes brought about by their expression.

Assays for the production and identification of specific proteins may make use of physical-chemical, structural, functional, or other properties of the proteins. Unique physical-chemical or structural properties allow the proteins to be separated and identified by electrophoretic procedures, such as native or denaturing gel electrophoresis or isoelectric focusing, or by chromatographic techniques such as ion exchange or gel exclusion chromatography. The unique structures of individual proteins offer opportunities for use of specific antibodies to detect their presence in formats such as an ELISA assay. Combinations of approaches may be employed with even greater specificity such as western blotting in which antibodies are used to locate individual gene products that have been separated by electrophoretic techniques. Additional techniques may be employed to absolutely confirm the identity of the product of interest such as evaluation by amino acid sequencing following purification. Although these are among the most commonly employed, other procedures may be additionally used.

Assay procedures also may be used to identify the expression of proteins by their functionality, especially the ability of enzymes to catalyze specific chemical reactions involving specific substrates and products. These reactions may be followed by providing and quantifying the loss of substrates or the generation of products of the reactions by physical or chemical procedures. Examples are as varied as the enzyme to be analyzed and may include assays for PAT enzymatic activity by following production of radiolabeled acetylated phosphinothricin from phosphinothricin and $^{14}$C-acetyl CoA or for anthranilate synthase activity by following loss of fluorescence of anthranilate, to name two.

Very frequently the expression of a gene product is determined by evaluating the phenotypic results of its expression. These assays also may take many forms including but not limited to analyzing changes in the chemical composition, morphology, or physiological properties of the plant. Chemical composition may be altered by expression of genes encoding enzymes or storage proteins which change amino acid composition and may be detected by amino acid analysis, or by enzymes which change starch quantity which may be analyzed by near infrared reflectance spectrometry. Morphological changes may include greater stature or thicker stalks. Most often changes in response of plants or plant parts to imposed treatments are evaluated under carefully controlled conditions termed bioassays.

VII. BREEDING PLANTS OF THE INVENTION

In addition to direct transformation of a particular plant genotype with a construct prepared according to the current invention, transgenic plants may be made by crossing a plant having a selected DNA of the invention to a second plant lacking the construct. For example, a selected CT biosynthesis gene can be introduced into a particular plant variety by crossing, without the need for ever directly transforming a plant of that given variety. Therefore, the current invention not only encompasses a plant directly transformed or regenerated from cells which have been transformed in accordance with the current invention, but also the progeny of such plants. As used herein the term "progeny" denotes the offspring of any generation of a parent plant prepared in accordance with the instant invention, wherein the progeny comprises a selected DNA construct prepared in accordance with the invention. "Crossing" a plant to provide a plant line having one or more added transgenes relative to a starting plant line, as disclosed herein, is defined as the techniques that result in a transgene of the invention being introduced into a plant line by crossing a starting line with a donor plant line that comprises a transgene of the invention. To achieve this one could, for example, perform the following steps:

(a) plant seeds of the first (starting line) and second (donor plant line that comprises a transgene of the invention) parent plants;

(b) grow the seeds of the first and second parent plants into plants that bear flowers;

(c) pollinate a flower from the first parent plant with pollen from the second parent plant; and (d) harvest seeds produced on the parent plant bearing the fertilized flower.

Backcrossing is herein defined as the process including the steps of:

(a) crossing a plant of a first genotype containing a desired gene, DNA sequence or element to a plant of a second genotype lacking the desired gene, DNA sequence or element;

(b) selecting one or more progeny plant containing the desired gene, DNA sequence or element;

(c) crossing the progeny plant to a plant of the second genotype; and (d) repeating steps (b) and (c) for the purpose of transferring a desired DNA sequence from a plant of a first genotype to a plant of a second genotype.

Introgression of a DNA element into a plant genotype is defined as the result of the process of backcross conversion. A plant genotype into which a DNA sequence has been introgressed may be referred to as a backcross converted genotype, line, inbred, or hybrid. Similarly a plant genotype lacking the desired DNA sequence may be referred to as an unconverted genotype, line, inbred, or hybrid.

VIII. DEFINITIONS

Expression: The combination of intracellular processes, including transcription and translation undergone by a coding DNA molecule such as a structural gene to produce a polypeptide.

Genetic Transformation: A process of introducing a DNA sequence or construct (e.g., a vector or expression cassette) into a cell or protoplast in which that exogenous DNA is incorporated into a chromosome or is capable of autonomous replication.

Heterologous: A sequence which is not normally present in a given host genome in the genetic context in which the sequence is currently found In this respect, the sequence may be native to the host genome, but be rearranged with respect to other genetic sequences within the host sequence. For example, a regulatory sequence may be heterologous in that it is linked to a different coding sequence relative to the native regulatory sequence.

Obtaining: When used in conjunction with a transgenic plant cell or transgenic plant, obtaining means either transforming a non-transgenic plant cell or plant to create the transgenic plant cell or plant, or planting transgenic plant seed to produce the transgenic plant cell or plant. Such a transgenic plant seed may be from an $R_0$ transgenic plant or may be from a progeny of any generation thereof that inherits a given transgenic sequence from a starting transgenic parent plant.

Proanthocyanidin (PA) biosynthesis gene: A gene encoding a polypeptide that catalyzes one or more steps in the biosynthesis of condensed tannins (proanthocyanidins).

Promoter: A recognition site on a DNA sequence or group of DNA sequences that provides an expression control element for a structural gene and to which RNA polymerase specifically binds and initiates RNA synthesis (transcription) of that gene.

$R_0$ transgenic plant: A plant that has been genetically transformed or has been regenerated from a plant cell or cells that have been genetically transformed.

Regeneration: The process of growing a plant from a plant cell (e.g., plant protoplast, callus or explant).

Selected DNA: A DNA segment which one desires to introduce into a plant genome by genetic transformation.

Transformation construct: A chimeric DNA molecule which is designed for introduction into a host genome by genetic transformation. Preferred transformation constructs will comprise all of the genetic elements necessary to direct the expression of one or more exogenous genes. In particular embodiments of the instant invention, it may be desirable to introduce a transformation construct into a host cell in the form of an expression cassette.

Transformed cell: A cell the DNA complement of which has been altered by the introduction of an exogenous DNA molecule into that cell.

Transgene: A segment of DNA which has been incorporated into a host genome or is capable of autonomous replication in a host cell and is capable of causing the expression of one or more coding sequences. Exemplary transgenes will provide the host cell, or plants regenerated therefrom, with a novel phenotype relative to the corresponding non-transformed cell or plant. Transgenes may be directly introduced into a plant by genetic transformation, or may be inherited from a plant of any previous generation which was transformed with the DNA segment.

Transgenic plant: A plant or progeny plant of any subsequent generation derived therefrom, wherein the DNA of the plant or progeny thereof contains an introduced exogenous DNA segment not naturally present in a non-transgenic plant of the same strain. The transgenic plant may additionally contain sequences which are native to the plant being transformed, but wherein the "exogenous" gene has been altered in order to alter the level or pattern of expression of the gene, for example, by use of one or more heterologous regulatory or other elements.

Vector: A DNA molecule capable of replication in a host cell and/or to which another DNA segment can be operatively linked so as to bring about replication of the attached segment. A plasmid is an exemplary vector.

IX. EXAMPLES

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

Example 1

Production and Analysis of Transformed *Medicago* Hairy Roots

Either pSB239, containing the ORF of *Arabidopsis TT2* (e.g., SEQ ID NO:23) driven by the double 35S CaMV promoter (Sharma and Dixon, 2005), or empty vector pCAMBIA2300, for controls, were transformed into *Agrobacterium rhizogenes* strain ARqual1 (Quandt et al., 1993) using the freezing-thaw method (Chen et al., 1994). Transformed colonies containing one or the other of these plasmids were grown on LB-agar medium with selection at 28° C. for 2 days, then used to inoculate radicles of *M. truncatula* (cv. Jemalong A17) seedlings (Limpens et al., 2004). The resulting hairy roots were maintained on B5 agar media in Petri dishes supplied with 50 mg/l kanamycin under fluorescent light (140 $\mu E/m^2 s^1$) with a 16 h photoperiod, and were subcultured every month onto fresh media.

Screening of hairy root clones by RT-PCR, and by staining with DMACA reagent for the presence of PAs, was performed by isolating total RNA extracted from 15 independent 172-transformed and two empty vector control hairy root lines with Tri-reagent (Gibco-BRL Life Technologies, Gaithersburg, Md.), and 4 μg of total RNA for each sample was used for cDNA synthesis with Superscript III reverse transcriptase (Invitrogen, Carlsbad, Calif.). Two μl of the cDNA was then amplified using Ex taq (Takara, Shiga, Japan) in a total volume of 20 μl. Primers and PCR conditions for amplification of AtTT2, MtANR and actin genes, and other PA biosynthesis related sequences, were as described previously (Sharma and Dixon, 2005 (SEQ ID NOs:39-66). PCR products were analyzed by electrophoresis of 15 μl aliquots on 1.0% agarose gels in Tris-acetic acid—EDTA buffer and visualized with ethidium bromide. PCR-positive hairy roots were stained with 0.1% DMACA in methanol: 6N HCl (1:1) for 20 min, and then washed in ethanol: acetic acid (75:25) for detection of PAs.

Figure 1B:
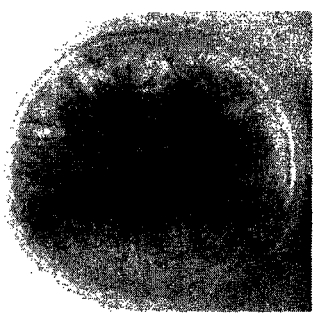
Figure 1C:
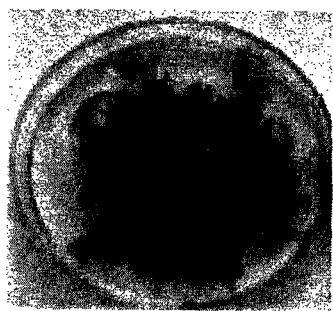
Figure 1D:
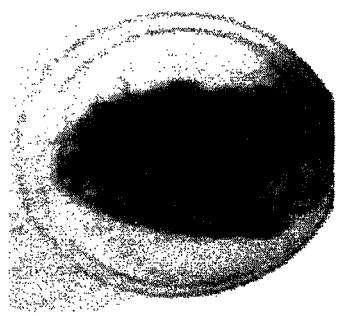

TT2-expressing hairy roots were phenotypically identical to empty vector controls, exhibiting a strong, reddish purple pigmentation (FIG. 1A). However, when stained with dimethylaminocinnamaldehyde (DMACA) reagent, the TT2-expressing lines, but not the vector controls, turned an intense blue-green color (FIG. 1B,C), indicative of the presence of PA polymers, oligomers, or precursor flavan-3-ols (Treutter, 1989).

Soluble PA content was analyzed by normal phase HPLC coupled with post-column derivatization with DMACA reagent (0.2% w/v DMACA in methanol-3N HCl) at 640 nm, with (+)-catechin as standard (Peel and Dixon, 2007).

For quantification of insoluble PAs, 1 ml of butanol-HCl reagent was added to the dried residues and the mixtures sonicated at room temperature for 1 hour, followed by centrifugation at 2,500 g for 10 min. The absorption of the supernatants was measured at 550 nm; the samples were then boiled for 1 hour, cooled to room temperature, and the absorbance at 550 nm recorded again, with the first value being subtracted from the second. Absorbance values were converted into PA equivalents using a standard curve of procyanidin B1 (Indofine, Hillsborough N.J., USA). The hydrolyzates were then subjected to reverse phase HPLC analysis to determine which anthocyanidins had been formed.

For extraction of anthocyanins, 5 ml methanol: 0.1% HCl was added to 0.5 g ground samples and the mixtures sonicated for 1 hour and then shaken overnight at 120 rpm. Following centrifugation at 2,500 g for 10 min, 1 ml of water was added to 1 ml of extract followed by 1 ml of chloroform to remove chlorophyll, and the absorption of the aqueous phase recorded at 530 nm. Total anthocyanin content was calculated based on the molar absorbance of cyanidin-3-β-glucoside. For hydrolysis of anthocyanins, the method described below for flavonoids was used.

For determination of total flavonoids, 0.1 g batches of ground samples were extracted with 3 ml 80% methanol, sonicated for 1 hour, and then kept at 4° C. overnight. The extract was centrifuged to remove tissue debris and the supernatant dried under nitrogen, followed by acid hydrolysis with 3 ml of 1 N HCl at 90° C. for 2 hours. After extracting twice with 3 ml of ethyl acetate, the supernatant was pooled, dried under nitrogen and resuspended in 200 μl of methanol. Forty μl of the methanolic solution was used for reverse phase HPLC analysis.

All reverse-phase HPLC analyses were performed on an Agilent HP1100 HPLC using the following gradient: solvent A (1% phosphoric acid) and B (acetonitrile) at 1 ml/min flow rate: 0-5 min, 5% B; 5-10 min, 5-10% B; 10-25 min, 10-17% B; 25-30 min, 17-23% B; 30-65 min, 23-50% B; 65-79 min, 50-100% B; 79-80 min, 100-5% B. Data were collected at 254 and 530 nm for flavonoids and anthocyanidins, respectively. Identifications were based on chromatographic behavior and UV spectra compared with those of authentic standards.

Figure 2A:
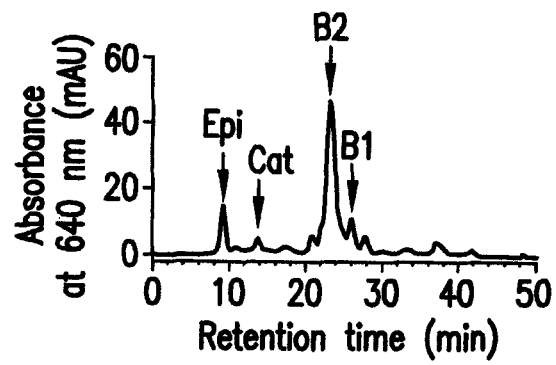
FIG. 2A-F: PA content and composition in *M. truncatula* hairy roots. (A) The soluble PA fraction from TT2-expressing line 239-5 analyzed by normal phase HPLC with post-column derivatization. (B) As above, for control line 2300-11. Letters indicate the retention times of authentic standards of (−)-epicatechin (Epi), (+)-catechin (Cat), procyanidin B1 (B1) and procyanidin B2 (B2). (C) Dried residues from line 239-5 (1,3) and 2300-11 (2,4) before (left) and after (right) hydrolysis in acid-butanol. (D) HPLC chromatograph of acid-butanol hydrolyzed products from a TT2-expressing line. (E) as above, from a vector control line. Letters indicate retention times of authentic anthocyanidin standards; De, delphinidin; Cy, cyanidin; Pe, pelargonidin. (F) Levels of total soluble (shaded bars) and insoluble (open bars) PAs in duplicate TT2-expressing and empty vector lines.
Figure 2B:
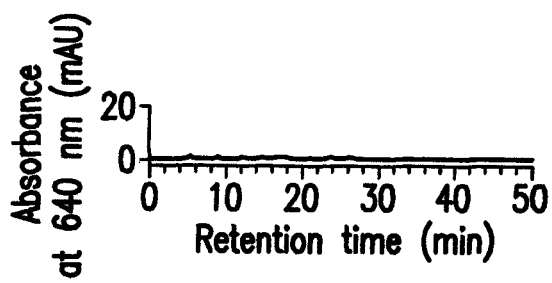
Figure 2C:
Figure 2D:
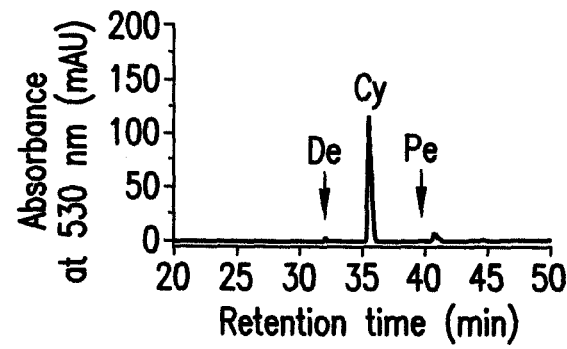
Figure 2E:
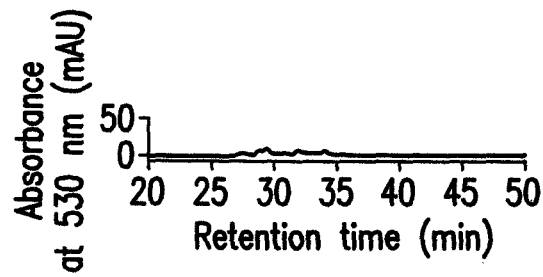
Figure 2F:
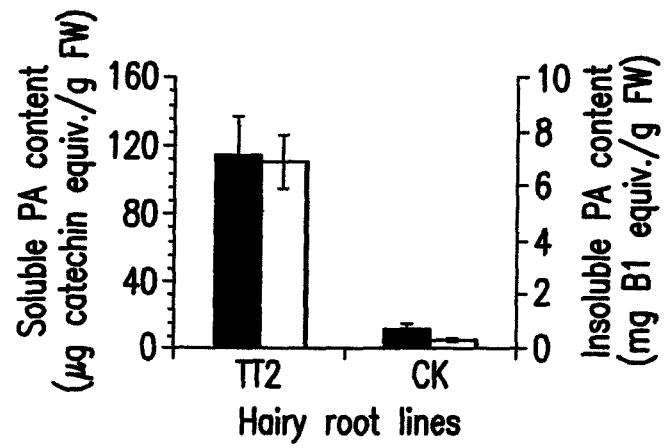

No signal was observed following separation of extracts from control roots (FIG. 2B). The soluble PA fraction from the TT2-expressing line 239-5 contained monomers, dimers, and a range of oligomers with an estimated degree of polymerization of up to 10 (FIG. 2A), based on calibration of the HPLC column with PA size standards (Peel and Dixon, 2007). Epicatechin monomer and a compound with the same retention time as procyanidin B2 (epicatechin-(4β→8)-epicatechin) were among the major soluble components. The average soluble PA content in two independent TT2-expressing lines was more than ten times the level in the control lines (FIG. 2F).

Flavonoids from other organs of *M. truncatula* were also extracted and analyzed by HPLC-MS/MS. Samples of root, stem, leaf, flower, seed coat and whole seed at six different time points (10, 12, 16, 20, 24 and 36 days after pollination [dap]) were prepared as previously reported (Pang et al., 2007). Triplicate samples (around 100 mg each) were extracted in 2 ml of acetonitrile/water (75:25). The samples were sonicated at room temperature for 30 min and 50 nmol of the C-glycoyl isoflavone puerarin were added as internal standard for extraction efficiency. Following centrifugation, the residues were re-extracted at 4° C. overnight, the two extracts pooled, concentrated under nitrogen gas, further lyophilized, and finally re-suspended in 500 μl of methanol. For hydrolysis of glycosides, 150 μl of sample was dried and 2 ml of 5 mg/ml almond β-glucosidase (Sigma, St Louis, Mo.) in citric acid buffer (pH 5.5) was added and the mixtures incubated at 37° C. overnight. The samples were then extracted twice with 1 ml of ethyl acetate, and the extracts pooled, dried again under nitrogen gas, and dissolved in 100 μl methanol. Thirty μl aliquots of the above samples were loaded on an Agilent 1100 series II HPLC system coupled with a Bruker Esquire ion-trap mass spectrometer via electrospray ionization. HPLC separation was achieved using a reverse phase, $C_{18}$, 5 μm, 4.6×250 mm column (J. T. Baker, Phillipsburg, N.J.) and elution with solvent A (acetonitrile/water [95:5, v/v, 0.1% acetic acid]) and solvent B (acetonitrile/water [95:5, v/v, 0.1% acetic acid]) with a linear gradient of 5-95% solvent B over 65 min at a rate of 0.8 ml/min. Relative analyte levels were determined from HPLC-MS peak areas normalized to the peak area of the puerarin internal standard. Epicatechin glucoside was identified from its mass fragment pattern, UV spectrum, and production of epicatechin aglycone after enzymatic hydrolysis.

Example 2

TT2 Induces PA Accumulation in *Medicago* Hairy Roots

Butanol-HCl hydrolysis of the insoluble cell residue fraction from the TT2-expressing lines led to a massive release of colored anthocyanidins (FIG. 2C), shown by HPLC analysis to consist largely of cyanidin (FIG. 2D) which originates from epicatechin and/or catechin extension units in PAs. Very little anthocyanidin was released from the insoluble residue from empty vector control lines (FIG. 2C,E). The average level of insoluble PAs in two independent TT2-expressing lines was more than 24-fold higher than in the empty vector control lines (FIG. 2F) and more than 50-fold higher than the level of soluble PAs produced in response to expression of TT2. The overall PA level of TT2-expressing roots was higher than found naturally in the seed coat of *M. truncatula* (Pang et al., 2007).

Figure 8A:
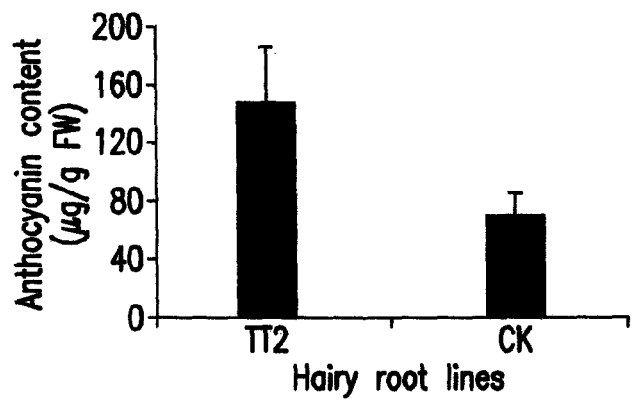
FIG. 8A-D: Anthocyanin content and composition of *M. truncatula* hairy roots. (A) Spectrophotometrically determined anthocyanin levels in empty vector and TT2-expressing hairy roots. (B) HPLC chromatograph of unhydrolyzed anthocyanins from a TT2-expressing line. (C) HPLC chromatograph of anthocyanidin standards; D, delphinidin; C, cyanidin; P, pelargonidin. (D) HPLC chromatograph of acid-hydrolyzed anthocyanins from a TT2-expressing line. Arrows in A indicate positions of anthocyanidin glycosides.
Figure 8B:
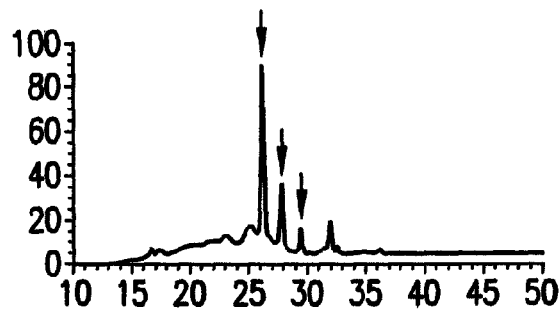
Figure 8C:
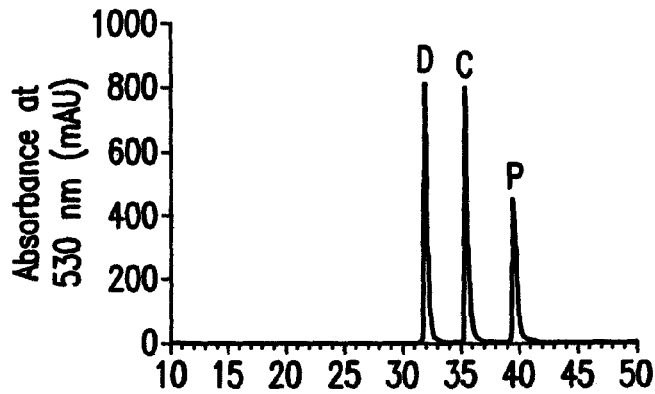
Figure 8D:
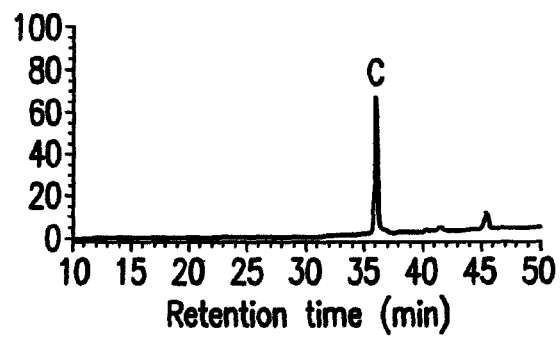
Figure 9A:
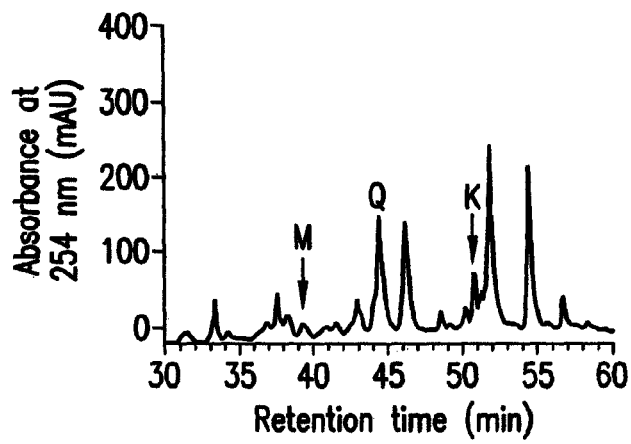
FIG. 9A-D: Flavonol composition of *M. truncatula* hairy roots. (A) HPLC chromatograph of flavonoids from a TT2-expressing line. (B) HPLC chromatograph of flavonol standards; M, myricetin; Q, quercetin; K, kaempferol. (C) HPLC chromatograph of flavonoids from an empty vector control line. Compounds with the same retention times and UV spectra as M, Q and K were not detected. (D) Flavonol content of TT2-expressing lines. Data show means and standard deviations from duplicate analyses of two independent transgenic lines (biological replicates).
Figure 9B:
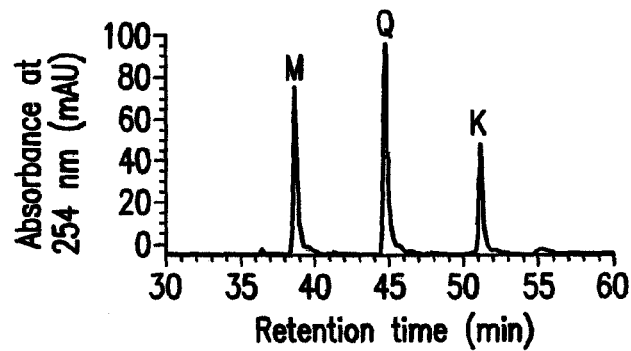
Figure 9C:
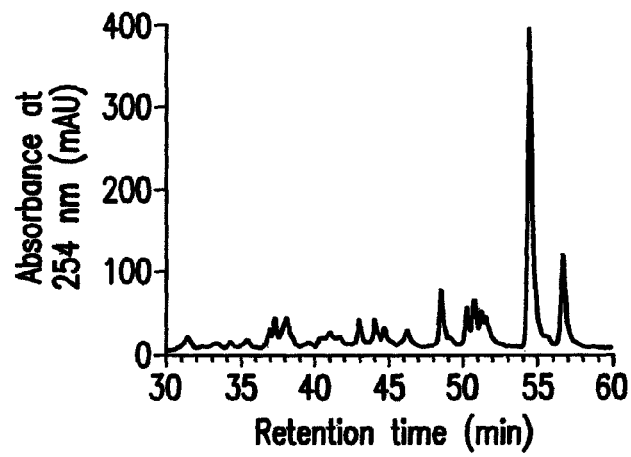
Figure 9D:
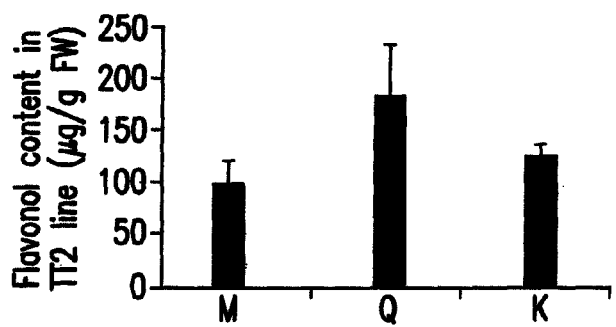

TT2 also induces anthocyanin and flavonol biosynthesis in *Medicago*. TT2, in conjunction with two other transcription factors, TT8 and TRANSPARENT TESTA GLABRA 1 (TTG1), controls the PA-specific branch of the flavonoid pathway in the *Arabidopsis* seed coat (Nesi et al., 2001; Baudry et al., 2004), whereas other transcription factors control anthocyanin and flavonol accumulation (Lepiniec et al., 2006). Empty vector-transformed *Medicago* hairy roots contained a significant level of anthocyanins as determined by spectrophotometric analysis, but this amount was approximately double in lines expressing 172 (FIG. 8A). HPLC analysis of line 239-5 revealed the presence of multiple anthocyanin peaks (FIG. 8B), all of which disappeared after acid hydrolysis and were converted predominantly to cyanidin (FIG. 8C,D), the precursor for both anthocyanins and (−)-epicatechin units in PAs. HPLC analysis also revealed the presence of flavonols, particularly quercetin, in TT2-expressing but not in control roots (FIG. 9).

Example 3

Genes Induced by Ectopic Expression of TT2 in *Medicago* Hairy Roots

Figure 3A:
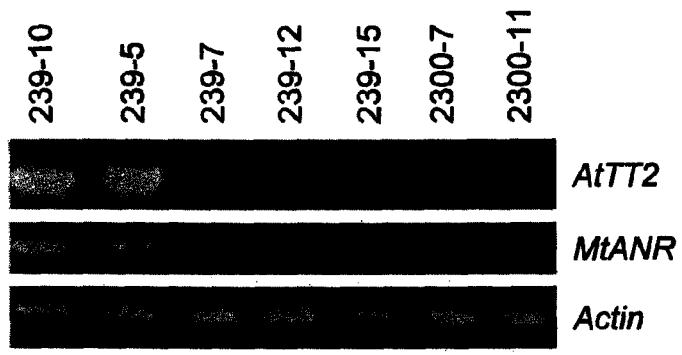
FIG. 3A-C: Transcripts induced in *M. truncatula* hairy roots by expression of 172, or expressed in the *M. truncatula* seed coat. (A) RT-PCR screen of individual hairy root lines for expression of the TT2 transgene and endogenous ANR transcripts. Actin was used as loading control. (B) Scatter plots of gene expression level differences between TT2-expressing and control lines from Affymetrix microarray analysis. (C) Venn diagram showing overlap between probe sets induced by TT2 in hairy roots and expressed preferentially in the seed coat. a, Number of probe sets up-regulated by TT2; b, number of probe sets preferentially expressed in seed coat; c, intersection of a and b.

TT2 is necessary for transcriptional activation of anthocyanidin reductase (ANR; FIG. 7) in *Arabidopsis* (Baudry et al., 2004). A preliminary screen of transgenic hairy roots by RT-PCR indicated that lines positive for 172 expression also exhibited high levels of ANR transcripts, but ANR transcripts were not detected in empty vector control lines (FIG. 3A).

Figure 3B:
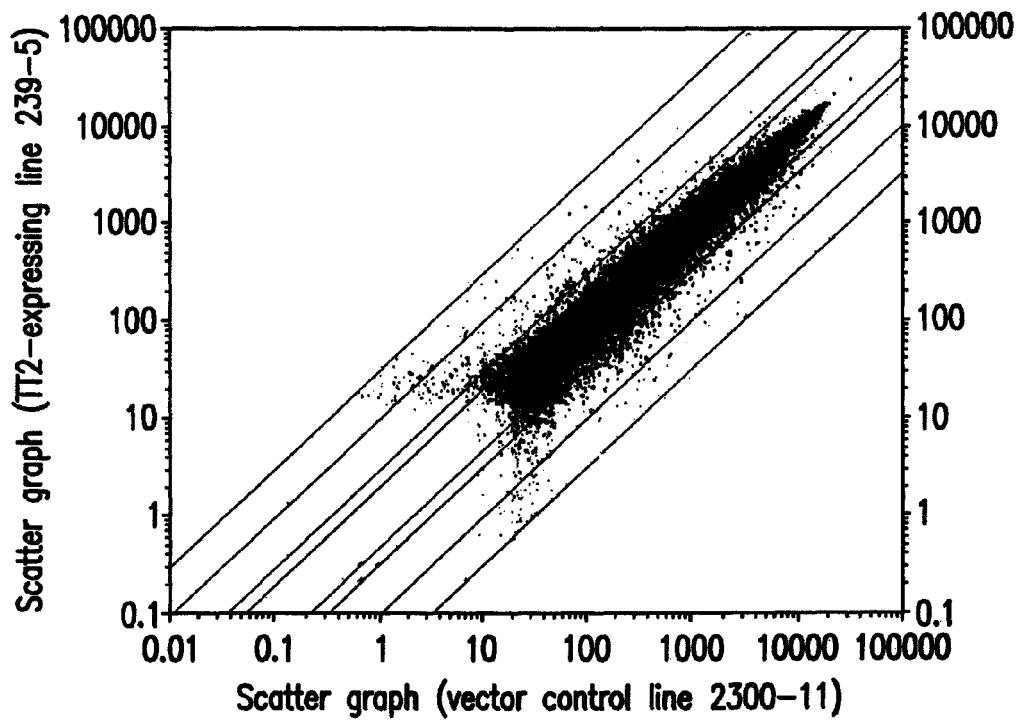
Figure 10A:
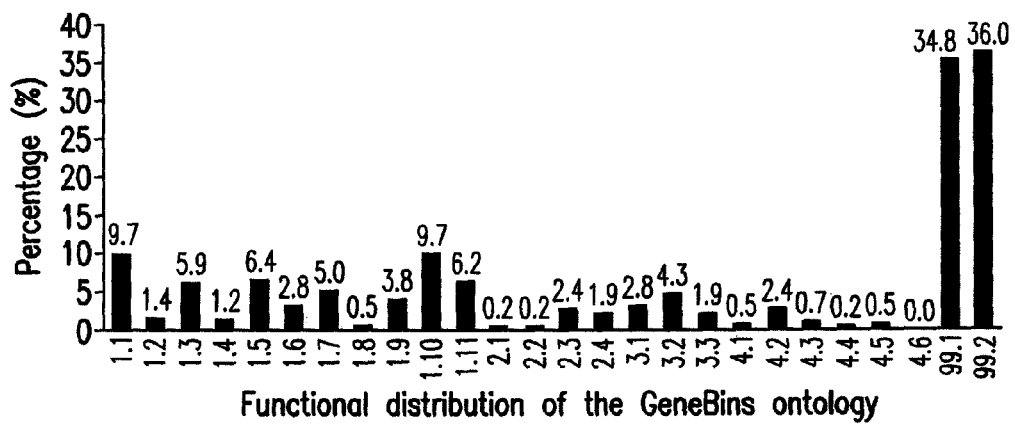
FIG. 10A-B: Bar charts showing GO (Gene Ontology) annotations. (A) *M. truncatula* probe sets up-regulated (from 2- to 500-fold change) as a result of TT2 expression. (B) Probe sets expressed preferentially in *M. truncatula* seed coats. A description of the GO terms can be found at www-.bioinfoserver.rsbs.anu.edu.au/utils/GeneBins/ (Goffard and Weiller, 2007).

Total RNA samples from duplicate biological replicates of TT2-expressing and empty vector controls were subjected to Affymetrix GeneChip® microarray analysis. Changes in expression level of all probe sets on the chip are shown in FIG. 3B. Four hundred and twenty two probe sets were up-regulated in the TT2-expressing lines and 344 were down-regulated (Selected probes shown in Table 1. Probe set sequences of Table 1 are available from Affymetrix (www.affymetrix.com/support/technical/byproduct.affx?product=medicago). The Gene Ontology (GO) classifications of the up-regulated probe sets are summarized in FIG. 10A.

Of the 30 probe sets up-regulated more than 10-fold (Table 1), 7 represented genes with unknown function. ANR was the most strikingly induced gene (473-times the expression level in the empty vector control line). A number of other flavonoid pathway genes required for PA biosynthesis were also up-regulated more than 2-fold in the TT2-expressing lines (Table 2), including encoding anthocyanidin synthase and leucoanthocyanidin reductase, which converts leucocyanidin to (+)-catechin (FIG. 7). The exact mechanism(s) for transport of PA monomer units to the vacuole are at present uncertain, but could involve transport of glycosylated intermediates through a MATE proton antiport system (Debeaujon et al., 2001), uptake via a GST-linked system as previously implicated in anthocyanin transport (Kitamura et al., 2004; Mueller et al., 2000), or transport through the cytosol in membrane vesicles, as suggested for anthocyanins (Grotewold, 2004) and deoxyanthocyanidins (Snyder and Nicholson, 1990). Consistent with the increase in flavonols in the hairy roots, flavonol synthase transcripts were induced 16.6-fold. In Tables 1-3 the expression values were obtained from RMA (Irizarry et al., 2003). The P-Value was obtained using Associative Analysis (Dozmorov and Centola, 2003). The Q-Value was obtained using EDGE (Leek et al., 2006).

TABLE 1

The probe sets that were more than 10 fold up-regulated by TT2 in *M. truncatula* hairy roots.

| Probe sets | Annotation | Ratio (TT2/CK) | P-Value* | Q-Value** |
|---|---|---|---|---|
| Mtr.44985.1.S1_at | Anthocyanidin reductase, complete | 473.3 | 0.00003 | 0.05024 |
| Mtr.21996.1.S1_x_at | Weakly similar to glucosyltransferase-13 (Fragment) | 64.8 | 0.00029 | 0.06699 |
| Mtr.41147.1.S1_at | Unknown | 63.5 | 0.00068 | 0.08141 |
| Mtr.47691.1.S1_at | Unknown | 29.5 | 0.00081 | 0.08448 |
| Mtr.10917.1.S1_at | Cytochrome P450 77A3, partial (95%) | 25.6 | 0.00015 | 0.06019 |
| Mtr.4369.1.S1_at | Similar to At2g41420, partial (90%) | 25.2 | 0.00112 | 0.08818 |
| Mtr.47777.1.S1_at | Weakly similar to UP|O81190 (O81190) putative transposase | 23.9 | 0.00693 | 0.11234 |
| Mtr.47631.1.S1_s_at | Weakly similar to UP|Q5UDR1 (Q5UDR1) transposase, partial (37%) | 23.5 | 0.00123 | 0.08818 |
| Mtr.52009.1.S1_s_at | Putative BED Finger; HAT dimerisation; immunoglobulin major histocompatibility complex | 20.4 | 0.00219 | 0.09470 |
| Mtr.50650.1.S1_s_at | Plant MUDR transposase; SWIM Zn-finger, Zn-finger, CCHC Type | 19.9 | 0.02058 | 0.13148 |
| Mtr.23138.1.S1_s_at | Weakly similar to MUDR family transposase protein, partial (61%) | 18.6 | 0.00029 | 0.06699 |
| Mtr.9658.1.S1_at | Unknown | 18.1 | 0.00013 | 0.05831 |
| Mtr.11000.1.S1_at | Unknown | 17.2 | 0.00533 | 0.10722 |
| Mtr.14017.1.S1_at | Similar to Flavonol Synthase (FLS), partial (19%) | 16.6 | 0.00539 | 0.10735 |
| Mtr.39235.1.S1_at | Similar to AT4g28740 F16A16_150, partial (18%) | 16.6 | 0.00595 | 0.10923 |
| Mtr.38712.1.S1_at | Similar to AT4g28740 F16A16_150, partial (23%) | 16.4 | 0.00730 | 0.11356 |
| Mtr.7974.1.S1_at | Unknown | 16.1 | 0.00032 | 0.06896 |
| Mtr.17084.1.S1_at | LQGC hypothetical protein | 16.0 | 0.00252 | 0.09579 |
| Mtr.18767.1.S1_at | Hypothetical protein | 15.9 | 0.00061 | 0.08114 |
| Mtr.45980.1.S1_at | LQGC hypothetical protein | 15.4 | 0.00011 | 0.05609 |
| Mtr.36851.1.S1_at | Unknown | 14.9 | 0.00353 | 0.10103 |
| Mtr.32890.1.S1_at | Similar to UP|Q6NV39 (Q6NV39) Zgc: 85612, partial (2%) | 14.2 | 0.00178 | 0.09131 |
| Mtr.16495.1.S1_at | Cyclin-like F-box | 12.1 | 0.00009 | 0.05481 |
| Mtr.17982.1.S1_s_at | Hypothetical protein | 11.9 | 0.01932 | 0.13060 |
| Mtr.25016.1.S1_at | Unknown | 11.7 | 0.01440 | 0.12507 |
| Mtr.6531.1.S1_at | Similar to UP|PGS1_XENLA (Q9IB75) biglycan precursor, partial (3%) | 11.5 | 0.01231 | 0.12194 |

TABLE 1-continued

The probe sets that were more than 10 fold up-regulated by TT2 in *M. truncatula* hairy roots.

| Probe sets | Annotation | Ratio (TT2/CK) | P-Value* | Q-Value** |
|---|---|---|---|---|
| Mtr.51818.1.S1_at | Predicted protein | 11.4 | 0.00003 | 0.05024 |
| Mtr.28306.1.S1_at | Weakly similar to (GPI-anchored protein) (At5g63500), complete | 10.5 | 0.03016 | 0.14094 |
| Mtr.33218.1.S1_at | Similar to F14N23.12 (At1g10240 F14N23_12), partial (4%) | 10.4 | 0.01317 | 0.12292 |
| Mtr.18503.1.S1_s_at | LQGC hypothetical protein | 10.0 | 0.00778 | 0.11485 |

Note:
Expression values were obtained from RMA (Irizarry et al., 2003);
*The P-Value was obtained using Associative Analysis (Dozmorov and Centola, 2003);
*The Q-Value was obtained using EDGE (Leek et al, 2006).

TABLE 2

Flavonoid pathway gene probe sets that were up-regulated more than 2-fold by TT2 in *M. truncatula* hairy root.

| Pathway genes | Annotations | Ratio (TT2/CK) | Probe sets | P-Value* | Q-Value** |
|---|---|---|---|---|---|
| PAL | Phenylalanine ammonia-lyase | 2.7 | Mtr.51909.1.S1_at | 0.00000 | 0.07908 |
| 4CL | Similar to 4-coumarate-CoA ligase-like protein, partial (29%) | 3.3 | Mtr.13904.1.S1_at | 0.00000 | 0.10670 |
| CHS | Type III polyketide synthase; Naringenin-chalcone synthase | 4.7 | Mtr.20567.1.S1_at | 0.00000 | 0.06312 |
| | Naringenin-chalcone synthase; Type III polyketide synthase | 2.2 | Mtr.14428.1.S1_at | 0.00000 | 0.13840 |
| CHI | Similar to chalcone-flavonone isomerase, partial (58%) | 2.8 | Mtr.8555.1.S1_at | 0.00000 | 0.09561 |
| F3H | Flavanone 3-hydroxylase | 2.3 | Mtr.49421.1.S1_at | 0.00000 | 0.06661 |
| F3'H | Similar to Gray pubescence flavonoid 3'-hydroxylase, partial (49%) | 2.6 | Mtr.6517.1.S1_at | 0.00000 | 0.07466 |
| | Similar to Flavonoid 3'-hydroxylase (fragment), partial (21%) | 2.2 | Mtr.36333.1.S1_at | 0.00000 | 0.06593 |
| F3'5'H | Similar to Flavonoid 3',5'-hydroxylase, partial (36%) | 2.3 | Mtr.29340.1.S1_at | 0.00000 | 0.14282 |
| FLS* | Flavonol synthase (FLS), partial (47%) | 16.6 | Mtr.14017.1.S1_at | 0.00000 | 0.10735 |
| DFR | Dihydroflavanol-4-reductase 1 (DFR1), complete | 2.0 | Mtr.38073.1.S1_at | 0.00000 | 0.05831 |
| LAR | Leucoanthocyanidin reductase (LAR) | 2.0 | Mtr.20055.1.S1_at | 0.00000 | 0.19692 |
| ANS | Similar to Anthocyanidin synthase, partial (53%) | 2.2 | Mtr.28774.1.S1_at | 0.00000 | 0.09943 |
| ANR | Anthocyanidin reductase, complete | 473.3 | Mtr.44985.1.S1_at | 0.00000 | 0.05024 |
| | Anthocyanidin reductase, partial (13%) | 4.5 | Mtr.7129.1.S1_at | 0.00000 | 0.12056 |
| TT8 | Weakly similar to symbiotic ammonium transporter (similar to TT8) | 2.3 | Mtr.253.1.S1_at | 0.00000 | 0.10860 |
| | Weakly similar to Anthocyanin 1 | 2.1 | Mtr.22479.1.S1_at | 0.00000 | 0.10969 |
| TTG1 | Similar to WD-repeat protein GhTTG1, partial (8%) | 2.3 | Mtr.31614.1.S1_at | 0.00000 | 0.12023 |
| | Homologue To TTG1-like protein, partial (46%) | 2.3 | Mtr.39774.1.S1_at | 0.00000 | 0.10093 |
| GTs | Weakly similar to glucosyltransferase-13 (fragment) | 64.8 | Mtr.21996.1.S1_at | 0.00000 | 0.06699 |
| | Similar to glucosyltransferase-13 (fragment) | 9.0 | Mtr.24410.1.S1_at | 0.00000 | 0.09408 |
| | Weakly similar to UDP-glycosyltransferase 85A8, partial (27%) | 2.3 | Mtr.10553.1.S1_at | 0.00000 | 0.11709 |
| | Weakly similar to UDP Rhamnose-anthocyanidin-3-glucoside rhamnosyltransferase-like protein, partial (17%) | 2.1 | Mtr.31819.1.S1_at | 0.00000 | 0.13489 |
| | Similar to glucosyltransferase-9, partial (70%) | 2.1 | Mtr.44505.1.S1_at | 0.00000 | 0.12275 |
| | Weakly similar to limonoid UDP-glucosyltransferase (LGTase), partial (32%) | 6.3 | Mtr.45072.1.S1_at | 0.00000 | 0.10923 |

Note:
Expression values were obtained from RMA (12);
*P-Values were obtained using Associative Analysis (13);
*Q-Values were obtained using EDGE (14)

Two putative homologs of TT8, which encodes a bHLH protein involved in PA biosynthesis (Nesi et al., 2000) were up-regulated by 2.0 and 2.3-fold, and a homolog of *Arabidopsis* TTG1, a WD40 repeat protein that regulates trichome differentiation and anthocyanin biosynthesis in *Arabidopsis* (Zhang et al., 2003), was also induced by 2.3-fold (SI Table 2). Several probe sets with weak sequence similarity to the *Arabidopsis* transporters 1712 and TT19 (Debeaujon et al., 2001; Kitamura et al., 2004), and the proton translocating ATPase AHA 10 necessary for PA biosynthesis (Baxter et al., 2005), were weakly up-regulated by expression of TT2 (Table 3).

TABLE 3

Expression of *Medicago* genes with sequence similarity to genes implicated in PA precursor transport in *Arabidopsis*.

| Homologous genes | Probe set | Target Description | a | b | P-Value* | Q-Value** |
|---|---|---|---|---|---|---|
| AHA10 | Mtr.38588.1.S1_at | Homologue to plasma membrane H(+)-ATPase H+ transporting ATPase, proton pump; plasma-membrane proton-efflux | 0.50 | 0.005 | 0.014804 | 0.125983 |
| | Mtr.18921.1.S1_at | P-type ATPase | 2.01 | 0.460 | 0.005924 | 0.109227 |
| | Mtr.48295.1.S1_at | H+-ATPase, complete | 0.98 | 0.040 | 0.829199 | 0.294623 |
| TT12 | Mtr.51063.1.S1_at | Multi antimicrobial extrusion protein MatE | 0.91 | 0.076 | 0.135239 | 0.191304 |
| | Mtr.19280.1.S1_at | Multi antimicrobial extrusion protein MatE | 1.53 | 2.165 | 0.039389 | 0.148345 |
| | Mtr.26397.1.S1_s_at | MATE efflux family protein or similar to ripening regulated protein | 0.99 | 0.013 | 0.988887 | 0.325827 |

TABLE 3-continued

Expression of *Medicago* genes with sequence similarity to genes implicated in PA precursor transport in *Arabidopsis*.

| Homologous genes | Probe set | Target Description | a | b | P-Value* | Q-Value** |
|---|---|---|---|---|---|---|
| TT19 | Mtr.51063.1.S1_at | Weakly similar to Glutathione S-transferase | 1.35 | 0.004 | 0.001034 | 0.086787 |
|  | Mtr.12409.1.S1_at | Similar to Glutathione S-transferase GST22 (Fragment), complete | 1.01 | 0.936 | 0.600096 | 0.272047 |
|  | Mtr.12513.1.S1_at | Similar to Glutathione S-transferase GST24, partial (98%) | 0.89 | 0.005 | 0.236036 | 0.216562 | a = fold up-regulated by TT2 versus control;
b = fold preferentially expressed in seed coat versus non-seed tissues;
Note:
Expression values were obtained from RMA (12);
*P-Values were obtained using Associative Analysis (13)
*Q-Values was obtained using EDGE (14).

Example 4

Genes Preferentially Expressed in the *Medicago* Seed Coat

Figure 3C:
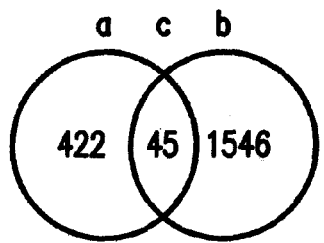
Figure 10B:
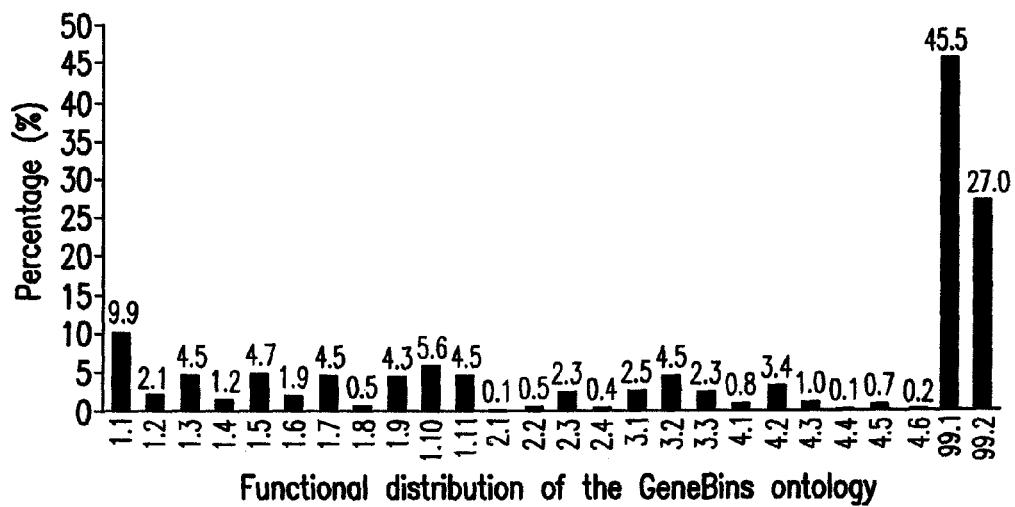

Ectopic, high level expression of transcription factors can result in artifactual pleiotropic effects (Broun, 2004). We therefore further interrogated TT2-induced genes for preferential expression in the seed coat, the natural site of PA biosynthesis in *Medicago* (Pang et al., 2007). Coats were dissected from developing seeds (from 16-24 days after pollination [dap]) and total RNA from pooled material analyzed by hybridization to Affymetrix arrays. A total of 1,546 gene probe sets were expressed in the seed coat at a level at least twice that in any other organ, and their Gene Ontology classifications are summarized in FIG. 10B. The gene with the highest seed coat specificity was a putative legumin J precursor (Table 4). Among the seed coat preferentially expressed genes, 45 probe sets were also up-regulated more than 2-fold by TT2 expression (FIG. 3C).

TABLE 4

The top 30 probe sets with preferential expression in the *Medicago* seed coat.

Figure 4A:
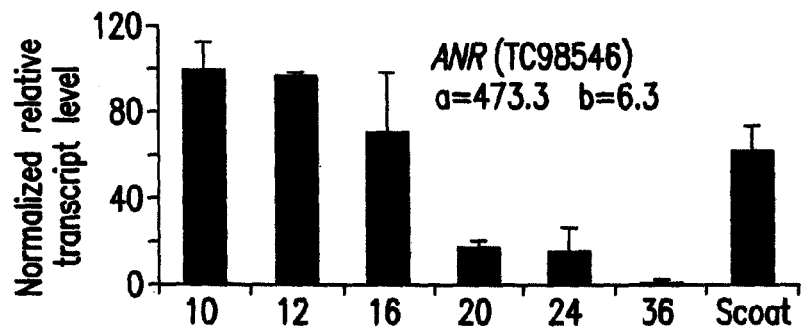
FIG. 4A-H: Transcript levels of selected genes during *M. truncatula* seed development and in different organs as determined by microarray analysis. (A-G) Normalized relative transcript levels of indicated genes during seed development. Numbers on the x axes represent days after pollination. (H) Relative transcript level of UGT72L1 in different organs. a=fold up-regulated by TT2 versus control; b=fold preferentially expressed in seed coat versus non-seed organs.
Figure 4B:
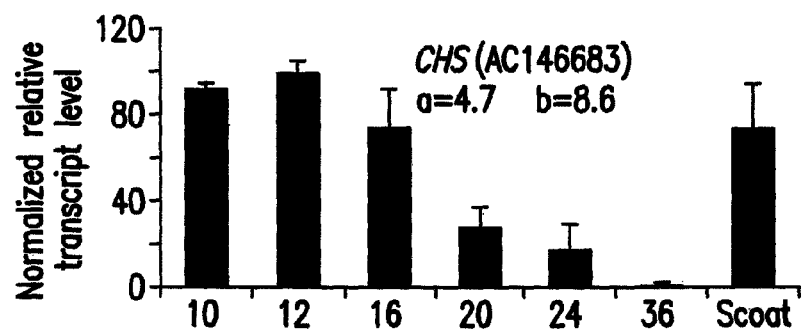
Figure 4C:
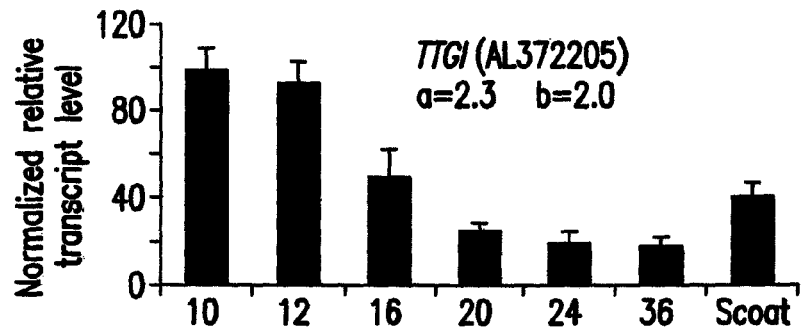

| Probe set | Target Description | a | b | c |
|---|---|---|---|---|
| Mtr.8458.1.S1_at | Legumin J precursor, Legumin J beta chain, partial (74%) | 18771.54 | 11.12 | 1688.48 |
| Mtr.8458.1.S1_x_at | Similar to Legumin J precursor, Legumin J beta chain, partial (74%) | 18356.45 | 11.09 | 1654.52 |
| Mtr.43563.1.S1_at | Weakly similar Lipid transfer protein, partial (25%) | 18507.38 | 11.81 | 1567.50 |
| Mtr.12611.1.S1_at | Unknown | 16611.42 | 10.71 | 1550.80 |
| Mtr.43910.1.S1_at | Unknown | 16110.70 | 11.66 | 1382.09 |
| Mtr.42662.1.S1_s_at | Similar to Subtilisin-type protease, partial (35%) | 16171.41 | 11.80 | 1370.13 |
| Mtr.7211.1.S1_at | Weakly similar to Nonspecific lipid-transfer protein 3 precursor, partial (29%) | 24825.12 | 18.16 | 1367.23 |
| Mtr.42662.1.S1_at | Similar to Subtilisin-type protease, partial (35%) | 18774.02 | 13.76 | 1364.75 |
| Mtr.3239.1.S1_at | Unknown | 14949.46 | 11.23 | 1331.44 |
| Mtr.29537.1.S1_at | Unknown | 14680.98 | 11.35 | 1293.03 |
| Mtr.35623.1.S1_at | Weakly similar to Lipid transfer protein precursor, partial (44%) | 23403.42 | 18.81 | 1244.08 |
| Mtr.8907.1.S1_at | Unknown | 14990.84 | 12.47 | 1202.15 |
| Mtr.2609.1.S1_at | Unknown | 10611.50 | 9.15 | 1160.26 |
| Mtr.29599.1.S1_at | Unknown | 12268.55 | 10.85 | 1130.52 |
| Mtr.44209.1.S1_at | Similar to Seed coat peroxidase precursor, partial (83%) | 14485.83 | 12.86 | 1126.24 |
| Mtr.37270.1.S1_at | Similar to Legumin A precursor, partial (90%) | 11462.39 | 10.30 | 1113.20 |
| Mtr.7218.1.S1_at | Unknown | 11116.26 | 10.07 | 1103.39 |
| Mtr.16268.1.S1_at | Unknown | 14427.25 | 13.08 | 1102.62 |
| Mtr.16267.1.S1_at | Hypothetical protein | 8505.85 | 8.61 | 987.78 |
| Mtr.26806.1.S1_at | Unknown | 13361.42 | 13.57 | 984.50 |
| Mtr.29553.1.S1_at | Unknown | 14036.68 | 14.28 | 982.70 |
| Mtr.29180.1.S1_at | Unknown | 11945.52 | 12.49 | 956.05 |
| Mtr.3280.1.S1_at | Unknown | 10105.73 | 10.77 | 938.60 |
| Mtr.48528.1.S1_at | Hypothetical protein | 16512.08 | 17.74 | 930.87 |
| Mtr.26812.1.S1_at | Unknown | 8592.59 | 9.36 | 917.93 |
| Mtr.37269.1.S1_at | Similar to Legumin type B, Legumin type B beta chain (Fragment), partial (92%) | 9133.17 | 9.97 | 916.00 |
| Mtr.37289.1.S1_at | Similar to Convicilin precursor, partial (87%) | 11003.28 | 12.26 | 897.14 |
| Mtr.16267.1.S1_x_at | Hypothetical protein | 9507.23 | 11.11 | 855.74 |
| Mtr.35451.1.S1_at | Unknown | 11784.38 | 14.35 | 821.30 |
| Mtr.37272.1.S1_at | Similar to LegA class precursor, partial (79%) | 9500.61 | 12.00 | 791.76 | a = expression level in seed coat;
b = maximum expression level in other non-seed tissues;
c = ratio of a to b The genes encoding enzymes of PA biosynthesis have a clearly defined expression pattern in developing seed, with maximal transcript level at 10-12 dap followed by a decline to very low levels by 36 dap, paralleling the deposition pattern of PAs in the seed coat (Pang et al., 2007). Of the TT2-induced, seed coat preferentially expressed genes, many exhibited the same expression pattern as flavonoid/PA biosynthetic genes such as ANR and chalcone synthase (CHS) (for example the TTG1 ortholog) (FIG. 4A-C), as shown by mining the *Medicago* Gene Expression Atlas (Benedito et al., 2008). Others, however, were expressed later in seed development, and likely reflect transcripts present in contaminating seed tissue that do not play a role in PA biosynthesis.

Example 5

Cloning and Expression of UGT72L1

The genomic sequence of UGT72L1 was retrieved from the *Medicago* BAC clone of GenBank accession AC124966. The physical sequence, which lacks introns, was cloned from *M. truncatula* A17 wild-type genomic DNA with primers MtUGT72L1CF and MtUGT72L1R (SEQ ID NOs:25-26):

```
MtUGT72L1CF:
5'-CACCATGAACTTGGCCTCAAATTTCATGG-3'
(start codon is bolded).

MtUGT72L1R:
5'-TTAAATCTGGTTTTTCTGCACCAAA-3'
(stop codon is bolded).
```

The PCR product was cloned into pGEM T-easy vector (Promega, Madison, Wis.) for confirmation by sequencing. The ORF sequence was also obtained by RT-PCR with pfu DNA polymerase (Stratagene, San Diego, Calif.) and cDNA transcribed from total RNA from the 239-5 hairy root line using the primers MtUGT72L1CF and MtUGT72L1R.

The RT-PCR product was cloned into the Gateway Entry vector pENTR/D-TOPO (Invitrogen, Carlsbad, Calif.) to give the construct pENTR-UGT72L1. After confirmation by sequencing, this construct was then amplified using the primer pair MtUGT72L1BF and MtUGT72L1PR (SEQ ID NOs:27-28) start and stop codons in bold), which added BamHI and PstI sites upstream and downstream of the ORF:

```
MtUGT72L1BF:
5'-CGGGATCCATGAACTTGGCCTCAAATTTCATGG-3'

MtUGT72L1PR:
5'-TGAACTGCAGTTAAATCTGGTTTTTCTGCAC-3'
```

The PCR fragment was purified and digested with BamHI and PstI, followed by ligation into BamHI/PstI double digested pMAL-c2X vector (New England Biolabs, Beverly, Mass.). The constructs pMAL-UGT72L1, with the GT open reading frame fused to maltose binding protein (MBP) (SEQ ID NO:4), was then transformed into the *E. coli* host strain NovaBlue (DE3) for protein induction.

Single colonies of NovaBlue (DE3) harboring pMAL-UGT72L1 or pMAL-c2X control vector were inoculated into 1l LB medium containing 100 mg/l ampicillin and 10 g/l glucose, and the cells were grown to an OD600 of 0.6-0.7 at 37° C., at which time isopropyl-1-thio-β-D-galactopyranoside (IPTG) was added to a final concentration of 0.3 mM. The cells were then transferred to a 16° C. shaker for overnight culture. The cell cultures were harvested by centrifugation at 3000 rpm at 4° C. for 20 min and the pellets stored at −80° C.

Recombinant UGT72L1-MBP (SEQ ID NO:3) was purified by affinity chromatography on an amylase resin (New England Biolabs, Beverly, Mass.), and UGT72L1 released from MBP by cleavage with Factor Xa protease (New England Biolabs, Beverly, Mass.) according to the manufacturer's instructions. Proteins were analyzed by electrophoresis on a 10-20% SDS polyacrylamide gel stained with Coomassie brilliant blue.

UGT72L1 was assayed in a reaction of 50 µl containing 100 mM Tris-HCl pH7.5, 10 µl protein (~1.29 µg/µl) with 0.1 mM potential acceptor substrates and 0.25 mM $^{14}$C-UDP-Glucose (8.8 nCi/nmol). All assays were performed in triplicate for 1 hour at 30° C. along with boiled enzyme controls.

For studying pH optima, the buffers were 179 mM MES pH 5.0-7.0, and 179 mM Tris-HCl pH 7.0-9.0. Potential acceptor substrates were (−)-epicatechin, (−)-epigallocatechin, (+)-catechin, (+)-gallocatechin, procyanidins B1 and B2, cyanidin, dihydroquercetin, quercetin, kaemferol, apigenin, luteolin, liquiritigenin, daidzein and genistein (Sigma-Aldrich, St Louis, Mo.).

NMR spectroscopy was also performed on a sample of epicatechin glucoside produced in vitro with recombinant UGT72L1. A sample of approximately 1 mg of purified epicatechin glucoside was dissolved in 0.7 mL $CD_3OD$, evaporated to dryness under a stream of nitrogen, re-dissolved in 0.7 mL $CD_3OD$, and placed in a 5-mL NMR tube. 1-D Proton, TOCSY and NOESY NMR spectra and gradient enhanced COSY, HSQC, and HMBC spectra were acquired on a Varian Inova-500 MHz spectrometer at 308 K (35° C.). Chemical shifts were measured relative to the methyl signal of $CD_3OD$ ($\delta_H$=3.30 ppm, $\delta_C$=49.0 ppm). The NMR chemical shifts were assigned using the 1-D proton and 2-D COSY, TOCSY, HSQC, and HMBC spectra.

Example 6

Characterization of UGT72L1

Figure 4D:
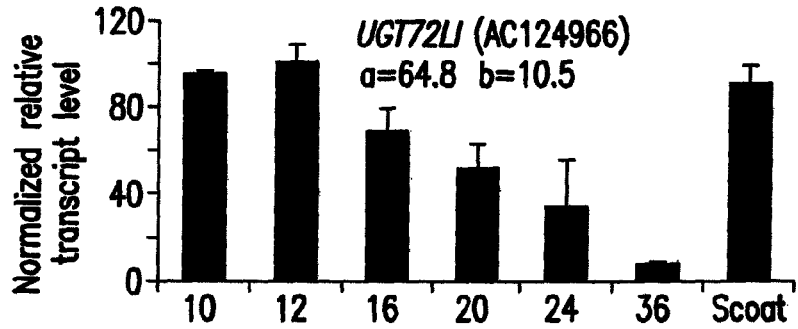
Figure 4E:
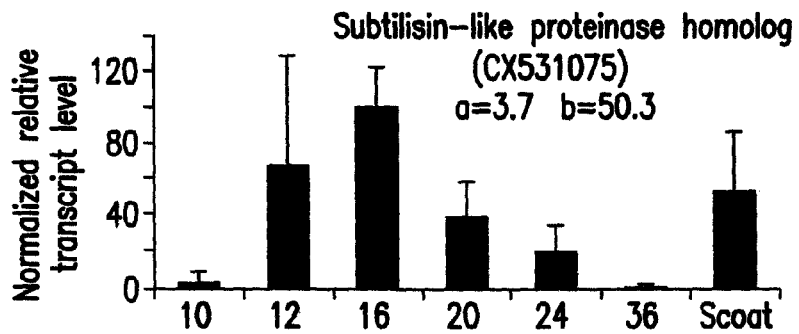
Figure 4F:
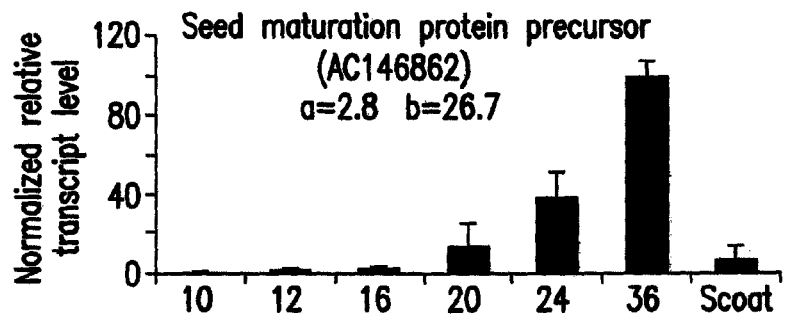
Figure 4G:
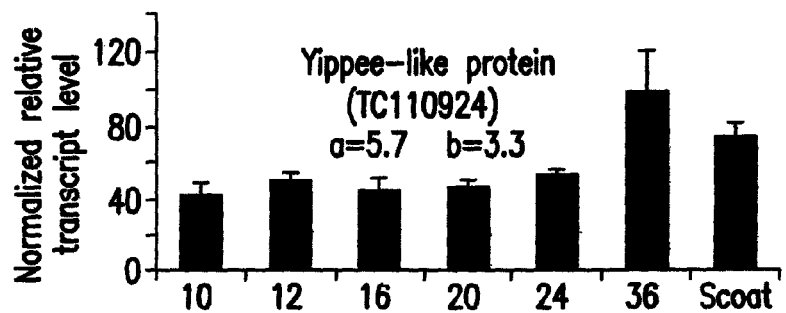
Figure 4H:
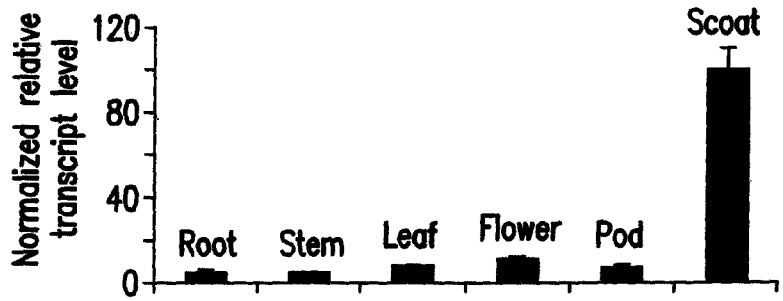

Two TT2-induced, seed coat preferentially expressed genes were annotated as encoding uridine diphosphate glycosyltransferases (UGTs). One, UGT72L1, exhibited a more than 10-fold higher expression in the seed coat than in any other organ (FIG. 4H), and a 64.8-fold higher expression in roots expressing 172 as compared to controls. Furthermore, its expression kinetics in developing seeds were similar to those of ANR, CHS and the TTG1 ortholog (FIG. 4D).

Figure 11A:
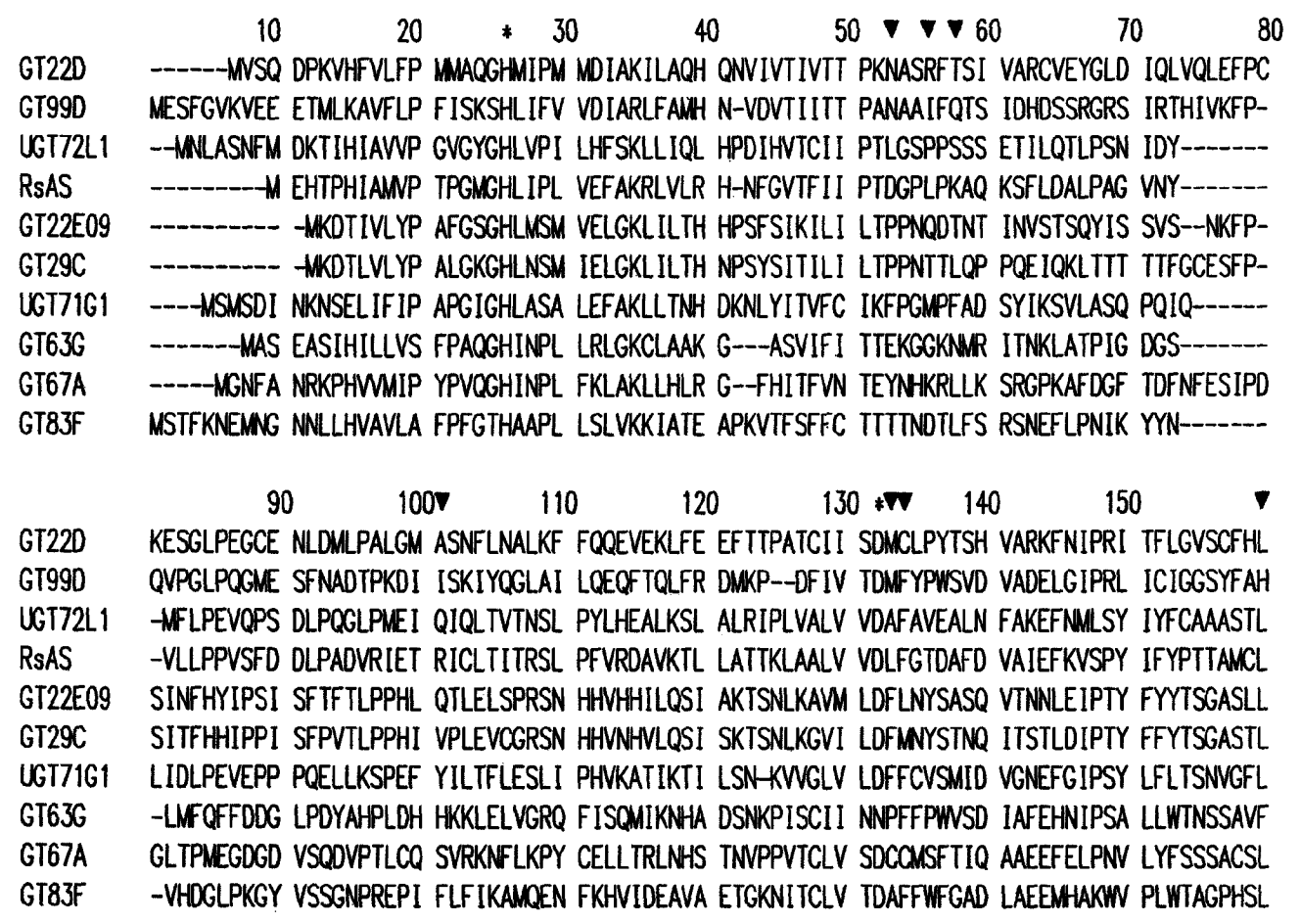

The genomic sequence of UGT72L1 present in *Medicago* BAC clone AC124966 contains no introns. Its coding sequence was obtained by RT-PCR as described above from total RNA isolated from TT2-expressing hairy roots. It encodes a protein of 482 amino acids (SEQ ID NO:1), with a putative isoelectric point of 5.16 and molecular weight of 53 kDa, and shows 52% amino acid identity to arbutin synthase (AS) from *Rauvolfia serpentina* (GenBank accession AJ310148; SEQ ID NO:29) and around 30% identity to UGT71G1 and other flavonoid UGTs from *M. truncatula* (FIG. 11). The nucleotide sequence encoding this protein is given at SEQ ID NO:2.

Figure 12:
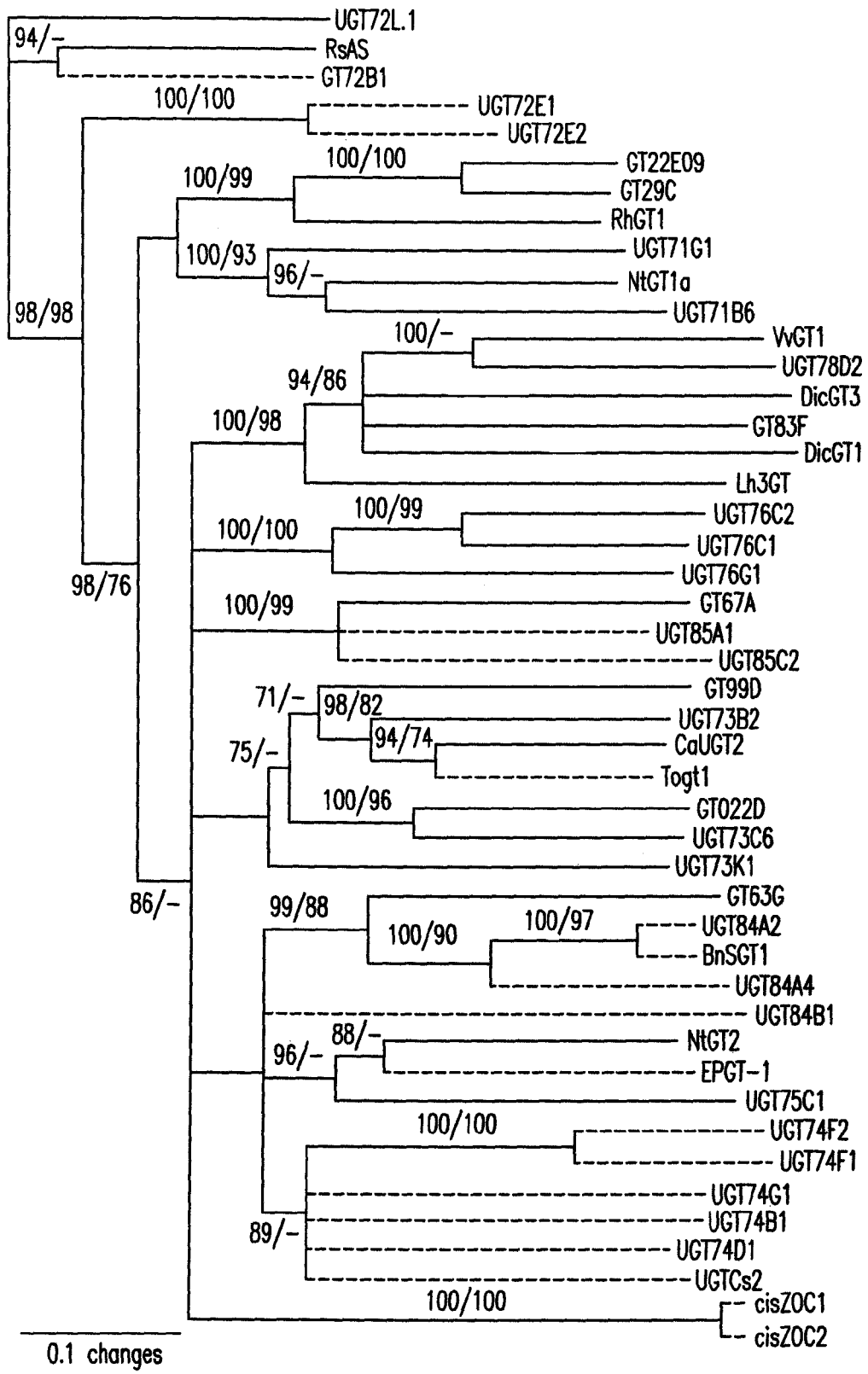
FIG. 12: Unrooted phylogram tree of UGT72L1 with UGTs from *M. truncatula* and functionally characterized glycosyltransferases from several other plant species. GenBank accession numbers of amino acid sequences are EU434684 for UGT72L1, CAC35167 for arbutin synthase from *Rauvolfia serpentine* (RsAs), NP_192016 for GT72B1 from *Arabidopsis*, and AAK53551 and AAL92460 for cis-zeatin O-glucosyltransferase 1 and 2 (cisZOC1 and cisZOC2) from *Zea mays*, respectively. All genes with the GT designation are *Medicago* UGTs, and their GenBank accession numbers, along with those of the other genes listed, can be found in Modolo et al. (2007). The first numbers above branches indicate neighbor-joining bootstrap values for nodes that received significant support (≧70%). The second numbers above branches indicate maximum parsimony bootstrap value for nodes that received significant support (≧70%). Dashed line after slash indicates the value is below 70 in one test. The scale bar indicates the relative phylogenetic distances measured as number of amino acid substitutions per site. Solid lines indicate the proteins that use (iso)flavonoids as substrates (all others are preceded by dashed lines).

For phylogenetic analysis, a multiple alignment of the deduced amino acid sequences of UGT72L1 and other UGTs was constructed using MAFFT (Katoh et al., 2005) and edited manually using MacClade 4.0 (Sinauer Associates, Sunderland, Mass.). Node support was estimated using neighbor-joining bootstrap analysis (1000 bootstrap replicates) and unweighted parsimony bootstrap analysis (100 bootstrap replicates, 5 RAS per bootstrap replicate, limiting the search to 500 trees per RAS) using PAUP*4.0b10 (Sinauer Associates). The most related sequence in soybean showed 50% amino acid identity. Phylogenetic analysis indicated that UGT72L1 clustered in an outlying clade with arbutin synthase but separate from (iso)flavonoid-specific UGTs from *M. truncatula* (Modolo et al., 2007) (FIG. 12). DNA gel blot analysis indicated that UGT72L1 is likely represented by three copies in the *M. truncatula* genome.

Figure 5A:
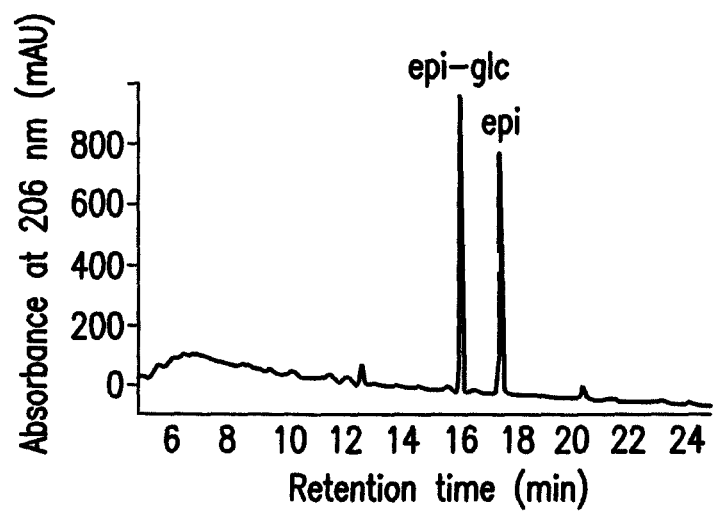
FIG. 5A-D: Characterization of the product of recombinant MBP-UGT72L1 fusion protein. (A) HPLC analysis of products from 1 h incubation of MBP-UGT72L1 fusion protein with UDP-glucose and epicatechin (epi). (B) as above, but with boiled enzyme. (C) mass fragment patterns and (D) UV absorption spectrum of epicatechin glucoside (epi-glc).
Figure 5B:
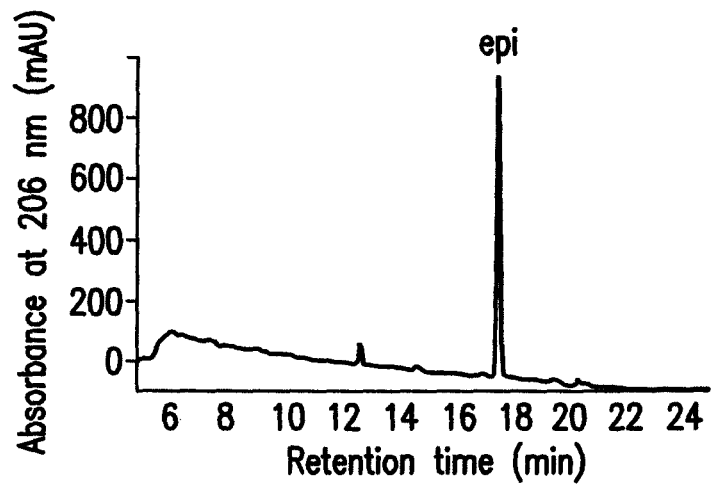
Figure 13A:
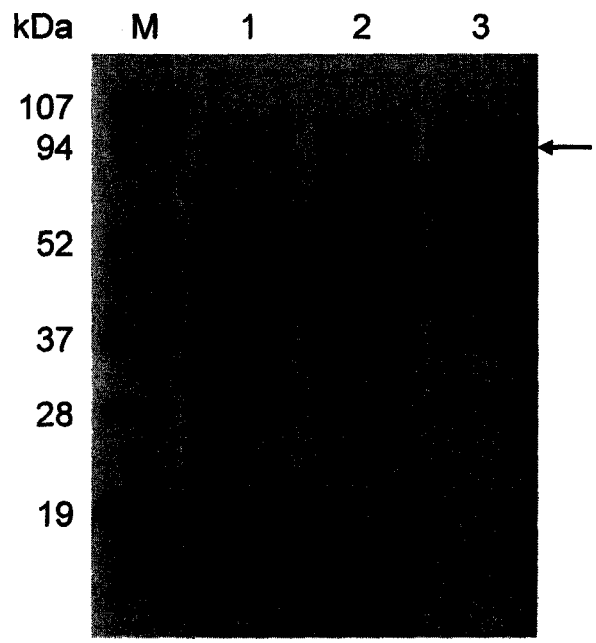
FIG. 13A-B: Expression of UGT72L1 in *E. coli*. (A) SDS-PAGE analysis of protein extracts from *E. coli* expressing UGT72L1-maltose binding protein fusion. M, prestained protein molecular weigh markers; lane 1, crude protein extract from IPTG-induced *E. coli* harboring control vector pMAL-c2X; lane 2, crude protein extract from IPTG-induced *E. coli* harboring pMAL-UGT72L1; lane 3, partially purified MBP-UGT72L1 fusion protein. (B) pH profile for the activity of MBP-UGT72L1 fusion with UDP glucose and (−)-epicatechin as substrates. Buffers were MES pH 5.0-7.0, and Tris-HCl pH 7.0-9.0. Data show the means and standard deviations from triplicate assays.
Figure 13B:
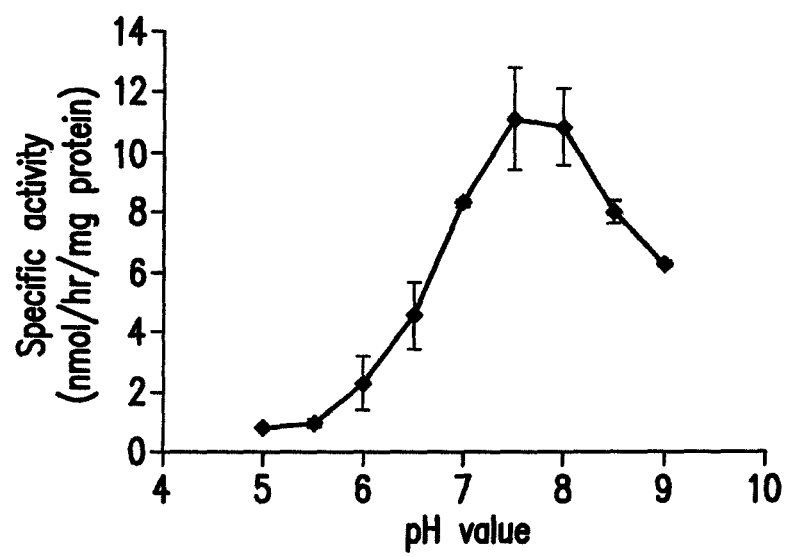

The open reading frame of UGT72L1 was expressed in *E. coli* as a maltose-binding protein (MBP) fusion (SEQ ID NO:3; FIG. 13A). With UDP-glucose as sugar donor, recombinant UGT72L1-MBP showed high activity for glucosylation of (−)-epicatechin (FIG. 5A), significant activity (27%) with (−)-epigallocatechin, and weak activity with (+)-catechin and cyanidin (less than 15% of the activity with epicatechin). UGT72L1 was not active with procyanidin B1, procyanidin B2, dihydroquercetin, kaempferol, quercetin, apigenin, luteolin, isoliquiritigenin, daidzein or genistein. The pH optimum for glycosylation of epicatechin was 7.5-8.5 (FIG. 13B). After removal of the MBP tag by proteolytic cleavage, the native enzyme exhibited the same overall activity and substrate specificity as the fusion protein, but was less stable on storage.

Figure 5C:
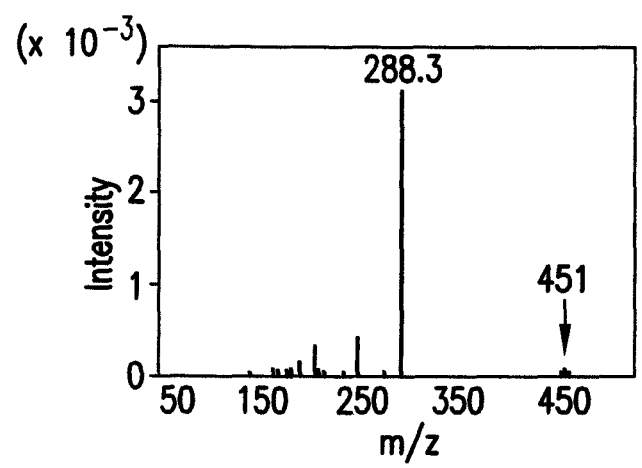
Figure 5D:
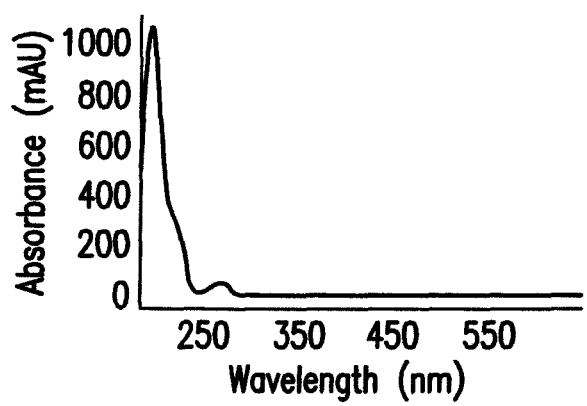
Figure 14B:
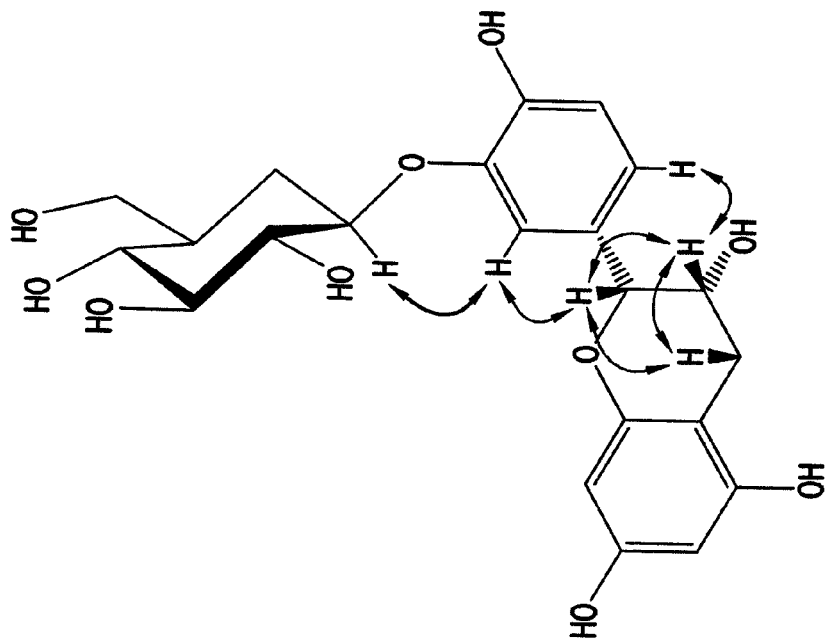
FIG. 14A-B: HMBC (A) and NOESY (B) correlations in epicatechin 3'-O-glucoside.
Figure 14A:
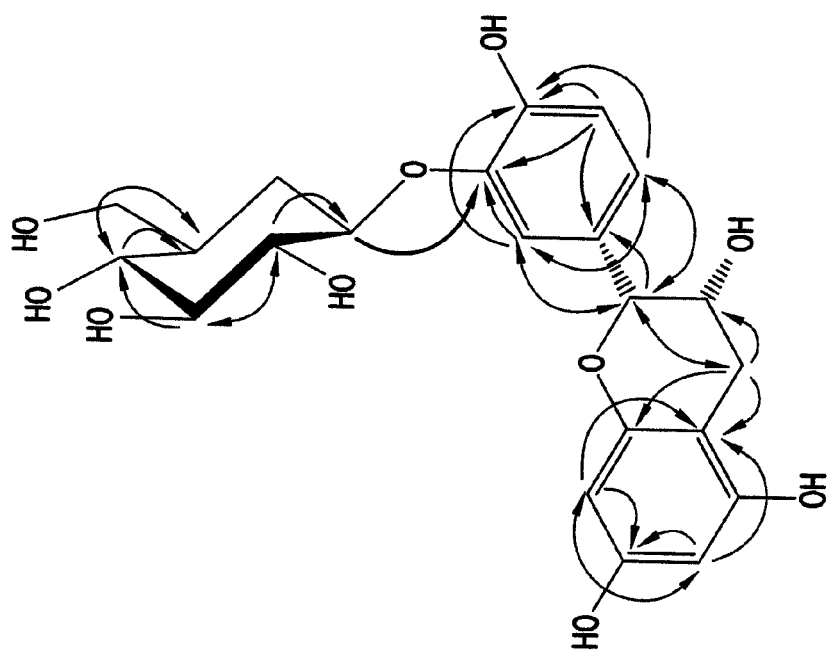

The product of the UGT72L1-catalyzed reaction exhibited the mass fragmentation pattern of an epicatechin glycoside and a UV absorption spectrum similar to that of epicatechin (FIG. 5C,D), and was converted to (−)-epicatechin on incubation with almond β-glucosidase. NMR analysis showed a cross peak between H-1 of β-glucose and C-3' of epicatechin in the HMBC spectrum, indicating linkage of glucose to O-3' of the aglycone (FIG. 14A). This was confirmed by a cross peak in the NOESY spectrum between H-1 of glucose and H-2' of epicatechin (FIG. 14B).

Kinetic analysis of recombinant MBP-UGT72L1 fusion protein revealed Km values for epicatechin and UDP glucose of 11.5 and 140 μM, respectively, and a Kcat value of $9.89 \times 10^{-3} \cdot s^1$.

Eight *Medicago* UGTs (SEQ ID NOs:30-37: GT22D, GenBank Accession No. ABI94020; GT22E09, GenBank accession No. ABI94021; GT29C, GenBank Accession No. ABI94022; UGT71G1 (also termed GT29H), GenBank Accession No. AAW56092; GT63G, GenBank Accession No. ABI94023; GT67A, GenBank Accession No. ABI94024; GT83F (also termed UGT78G1), GenBank Accession No. ABI94025; and GT99D, GenBank Accession No. DQ875465) are active with a range of flavonoid and isoflavonoid acceptor molecules (Modolo et al., 2007), including cyanidin and quercetin. However, none of these enzymes could glycosylate (−)-epicatechin.

Example 7

Identification of Epicatechin Glucoside in Seed of *M. truncatula*

Figure 6A:
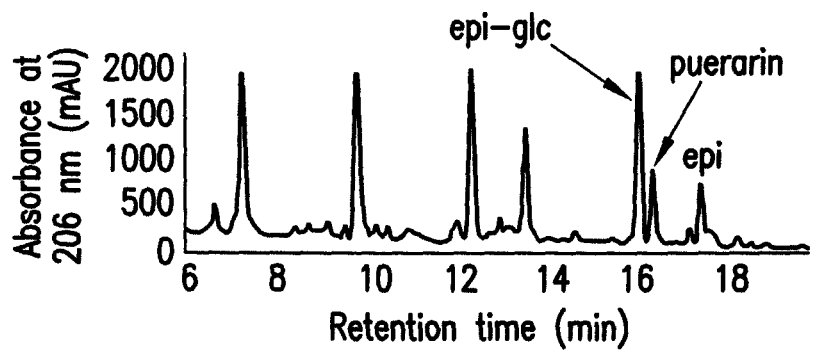
FIG. 6A-E: Identification of epicatechin glucoside in developing *Medicago* seed. (A) HPLC analysis of flavonoids from seeds at 12 dap. epi-glc, glucosylated epicatechin; epi, free epicatechin. Puerarin was internal standard. (B) As above, but following overnight hydrolysis with almond β-glucosidase. (C) UV absorption spectrum and (D) mass spectrum of epi-glc from *M. truncatula* seed. (E) Levels of epi-glc at different dap, based on analysis of 100 mg samples of pooled seed at each developmental stage.
Figure 6B:
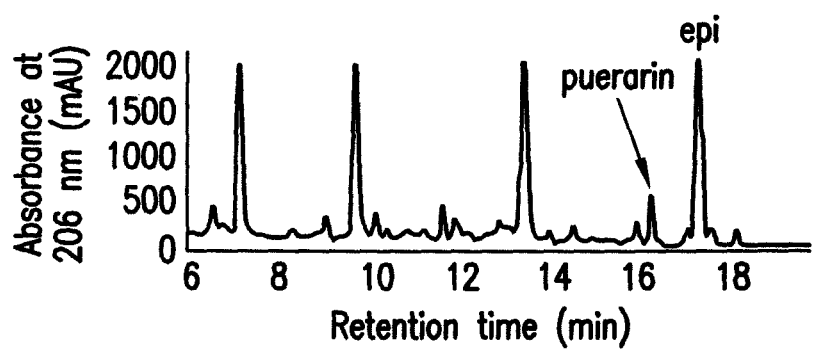
Figure 6C:
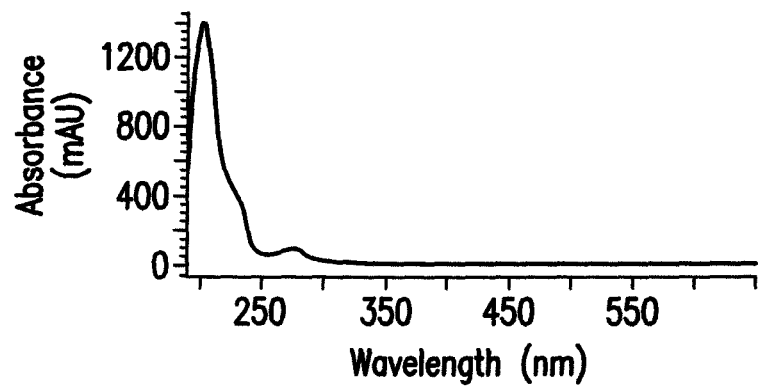
Figure 6D:
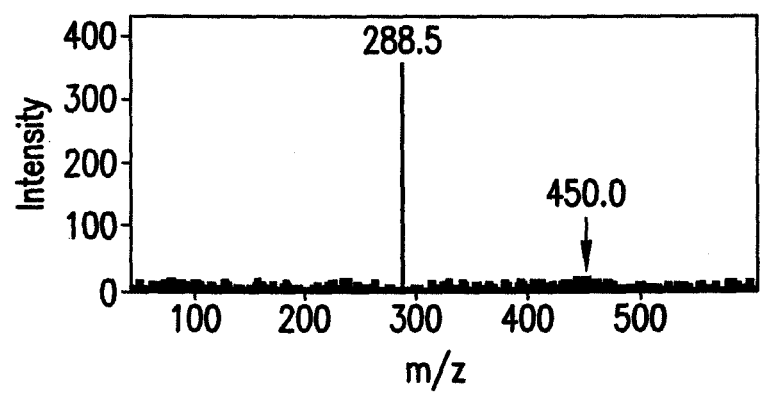
Figure 6E:
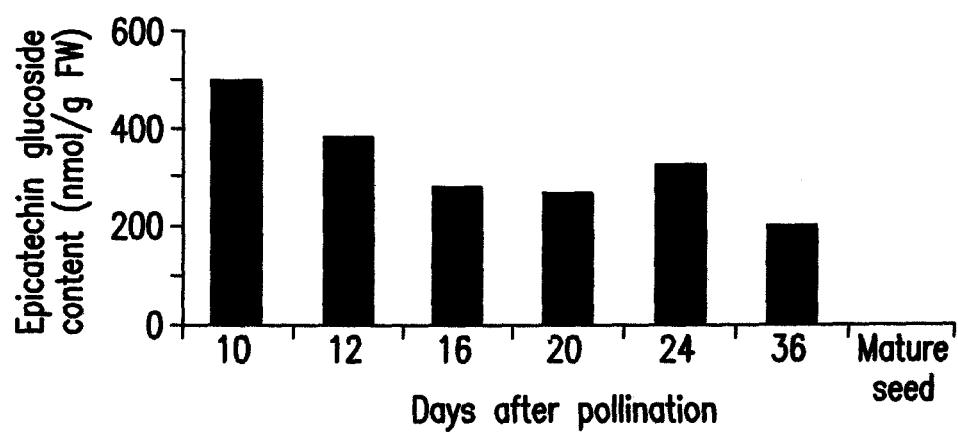
Figure 15:
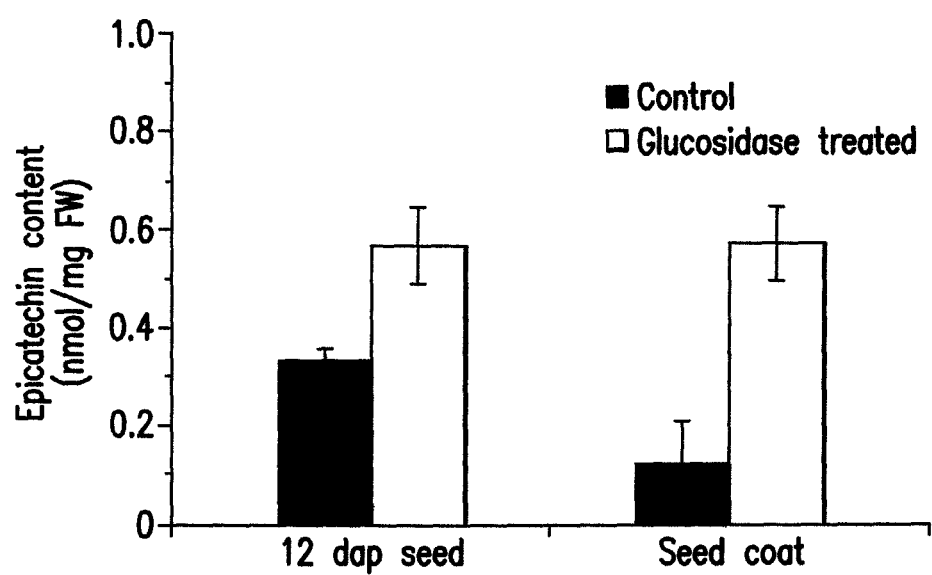
FIG. 15: Epicatechin content of extracts from intact seeds (12 dap) or corresponding isolated seed coats, with or without hydrolysis with β-glucosidase.

Flavonoid profiles of various organs and developing seeds were analyzed by LC-MS. Conjugates of apigenin, luteolin and quercetin (quercetin-3-O-glucoside) were found in all organs examined, as previously shown in alfalfa (Deavours and Dixon, 2005). In contrast, a compound with the same HPLC retention time, and UV- and mass-spectral characteristics as epicatechin glucoside (epi-glc), was found only in developing seeds (FIG. 6A,C,D). This disappeared, with a corresponding increase in free epicatechin, when extracts were treated with β-glucosidase (FIG. 6B). More than 75% of the epicatechin in seed coats at 12 dap was present as a hydrolysable glucoside (FIG. 15). Epi-glc declined during seed development and was not detected in mature seeds (FIG. 6E). It was also detected in soluble extracts from TT2-expressing hairy roots.

REFERENCES

The references listed below are incorporated herein by reference to the extent that they supplement, explain, provide a background for, or teach methodology, techniques, and/or compositions employed herein.

U.S. Pat. No. 4,518,584; U.S. Pat. No. 4,535,060; U.S. Pat. No. 4,554,101; U.S. Pat. No. 4,737,462; U.S. Pat. No. 5,302,523; U.S. Pat. No. 5,322,783; U.S. Pat. No. 5,384,253; U.S. Pat. No. 5,464,765; U.S. Pat. No. 5,508,184; U.S. Pat. No. 5,508,468; U.S. Pat. No. 5,538,877; U.S. Pat. No. 5,538,880; U.S. Pat. No. 5,545,818; U.S. Pat. No. 5,550,318; U.S. Pat. No. 5,563,055; U.S. Pat. No. 5,591,616; U.S. Pat. No. 5,610,042
U.S. Patent Publn. 2004/0093632
U.S. patent application Ser. No. 12/108,332
Abdullah et al., *Biotechnology*, 4:1087, 1986.
Achnine et al., *Plant J.*, 41:875-887, 2005.
Aharoni et al., *Plant J.*, 28:319-332, 2001.
Altschul et al., *J. Mol. Biol.*, 215:403-410, 1990.
Aziz et al., *Planta*, 221:28-38, 2005.
Barry and McNabb, *Brit. J. Nutrition*, 81:263-272, 1999.
Bates, *Mol. Biotechnol.*, 2(2):135-145, 1994.
Battraw and Hall, *Theor. App. Genet.*, 82(2):161-168, 1991.
Baudry et al., *Plant J.*, 39: 366-380, 2004.
Baxter et al., *Proc Nal Acad Sci, USA* 102: 2649-2654, 2005.
Benedito et al., *Plant J.*, 55:504-513, 2008.
Bevan et al., *Nucleic Acids Research*, 11(2):369-385, 1983.
Bhattacharjee et al., *J. Plant Bioch. and Biotech.*, 6, (2):69-73. 1997.
Borevitz et al., *Plant Cell*, 12:2383-2393, 2000.
Bouchez et al., *EMBO Journal*, 8(13):4197-4204, 1989.
Brevetti et al., *Ann. Oftalmol. Clin. Ocul.*, 115:109-116, 1989.
Broun, *Curr Opin Plant Biol* 7: 202-209, 2004.
Buchanan-Wollaston et al., *Plant Cell Reports*, 11:627-631. 1992
Buising and Benbow, *Mol. Gen. Genet.*, 243(1):71-81. 1994.
Callis et al., *Genes Dev.*, 1:1183-1200, 1987.
Casa et al., *Proc. Natl. Acad. Sci. USA*, 90(23):11212-11216, 1993.
Chandler et al., *Plant Cell*, 1:1175-1183, 1989.
Chen et al., *Biotechniques* 16:664-668, 1994.
Christou; et al., *Proc. Natl. Acad. Sci. USA*, 84(12):3962-3966, 1987.
Chu et al., *Scientia Sinica*, 18:659-668, 1975.
Conkling et al., *Plant Physiol.*, 93:1203-1211, 1990.
DE 3642 829
De Block et al., *EMBO J.*, 6(9):2513-2518, 1987.
De Block et al., *Plant Physiol.*, 91:694-701, 1989.
Deavours and Dixon, *Plant Physiology*, 138:2245-2259, 2005.
Deavours et al., *Plant Molec. Biol.*, 62:715-733, 2006.
Debeaujon et al., *Plant Cell*, 13:853-871, 2001.
Dellaporta et al., In: *Chromosome Structure and Function: Impact of New Concepts*, 18th Stadler Genetics Symposium, 11:263-282, 1988.
Dellaporta et al., *Plant Mol. Biol. Rep.*, 1:19-21, 1983.
Deluc et al., *Plant Physiol.*, 140:499-511, 2006.
D'Halluin et al., *Plant Cell*, 4(12):1495-1505, 1992.
Dixon et al., *New Phytologist*, 165:9-28, 2005.

Ebert et al., *Proc. Natl. Acad. Sci. USA*, 84:5745-5749, 1987.
Ellis et al., *EMBO J.*, 6(11):3203-3208, 1987.
European Patent Appln. 154,204.
Fire et al., *Nature*, 391(6669):806-811, 1998.
Foo et al., *Phytochemistry*, 54:173-81, 2000.
Fraley et al., *Bio/Technology*, 3:629-635, 1985.
Fromm et al., *Nature*, 319:791-793, 1986.
Gallie et al., *Plant Cell*, 1:301-311, 1989.
Gelvin et al., In: *Plant Molecular Biology Manual*, 1990.
Ghosh-Biswas et al., *J. Biotechnol.*, 32:1-10, 1994.
Goffard and Weiller, *BMC Bioinformatics* 8:87, 2007.
Grotewold, *Planta* 219:906-909, 2004.
Gu et al., *J. Agric. Food Chem.*, 50:4852-4860, 2002.
Hall et al., *Canadian Veterinary J.*, 35:702-705, 1994.
Hamilton et al., *Proc. Natl. Acad. Sci. USA*, 93:9975-9979, 1996.
Haseloff et al., *Proc. Natl. Acad. Sci. USA*, 94:2122-2127, 1997.
He and Dixon, *Plant Cell*, 12:1689-1702, 2000.
He et al., *Plant Cell Reports*, 14 (2-3):192-196, 1994.
Hiei et al., *Plant. Mol. Biol.*, 35:205-218, 1997.
Hinchee et al., *Bio/technol.*, 6:915-922, 1988.
Horsch et al., *Science*, 227:1229-1231, 1985.
Hou and Lin, *Plant Physiology*, 111:166, 1996.
Hudspeth and Grula, *Plant Mol. Biol.*, 12:579-589, 1989.
Ikuta et al., *Bio/technol.*, 8:241-242, 1990.
Ishida et al., *Nat. Biotechnol.*, 14:745-750, 1996.
Jackson and Barry, *J. Sci. Food Agric.*, 71:103-110, 1996.
Kaeppler et al., *Plant Cell Reports* 9: 415-418, 1990.
Kaeppler, Somers, Rines, Cockburn, *Theor. Appl. Genet.*, 84:560-566, 1992.
Katoh et al., *Nucleic Acids Res* 33: 511-518, 2005.
Katz et al., *J. Gen. Microbiol.*, 129:2703-2714, 1983.
Kitamura et al., *Plant J.*, 37:104-114, 2004.
Klee et al., *Bio-Technology*, 3:637-642, 1985.
Knittel et al., *Plant Cell Reports*, 14(2-3):81-86, 1994.
Koupai-Abyazani et al., *J. Agri. Food Chem.*, 41:565-569, 1993.
Kyte and Doolittle, *J. Mol. Biol.*, 157:105 132, 1982.
Lawton et al., *Plant Mol. Biol.* 9:315-324, 1987.
Lazo et al., *Biotechnology.*, 9(10):963-967, 1991.
Lazzeri, *Methods Mol. Biol.*, 49:95-106, 1995.
Lee et al., *Brit. J. Nutr.*, 93:895-800, 2005.
Lee et al., *Korean J. Genet.*, 11:65-72, 1989.
Lees, *Basic Life Sci.*, 59:915-934, 1992.
Lepiniec et al., *Annu. Rev. Plant Biol.* 57: 405-430, 2006.
Li et al., *J. Sci. Food Agric.*, 70:89-101, 1996.
Limpens et al., *J Exp Bot* 55: 983-992, 2004.
Lin et al., *J. Nat. Prod.*, 65:505-8, 2002.
Liu et al., *Proc. Natl. Acad. Sci. USA*, 99, 14578-14583, 2002.
Lorz et al., *Mol Gen Genet*, 199:178-182, 1985.
Marcotte et al., *Nature*, 335:454, 1988.
Martinez et al., *Cell*, 110:563-574, 2002.
Mathews et al., *Plant Cell*, 15:1689-1703, 2003.
McCabe and Martinell, *Bio-Technology*, 11(5):596-598, 1993.
McCormac et al., *Euphytica*, 99(1):17-25, 1998.
McKersie et al., *Plant Physiol.* 103:1155-1163, 1993.
McKhann and Hirsch, *Plant Mol. Biol.* 24(5):767-77, 1994
McManus and Sharp, *Nat. Rev. Genet.* 3:737-47, 2002.
Modolo et al., *Plant Molec. Biol.* 64:499-518, 2007.
Mueller et al., *Pl. Physiol.* 123:1561-1570, 2000.
Murakami et al., *Mol. Gen. Genet.*, 205:42-50, 1986.
Murashige and Skoog, *Physiol. Plant.*, 15:473-497, 1962.
Nagatani et al., *Biotech. Tech.*, 11(7):471-473, 1997.
Nesi et al., *Plant Cell* 12: 1863-1878, 2000.
Nesi et al., *Plant Cell* 13: 2099-2114, 2001.
Odell et al., *Nature*, 313:810-812, 1985.
Ogawa et al., *Sci. Rep.*, 13:42-48, 1973.
Omirulleh et al., *Plant Mol. Biol.*, 21(3):415-428, 1993.
Ow et al., *Science*, 234:856-859, 1986.
Pang et al., *Plant Physiol* 145: 601-615, 2007.
Pascual-Teresa et al., *J. Agric. Food Chem.*, 46:4209-4213, 1998.
Pataki et al., *Am. J. Clin. Nutr.*, 75:894-899, 2002.
PCT Appln. WO 9217598
PCT Appln. WO 94/09699
PCT Appln. WO 95/06128
PCT Appln. WO 97/4103
PCT Appln. WO 97/41228
Peel and Dixon, *Natural Products Communications*, 2:1009-1014, 2007.
Peel et al., abstr. 1351 (P43006), presented at Botany & Plant Biology Joint Congress, Chicago, Ill., Jul. 8, 2007.
Potrykus et al., *Mol. Gen. Genet.*, 199:183-188, 1985.
Prasher et al., *Biochem. Biophys. Res. Commun.*, 126(3): 1259-1268, 1985.
Quandt et al., *Mol. Pl. Microbe-Interact.* 6:699-706, 1993.
Quattrocchio et al., *Plant Cell*, 11:1433-1444, 1999.
Ramakers et al, *Neuroscience Letters* 339:62-66, 2003.
Reichel et al., *Proc. Natl. Acad. Sci. USA*, 93 (12) p. 5888-5893. 1996.
Rhodes et al., *Methods Mol. Biol.*, 55:121-131, 1995.
Ritala et al., *Plant Mol. Biol.*, 24(2):317-325, 1994.
Rogers et al., *Methods Enzymol.*, 153:253-277, 1987.
Rozen and Skaletsky, In: *Bioinformatics methods and protocols: methods in molecular biology*, Krawetz and Misener (Eds.), Humana Press, NJ, 365-386, 2000.
Sambrook et al., In: *Molecular Cloning-A Laboratory Manual* (second edition), Cold Spring Harbour Laboratory Press, 1989.
Sharma and Dixon, *Plant J.*, 44:62-75, 2005.
Sheen et al., *Plant Journal*, 8(5):777-784, 1995.
Singsit et al., *Transgenic Res.*, 6(2):169-176, 1997.
Skadhauge et al., *Am. J. Bot.*, 84:494-502, 1997.
Snyder and Nicholson, *Science* 248:1637-1639, 1990.
Spencer et al., *Plant Molecular Biology*, 18:201-210, 1992.
Stalker et al., *Science*, 242:419-422, 1988.
Sullivan et al., *Mol. Gen. Genet.*, 215(3):431-440, 1989.
Sutcliffe, *Proc. Natl. Acad. Sci. USA*, 75:3737-3741, 1978.
Suzuki et al., *Planta*, 220:698-707, 2005.
Thillet et al., *J. Biol. Chem.*, 263:12500-12508, 1988.
Thomas et al., *Plant Sci.*, 69:189-198, 1990.
Thompson et al., *EMBO J.*, 6(9):2519-2523, 1987.
Thompson et al., *Nucleic Acids Res* 25: 4876-4882, 1997.
Tian et al., *Plant Cell Rep.*, 16:267-271, 1997.
Tingay et al., *Plant J.*, 11(6):1369-1376, 1997.
Tohge et al., *Plant J.*, 42:218-235, 2005.
Tomes et al., *Plant. Mol. Biol.* 14(2):261-268, 1990.
Toriyama et al., *Theor Appl. Genet.*, 73:16, 1986.
Treutter et al., *Acta Horticulturae*, 789-796, 1994.
Treutter, *J. Chromatography*, 467:185-193, 1989.
Tsukada et al., *Plant Cell Physiol.*, 30(4)599-604, 1989.
Twell et al., *Plant Physiol* 91:1270-1274, 1989.
Uchimiya et al., *Mol. Gen. Genet.*, 204:204, 1986.
Van Eck et al., *Plant Cell Reports*, 14(5):299-304, 1995.
Vasil et al., *Plant Physiol.*, 91:1575-1579, 1989.
Walder et al., *Gene*, 42:133, 1986.
Walker et al., *Proc. Natl. Acad. Sci. USA*, 84:6624-6628, 1987.
Wang et al., *Molecular and Cellular Biology*, 12(8):3399-3406, 1992.
Wright et al., In: *Agrobacterium Protocols*, Wang (Ed.), Humana Press, 343:129-136, 2006.

Yamada et al., *Plant Cell Rep.,* 4:85, 1986.
Yang and Russell, *Proc. Natl. Acad. Sci. USA,* 87:4144-4148, 1990.
Zhang et al., *Development* 130: 4859-4869, 2003.
Zheng and Edwards, *J. Gen. Virol.,* 71:1865-1868, 1990.
Zhou et al., *Plant Cell Reports,* 12(11).612-616, 1993.
Zukowsky et al., *Proc. Natl. Acad. Sci. USA,* 80:1101-1105, 1983.

What is claimed is:

1. An isolated nucleic acid sequence selected from the group consisting of:
   (a) a nucleic acid sequence encoding the polypeptide sequence of SEQ ID NO: 1 or SEQ ID NO:3;
   (b) a nucleic acid sequence comprising a sequence selected from the group consisting of SEQ ID NO:2 and SEQ ID NO:4;
   (c) a nucleic acid sequence encoding a polypeptide with at least 95% amino acid identity to SEQ ID NO:1 or SEQ ID NO:3, and encodes a polypeptide with epicatechin glycosyltransferase activity;
   (d) and the complement of any one of the sequences of (a)-(c),
   wherein the nucleic acid sequence is operably linked to a heterologous promoter; and wherein the polypeptide with epicatechin glycosyltransferase activity comprises a binding site for UDP-glucose and an acceptor binding site.

2. A recombinant vector comprising the isolated nucleic acid sequence of claim 1.

3. The recombinant vector of claim 2, further comprising at least one additional sequence chosen from the group consisting of: a regulatory sequence, a sequence that encodes a polypeptide that activates anthocyanin or proanthocyanidin biosynthesis, a selectable marker, a leader sequence and a terminator.

4. The recombinant vector of claim 3, wherein the polypeptide that activates anthocyanin or proanthocyanidin biosynthesis is selected from the group consisting of: phenylalanine ammonia-lyase (PAL), cinnamate 4-hydroxylase (C4H), 4-coumarate:CoA ligase (4CL), chalcone synthase (CHS), chalcone isomerase (CHI), flavanone 3-hydroxylase (F3H), dihydroflavonol reductase (DFR), anthocyanidin synthase (ANS), leucoanthocyanidin reductase (LAR), anthocyanidin reductase (ANR), a proanthocyanidin or anthocyanidin glucosyltransferase (GT), LAP1, LAP2, LAP3, LAP4, or AtPAP1.

5. The recombinant vector of claim 2, wherein the promoter is a plant developmentally-regulated, organelle-specific, inducible, tissue-specific, constitutive, or cell-specific promoter.

6. The recombinant vector of claim 2, defined as an isolated expression cassette.

7. An isolated polypeptide having at least 95% amino acid identity to the amino acid sequence of SEQ ID NO:1 or SEQ ID NO:3, wherein said polypeptide has epicatechin glucosyltransferase activity.

8. The isolated polypeptide of claim 7, comprising the amino acid sequence of SEQ ID NO:1, or SEQ ID NO:3.

9. A transgenic plant transformed with the nucleic acid of claim 1.

10. The transgenic plant of claim 9, wherein the plant is a *Medicago* plant.

11. The transgenic *Medicago* plant of claim 10, wherein the plant expresses the selected DNA and exhibits increased proanthocyanidin biosynthesis in selected tissues relative to those tissues in a second plant that differs from the transgenic plant only in that the selected DNA is absent.

12. The transgenic plant of claim 9, wherein the nucleic acid sequence encodes an epicatechin glucosyltransferase polypeptide selected from the group consisting of SEQ ID NO:1, or SEQ ID NO:3.

13. The transgenic plant of claim 9, wherein the complement is complementary to a sequence encoding an epicatechin glucosyltransferase active in proanthocyanidin biosynthesis.

14. The transgenic plant of claim 13, wherein the complement is the complement of SEQ ID NO:2 or SEQ ID NO:4.

15. The transgenic plant of claim 9, further defined as transformed with a DNA sequence encoding the polypeptide of SEQ ID NO:1.

16. The transgenic plant of claim 9, further defined as a forage crop.

17. The transgenic plant of claim 16, wherein the plant is a forage legume.

18. The transgenic plant of claim 17, wherein the forage legume is alfalfa.

19. The transgenic plant of claim 9, wherein the plant is further defined as comprising a transgenic coding sequence encoding an anthocyanin reductase polypeptide selected from the group consisting of: SEQ ID NO:21 and SEQ ID NO:22.

20. The transgenic plant of claim 9, wherein the plant is further defined as transformed with a recombinant vector comprising a sequence that encodes a polypeptide that activates anthocyanin or proanthocyanidin biosynthesis, wherein said polypeptide is selected from the group consisting of: phenylalanine ammonia-lyase (PAL), cinnamate 4-hydroxylase (C4H), 4-coumarate:CoA ligase (4CL), chalcone synthase (CHS), chalcone isomerase (CHI), flavanone 3-hydroxylase (F3H), dihydroflavonol reductase (DFR), anthocyanidin synthase (ANS), leucoanthocyanidin reductase (LAR), anthocyanidin reductase (ANR), a proanthocyanidin or anthocyanidin glucosyltransferase (GT), LAP1, LAP2, LAP3, LAP4, or AtPAP1.

21. The transgenic plant of claim 9, further defined as a fertile R0 transgenic plant.

22. The transgenic plant of claim 9, further defined as a progeny plant of any generation of a fertile R0 transgenic plant, wherein the transgenic plant comprises the selected DNA.

23. The transgenic plant of claim 9, wherein the plant is further defined as comprising a transgenic sequence of claim 1 that down-regulates SEQ ID NO:1 expression.

24. A seed of the transgenic plant of claim 9, comprising the nucleic acid of claim 1.

25. A cell transformed with the nucleic acid of claim 1.

26. A method of producing a plant with increased proanthocyanidin biosynthesis relative to a second plant, comprising expressing in the plant the isolated nucleic acid sequence of claim 1 and wherein the second plant lacks the isolated nucleic acid sequence.

27. The method of claim 26, wherein the plant further comprises a recombinant vector comprising a sequence that encodes a polypeptide that activates anthocyanin or proanthocyanidin biosynthesis, wherein said polypeptide is selected from the group consisting of: phenylalanine ammonia-lyase (PAL), cinnamate 4-hydroxylase (C4H), 4-coumarate:CoA ligase (4CL), chalcone synthase (CHS), chalcone isomerase (CHI), flavanone 3-hydroxylase (F3H), dihydroflavonol reductase (DFR), anthocyanidin synthase (ANS), leucoanthocyanidin reductase (LAR), anthocyanidin reductase (ANR), a proanthocyanidin or anthocyanidin glucosyltransferase (GT), LAP1, LAP2, LAP3, LAP4, or AtPAP1.

28. The method of claim 26, wherein the nucleic acid sequence of claim 1 is introduced into the plant by plant breeding.

29. The method of claim 26, wherein the nucleic acid sequence of claim 1 is introduced into the plant by genetic transformation of the plant.

30. The method of claim 26, wherein the promoter is a constitutive or tissue specific promoter.

31. The method of claim 26, wherein the plant is further defined as a forage crop.

32. The method of claim 26, wherein the plant is a forage legume.

33. The method of claim 26, wherein the plant is alfalfa.

34. The method of claim 26, further comprising preparing a transgenic progeny plant of any generation of the plant, wherein the progeny plant comprises the nucleic acid sequence of claim 1.

35. A plant prepared by the method of claim 26.

36. A plant part prepared by the method of claim 26.

37. A method of making food or feed for human or animal consumption comprising:
(a) obtaining the plant of claim 9;
(b) growing the plant under plant growth conditions to produce plant tissue from the plant; and
(c) preparing food or feed for human or animal consumption from the plant tissue.

38. The method of claim 37, wherein preparing food comprises harvesting the plant tissue.

39. The method of claim 37, wherein the food is hay, silage, starch, protein, meal, flour or grain.

* * * * *

```
                            SEQUENCE LISTING

<160> NUMBER OF SEQ ID NOS: 66

<210> SEQ ID NO 1
<211> LENGTH: 482
<212> TYPE: PRT
<213> ORGANISM: Medicago truncatula

<400> SEQUENCE: 1

Met Asn Leu Ala Ser Asn Phe Met Asp Lys Thr Ile His Ile Ala Val
1               5                   10                  15

Val Pro Gly Val Gly Tyr Gly His Leu Val Pro Ile Leu His Phe Ser
            20                  25                  30

Lys Leu Leu Ile Gln Leu His Pro Asp Ile His Val Thr Cys Ile Ile
        35                  40                  45

Pro Thr Leu Gly Ser Pro Ser Ser Ser Glu Thr Ile Leu Gln Thr
    50                  55                  60

Leu Pro Ser Asn Ile Asp Tyr Met Phe Leu Pro Glu Val Gln Pro Ser
65                  70                  75                  80

Asp Leu Pro Gln Gly Leu Pro Met Glu Ile Gln Ile Gln Leu Thr Val
                85                  90                  95

Thr Asn Ser Leu Pro Tyr Leu His Glu Ala Leu Lys Ser Leu Ala Leu
            100                 105                 110

Arg Ile Pro Leu Val Ala Leu Val Val Asp Ala Phe Ala Val Glu Ala
        115                 120                 125

Leu Asn Phe Ala Lys Glu Phe Asn Met Leu Ser Tyr Ile Tyr Phe Cys
    130                 135                 140

Ala Ala Ala Ser Thr Leu Ala Trp Ser Phe Tyr Leu Pro Lys Leu Asp
145                 150                 155                 160

Glu Glu Thr Thr Cys Glu Tyr Arg Asp Leu Pro Glu Pro Ile Lys Val
                165                 170                 175

Pro Gly Cys Val Pro Leu His Gly Arg Asp Leu Leu Thr Ile Val Gln
            180                 185                 190

Asp Arg Ser Ser Gln Ala Tyr Lys Tyr Phe Leu Gln His Val Lys Ser
        195                 200                 205

Leu Ser Phe Ala Asp Gly Val Leu Val Asn Ser Phe Leu Glu Met Glu
    210                 215                 220

Met Gly Pro Ile Asn Ala Leu Thr Glu Glu Gly Ser Gly Asn Pro Ser
225                 230                 235                 240

Val Tyr Pro Val Gly Pro Ile Ile Gln Thr Val Thr Gly Ser Val Asp
                245                 250                 255

Asp Ala Asn Gly Leu Glu Cys Leu Ser Trp Leu Asp Lys Gln Gln Ser
            260                 265                 270

Cys Ser Val Leu Tyr Val Ser Phe Gly Ser Gly Gly Thr Leu Ser His
        275                 280                 285

Glu Gln Ile Val Glu Leu Ala Leu Gly Leu Glu Leu Ser Asn Gln Lys
    290                 295                 300

Phe Leu Trp Val Val Arg Ala Pro Ser Ser Ser Ser Asn Ala Ala
305                 310                 315                 320

Tyr Leu Ser Ala Gln Asn Asp Val Asp Ala Leu Gln Phe Leu Pro Ser
                325                 330                 335
```

Gly Phe Leu Glu Arg Thr Lys Glu Glu Gly Phe Val Ile Thr Ser Trp
                340                 345                 350

Ala Pro Gln Ile Gln Ile Leu Ser His Ser Ser Val Gly Gly Phe Leu
            355                 360                 365

Ser His Cys Gly Trp Ser Ser Thr Leu Glu Ser Val Val His Gly Val
        370                 375                 380

Pro Leu Ile Thr Trp Pro Met Phe Ala Glu Gln Gly Met Asn Ala Val
385                 390                 395                 400

Leu Val Thr Glu Gly Leu Lys Val Gly Leu Arg Pro Arg Val Asn Glu
                405                 410                 415

Asn Gly Ile Val Glu Arg Val Glu Val Ala Lys Val Ile Lys Arg Leu
            420                 425                 430

Met Glu Gly Glu Cys Glu Lys Leu His Asn Asn Met Lys Glu Leu
        435                 440                 445

Lys Glu Val Ala Ser Asn Ala Leu Lys Glu Asp Gly Ser Ser Thr Lys
    450                 455                 460

Thr Ile Ser Gln Leu Thr Leu Lys Trp Arg Asn Leu Val Gln Lys Asn
465                 470                 475                 480

Gln Ile

<210> SEQ ID NO 2
<211> LENGTH: 1449
<212> TYPE: DNA
<213> ORGANISM: Medicago truncatula

<400> SEQUENCE: 2

```
atgaacttgg cctcaaattt catggataaa acaattcaca ttgccgttgt tccaggtgtc      60
gggtatggac acttagtccc tattcttcat ttctcaaagt tacttatcca gcttcatccg     120
gacattcatg tcacatgtat cattcccaca cttggttctc ccccaagttc ctcagaaacc     180
atccttcaaa cccttccatc aaatatcgac tacatgtttc ttccagaggt tcaacctagt     240
gacctaccac aaggactgcc catgaaaatc caaattcagc tcacagttac taattctctc     300
ccatatttgc atgaggcatt gaagtctctt gctttaagga ttccccttgt ggccttggtg     360
gttgatgctt tgctgttga agcactaaac tttgctaaag aattcaacat gttgtcctat     420
atatactttt gtgcagcagc tagtacactg gcttggagct tctatttgcc taagttggat     480
gaggaaacaa catgtgagta cagagatctc ccagagccta tcaaagtacc gggctgcgta     540
ccactccatg gcaggatct cttgaccata gttcaagata gatcaagtca agcttacaaa     600
tacttccttc aacatgttaa aagtttaagt tttgctgatg gtgttcttgt taatagcttc     660
ttagaaatgg aaatgggacc tataaatgca ttgacagagg aaggaagtgg caaccttct     720
gtctatcctg ttggacccat catccagaca gtaacaggtt ctgttgatga tgctaatggt     780
ttggagtgtc tgtcatggtt agacaaacaa caatcttgtt cagttttgta tgtgtctttc     840
ggtagtggtg gtacactttc acacgaacaa attgttgagc tggctttggg tttggaattg     900
agtaatcaga aattcctatg ggttgtgcga gcaccaagta gtagttcatc taatgcagca     960
tatcttttcag cacaaaatga tgttgatgct ttacaatttt taccatctgg gttttggag    1020
agaaccaaag aggaaggttt tgtcattaca tcatgggcac ctcagattca aatccttagt    1080
catagttcag ttgcgggtt cttgagtcac tgtggttgga gctcaacact tgaaagtgtg    1140
gttcatgggg tgccactaat cacatggcct atgtttgctg aacagggaat gaatgcagtt    1200
ttggtgactg agggccttaa agtgggactg aggccaagag ttaacgaaaa tggtattgtc    1260
```

-continued

```
gaaagggtgg aggttgctaa ggtgatcaag cgtctcatgg aaggagaaga gtgtgagaaa    1320
ttgcacaata atatgaagga attaaaagaa gttgcttcta atgcactcaa agaagatgga    1380
tcttctacaa agactatttc tcaattaaca ctcaagtgga gaatttggt gcagaaaaac    1440 cagatttaa                                                            1449
```

<210> SEQ ID NO 3
<211> LENGTH: 875
<212> TYPE: PRT
<213> ORGANISM: Artificial Sequence
<220> FEATURE:
<223> OTHER INFORMATION: MBP-UGT72L1 fusion protein

<400> SEQUENCE: 3

```
Met Lys Ile Glu Glu Gly Lys Leu Val Ile Trp Ile Asn Gly Asp Lys
 1               5                  10                  15

Gly Tyr Asn Gly Leu Ala Glu Val Gly Lys Lys Phe Glu Lys Asp Thr
                20                  25                  30

Gly Ile Lys Val Thr Val Glu His Pro Asp Lys Leu Glu Glu Lys Phe
            35                  40                  45

Pro Gln Val Ala Ala Thr Gly Asp Gly Pro Asp Ile Ile Phe Trp Ala
        50                  55                  60

His Asp Arg Phe Gly Gly Tyr Ala Gln Ser Gly Leu Leu Ala Glu Ile
 65                  70                  75                  80

Thr Pro Asp Lys Ala Phe Gln Asp Lys Leu Tyr Pro Phe Thr Trp Asp
                 85                  90                  95

Ala Val Arg Tyr Asn Gly Lys Leu Ile Ala Tyr Pro Ile Ala Val Glu
            100                 105                 110

Ala Leu Ser Leu Ile Tyr Asn Lys Asp Leu Leu Pro Asn Pro Pro Lys
        115                 120                 125

Thr Trp Glu Glu Ile Pro Ala Leu Asp Lys Glu Leu Lys Ala Lys Gly
    130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
            180                 185                 190

Leu Thr Phe Leu Val Asp Leu Ile Lys Asn Lys His Met Asn Ala Asp
        195                 200                 205

Thr Asp Tyr Ser Ile Ala Glu Ala Ala Phe Asn Lys Gly Glu Thr Ala
    210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
            260                 265                 270

Asn Lys Glu Leu Ala Lys Glu Phe Leu Glu Asn Tyr Leu Leu Thr Asp
        275                 280                 285

Glu Gly Leu Glu Ala Val Asn Lys Asp Lys Pro Leu Gly Ala Val Ala
    290                 295                 300

Leu Lys Ser Tyr Glu Glu Glu Leu Ala Lys Asp Pro Arg Ile Ala Ala
305                 310                 315                 320

Thr Met Glu Asn Ala Gln Lys Gly Glu Ile Met Pro Asn Ile Pro Gln
                325                 330                 335
```

```
Met Ser Ala Phe Trp Tyr Ala Val Arg Thr Ala Val Ile Asn Ala Ala
        340                 345                 350

Ser Gly Arg Gln Thr Val Asp Glu Ala Leu Lys Asp Ala Gln Thr Asn
        355                 360                 365

Ser Ser Ser Asn Asn Asn Asn Asn Asn Asn Asn Asn Asn Leu Gly Ile
    370                 375                 380

Glu Gly Arg Ile Ser Glu Phe Gly Ser Met Asn Leu Ala Ser Asn Phe
385                 390                 395                 400

Met Asp Lys Thr Ile His Ile Ala Val Val Pro Gly Val Gly Tyr Gly
                405                 410                 415

His Leu Val Pro Ile Leu His Phe Ser Lys Leu Leu Ile Gln Leu His
                420                 425                 430

Pro Asp Ile His Val Thr Cys Ile Ile Pro Thr Leu Gly Ser Pro Pro
            435                 440                 445

Ser Ser Ser Glu Thr Ile Leu Gln Thr Leu Pro Ser Asn Ile Asp Tyr
    450                 455                 460

Met Phe Leu Pro Glu Val Gln Pro Ser Asp Leu Pro Gln Gly Leu Pro
465                 470                 475                 480

Met Glu Ile Gln Ile Gln Leu Thr Val Thr Asn Ser Leu Pro Tyr Leu
                485                 490                 495

His Glu Ala Leu Lys Ser Leu Ala Leu Arg Ile Pro Leu Val Ala Leu
            500                 505                 510

Val Val Asp Ala Phe Ala Val Glu Ala Leu Asn Phe Ala Lys Glu Phe
        515                 520                 525

Asn Met Leu Ser Tyr Ile Tyr Phe Cys Ala Ala Ala Ser Thr Leu Ala
        530                 535                 540

Trp Ser Phe Tyr Leu Pro Lys Leu Asp Glu Thr Thr Cys Glu Tyr
545                 550                 555                 560

Arg Asp Leu Pro Glu Pro Ile Lys Val Pro Gly Cys Val Pro Leu His
                565                 570                 575

Gly Arg Asp Leu Leu Thr Ile Val Gln Asp Arg Ser Ser Gln Ala Tyr
            580                 585                 590

Lys Tyr Phe Leu Gln His Val Lys Ser Leu Ser Phe Ala Asp Gly Val
        595                 600                 605

Leu Val Asn Ser Phe Leu Glu Met Glu Met Gly Pro Ile Asn Ala Leu
        610                 615                 620

Thr Glu Glu Gly Ser Gly Asn Pro Ser Val Tyr Pro Val Gly Pro Ile
625                 630                 635                 640

Ile Gln Thr Val Thr Gly Ser Val Asp Asp Ala Asn Gly Leu Glu Cys
                645                 650                 655

Leu Ser Trp Leu Asp Lys Gln Gln Ser Cys Ser Val Leu Tyr Val Ser
            660                 665                 670

Phe Gly Ser Gly Gly Thr Leu Ser His Glu Gln Ile Val Glu Leu Ala
        675                 680                 685

Leu Gly Leu Glu Leu Ser Asn Gln Lys Phe Leu Trp Val Val Arg Ala
        690                 695                 700

Pro Ser Ser Ser Ser Asn Ala Ala Tyr Leu Ser Ala Gln Asn Asp
705                 710                 715                 720

Val Asp Ala Leu Gln Phe Leu Pro Ser Gly Phe Leu Glu Arg Thr Lys
                725                 730                 735

Glu Glu Gly Phe Val Ile Thr Ser Trp Ala Pro Gln Ile Gln Ile Leu
            740                 745                 750

Ser His Ser Ser Val Gly Gly Phe Leu Ser His Cys Gly Trp Ser Ser
```

```
                    755                 760                 765
Thr Leu Glu Ser Val Val His Gly Val Pro Leu Ile Thr Trp Pro Met
    770                 775                 780

Phe Ala Glu Gln Gly Met Asn Ala Val Leu Val Thr Glu Gly Leu Lys
785                 790                 795                 800

Val Gly Leu Arg Pro Arg Val Asn Glu Asn Gly Ile Val Glu Arg Val
                805                 810                 815

Glu Val Ala Lys Val Ile Lys Arg Leu Met Glu Gly Glu Cys Glu
            820                 825                 830

Lys Leu His Asn Asn Met Lys Glu Leu Lys Glu Val Ala Ser Asn Ala
                835                 840                 845

Leu Lys Glu Asp Gly Ser Ser Thr Lys Thr Ile Ser Gln Leu Thr Leu
    850                 855                 860

Lys Trp Arg Asn Leu Val Gln Lys Asn Gln Ile
865                 870                 875

<210> SEQ ID NO 4
<211> LENGTH: 2628
<212> TYPE: DNA
<213> ORGANISM: Artificial Sequence
<220> FEATURE:
<223> OTHER INFORMATION: Synthetic MBP-UGT72L1 nucleotide sequence

<400> SEQUENCE: 4
atgaaaatcg aagaaggtaa actggtaatc tggattaacg gcgataaagg ctataacggt      60
ctcgctgaag tcggtaagaa attcgagaaa gataccggaa ttaaagtcac cgttgagcat     120
ccggataaac tggaagagaa attcccacag gttgcggcaa ctggcgatgg ccctgacatt     180
atcttctggg cacacgaccg ctttggtggc tacgctcaat ctggcctgtt ggctgaaatc     240
accccggaca agcgttcca ggacaagctg tatccgtttta cctgggatgc cgtacgttac     300
aacggcaagc tgattgctta cccgatcgct gttgaagcgt atcgctgat ttataacaaa     360
gatctgctgc cgaacccgcc aaaaacctgg gaagagatcc cggcgctgga taagaactg      420
aaagcgaaag gtaagagcgc gctgatgttc aacctgcaag aaccgtactt cacctggccg     480
ctgattgctg ctgacggggg ttatgcgttc aagtatgaaa acggcaagta cgacattaaa     540
gacgtgggcg tggataacgc tggcgcgaaa gcgggtctga ccttcctggt tgacctgatt     600
aaaaacaaac acatgaatgc agacaccgat tactccatcg cagaagctgc ctttaataaa     660
ggcgaaacag cgatgaccat caacggcccg tgggcatggt ccaacatcga caccagcaaa     720
gtgaattatg gtgtaacggt actgccgacc ttcaagggtc aaccatccaa accgttcgtt     780
ggcgtgctga gcgcaggtat taacgccgcc agtccgaaca aagagctggc aaaagagttc     840
ctcgaaaact atctgctgac tgatgaaggt ctggaagcgg ttaataaaga caaaccgctg     900
ggtgccgtag cgctgaagtc ttacgaggaa gagttggcga agatccacg tattgccgcc    960
actatggaaa acgcccagaa aggtgaaatc atgccgaaca tcccgcagat gtccgctttc    1020
tggtatgccg tgcgtactgc ggtgatcaac gccgccagcg tcgtcagac tgtcgatgaa    1080
gccctgaaag acgcgcagac taattcgagc tcgaacaaca caacaataa caataacaac    1140
aacctcggga tcgagggaag gatttcagaa ttcggatcca tgaacttggc ctcaaatttc    1200
atggataaaa caattcacat tgccgttgtt ccaggtgtcg ggtatggaca cttagtccct    1260
attcttcatt tctcaaagtt acttatccag cttcatccgg acattcatgt cacatgtatc    1320
attcccacac ttggttctcc cccaagttcc tcagaaacca tccttcaaac ccttccatca    1380
aatatcgact acatgtttct tccagaggtt caacctagtg acctaccaca aggactgccc    1440
```

```
atggaaatcc aaattcagct cacagttact aattctctcc catatttgca tgaggcattg    1500
aagtctcttg ctttaaggat tcccttgtg gccttggtgg ttgatgcttt tgctgttgaa     1560
gcactaaact tgctaaaga attcaacatg ttgtcctata tatacttttg tgcagcagct     1620
agtacactgg cttggagctt ctatttgcct aagttggatg aggaaacaac atgtgagtac    1680
agagatctcc cagagcctat caaagtaccg ggctgcgtac cactccatgg cagggatctc    1740
ttgaccatag ttcaagatag atcaagtcaa gcttacaaat acttccttca acatgttaaa    1800
agtttaagtt ttgctgatgg tgttcttgtt aatagcttct tagaaatgga atgggacct    1860 ataaatgcat tgacagagga aggaagtggc aacccttctg tctatcctgt tggacccatc    1920
atccagacag taacaggttc tgttgatgat gctaatggtt tggagtgtct gtcatggtta    1980
gacaaacaac aatcttgttc agttttgtat gtgtctttcg gtagtggtgg tacactttca    2040
cacgaacaaa ttgttgagct ggctttgggt ttggaattga gtaatcagaa attcctatgg    2100
gttgtgcgag caccaagtag tagttcatct aatgcagcat atctttcagc acaaaatgat    2160
gttgatgctt tacaattttt accatctggg tttttggaga aaccaaaga ggaaggtttt     2220 gtcattacat catgggcacc tcagattcaa atccttagtc atagttcagt tggcgggttc    2280
ttgagtcact gtggttggag ctcaacactt gaaagtgtgg ttcatggggt gccactaatc    2340
acatggccta tgtttgctga cagggaatg aatgcagttt tggtgactga gggccttaaa     2400
gtgggactga ggccaagagt taacgaaaat ggtattgtcg aaagggtgga ggttgctaag    2460
gtgatcaagc gtctcatgga aggagaagag tgtgagaaat gcacaataa tatgaaggaa     2520 ttaaaagaag ttgcttctaa tgcactcaaa gaagatggat cttctacaaa gactatttct    2580
caattaacac tcaagtggag aaatttggtg cagaaaaacc agatttaa                 2628

<210> SEQ ID NO 5
<211> LENGTH: 1017
<212> TYPE: DNA
<213> ORGANISM: Medicago truncatula

<400> SEQUENCE: 5
atggctagta tcaaacaaat agaaatagaa aagaagaagg catgtgtgat aggtggcact     60
ggttttgtgg catcattgct gatcaagcag ttgcttgaaa agggttatgc tgttaatact    120
actgttagag acctagatag tgcaaacaaa acatctcacc tcatagcact gcaaagtttg    180
ggggaactga atctatttaa agcagaatta acaattgaag aagatttga tgctcctata     240 tcaggatgtg aacttgtctt ccaacttgct acacctgtga actttgcttc tcaagatcct    300
gagaatgaca tgataaaacc agcaatcaaa ggtgtattga atgtgttgaa agcatgtgta    360
agagcaaaag aagtcaaaag agttatctta acatcttcag cagctgctgt gactataaac    420
gaactcgaag ggactggtca tgttatggat gaaaccaatt ggtctgatgt tgagtttttg    480
aacactgcaa agccacccac ttggggttat cctgtttcaa aagtactagc tgaaaaggct    540
gcgtggaaat ttgctgaaga aaataacatt gatctaatca ctgtgatacc tactctaaca    600
attggtcctt ctctaactca agatatccca tctagtgttg ccatgggaat gtcacttcta    660
acaggcaatg atttcctcat aaatgctttg aaaggaatgc agtttctatc gggttcaata    720
tcaattactc atgtcgagga tatttgtcgg gctcatattt ttgtggcaga gaagaatca    780 acttctggtc gatacatttg ctgtgctcac aataccagtg ttcccgagct tgcaaagttt    840
ctcagcaaac gataccctca gtataaagtt ccaactgaat ttgatgattt ccccagcaag    900
gcaaagttga taatctcttc tggaaagctt atcaaagaag gtttcagttt caagcatagt    960
```

```
attgctgaaa cttttgacca aactgtggag tatttgaaga ctcaggggat caagtga        1017
```

<210> SEQ ID NO 6
<211> LENGTH: 1331
<212> TYPE: DNA
<213> ORGANISM: Medicago truncatula

<400> SEQUENCE: 6

```
gccaaccaaa atcactagag aaaaaaaaat cagggaaaaa acagagaaaa taaaatatgg      60
gttctatggc cgaaactgtt tgtgtcacag gggcttcagg ttttatcggg tcatggcttg     120
tcatgagact tatggagcgc ggttacatgg ttcgagcaac agtccgcgac ccagaaaact     180
tgaagaaggt gagtcatttg ttagaactgc caggtgcaaa gggcaaactg tccctatgga     240
aggctgacct tggtgaagag ggtagttttg atgaagctat taaagggtgt acaggagttt     300
ttcatgttgc tactcctatg gattttgagt ccaaggaccc tgagaatgaa atgatcaagc     360
ctaccataaa agggtgctga acatcatga agcatgcct caaggccaaa actgtccgta      420
gatttatttt cacatcatcg gccggaaccc taaacgttac tgaagatcaa agcccttgt     480
gggatgaaag ctgttggagt gatgttgagt tttgtaggag agtgaagatg actggctgga     540
tgtattttgt ttcaaagaca cttgcggagc aagaagcatg gaaatttgcc aaagagcaca     600
acatggattt catcacaatc atcccacctc ttgttgttgg ccttttcctt attcctacca     660
tgccacctag cctaatcact gcccttcctc ctatcactgg aaatgaagct cattattcga     720
ttataaagca aggccaattc gtccacttgg atgatctttg tgaagctcac atattcttgt     780
ttgagcatat ggaagtagaa gggaggtatc tatgtagtgc atgtgaagct aatattcatg     840
acattgcaaa attaattaat acaaaatatc cagagtacaa tatccccaca agttcaata     900
atattccaga tgaattggag cttgtgagat tttcatcaaa gaagatcaaa gacttgggat     960
tcgagtttaa atacagcttg gaggatatgt acactgaagc aattgataca tgcatagaaa    1020
aagggcttct tcctaaattt gttaaaagca ccaataagta atggtgtcac acataaataa    1080
ataagtatag ctatgtgtc tttatgtgtg tttctgtgat ggcttaagga tcttacttaa     1140
ttccttgaga ttttctttag tagctggaat gtttgtgcaa tcctgttgaa gcccaaactt    1200
acttgaatgt tttctatctc tttcatttgt tccttattga gagctacacg aaaaaggaaa    1260
agataatgaa ttattgaata ttatttattt gcaaaatgtt gaaagcttaa aaaaaaaaaa    1320
aaaaaaaaa a                                                          1331
```

<210> SEQ ID NO 7
<211> LENGTH: 1248
<212> TYPE: DNA
<213> ORGANISM: Medicago truncatula

<400> SEQUENCE: 7

```
gcgcccatgg gttcagtctc agaaacagtt tgcgtcacag gggcttcagg tttcatcggg      60
tcgtggcttg ttatgagact tatggagcgc ggctacacag ttcgagccac cgtgcgcgac     120
ccagataaca tgaagaaggt gaagcatttg ttggaactgc caggtgcaaa tagcaaacta     180
tctctttgga aggctgacct tggggaagag ggtagttttg atgaagctat taaagggtgt     240
acaggagttt ttcatgttgc tactcctatg gattttgagt ccaaggaccc cgagaaggaa     300
gtgataaacc ctacaataaa tggattacta gacataatga aagcatgtaa gaaggcaaaa     360
acagttagaa gattggtttt cacatcatca gctggaactt tggatgttac tgagcaacaa     420
aattctgtaa ttgatgaaac ttgctggagt gacgtcgaat tctgccgtag agtcaagatg     480
```

```
actggttgga tgtattttgt ttcaaaaacc ctggcagaac aagaagcatg gaagttttcc      540
aaagaacaca acatagactt tgtttccatt attccacctc ttgttgttgg tccatttatt      600
atgccttcaa tgccaccgag tctaatcact gctctttccc ttatcacagg atatgaggct      660
cattactcga tcataaagca aggccaatac atccacttag acgacctttg tcttgctcat      720
atatttctgt ttgagaaccc taaagcacat gggagataca tatgttgttc acatgaggca      780
accattcatg aagttgcaaa acttattaac aaaaaatacc ctgagttcaa tgtccctaca      840
aaattcaagg atatcccaga tgatctggaa attatcaaat tttcttcaaa gaagatcaca      900
gacttggggt ttatatttaa atacagctta gaagacatgt tcacaggagc tatagaaacc      960
tgcagagaaa aagggctact tcctaaagtt acagagactc cggttaatga taccatgaag     1020
aaataaatat gcttttgtgt ctttgatgga ttgtgtctct ttttccttt tcatttgtgt      1080 tttttttttt aaggatcctt tttcatatgt tattaactaa ggtttatgtt atatgatgtc     1140
actcataata atattcatgt ttatgggtca cgttgtctgt taattatata agaactataa     1200
tgatatatgc tatattgctt ctaaatttac aaaaaaaaaa aaaaaaaa                  1248

<210> SEQ ID NO 8
<211> LENGTH: 950
<212> TYPE: DNA
<213> ORGANISM: Medicago sativa

<400> SEQUENCE: 8
gaattcccat agctaaacaa aaaaaattaa gaacaagaat atggctgcat caatcaccgc       60
aatcactgtg gagaaccttg aatacccagc ggtggttacc tctccggtca ccggcaaatc      120
atatttcctc ggtggcgctg gggagagagg attgaccatt gaaggaaact tcatcaagtt      180
cactgccata ggtgtttatt tggaagatat agcagtggct tcactagctg ccaaatggaa      240
gggtaaatca tctgaagagt tacttgagac ccttgacttt tacagagaca tcatctcagg      300 tcccttttgaa aagttaatta gagggtcaaa gattagggaa ttgagtggtc ctgagtactc      360
aaggaaggtt atggagaact gtgtggcaca cttgaaatca gttggaactt atggagatgc      420
agaagctgaa gctatgcaaa aatttgctga agctttcaag cctgttaatt ttccacctgg      480
tgcctctgtt ttctacaggc aatcacctga tggaatatta gggcttagtt tctctccgga      540
tacaagtata ccagaaaagg aggctgcact catagagaac aaggcagttt catcagcagt      600
gttggagact atgatcggcg agcacgctgt tccccctgat cttaagcgct gtttagctgc      660
aagattacct gcgttgttga acgagggtgc tttcaagatt ggaaactgat gatgattata      720
ctcctatatc actgcatttc caaaagcgtt gcagcacaag aatgagacca tgaacttttt      780
taagtctaca cgtttaattt tttgtatatc tatttacctt cttattagta tcaataatat      840
gaaatgaaag atcttgcttt ctactcttgt actatttctg tgatagataa tgttaatgag      900
tatcttcatc aataaagtg atttgttttg tttgttcaaa aaaaaaaaa                   950

<210> SEQ ID NO 9
<211> LENGTH: 836
<212> TYPE: DNA
<213> ORGANISM: Medicago sativa

<400> SEQUENCE: 9
caaatcatat ttcctcggtg gcgctgggga gaggattg accattgaag gaaacttcat        60
caagttcact gccataggtg tttatttgga agatatagca gtggcttcac tagctgccaa      120 atggaaggt aaatcatctg aagagttact tgagaccctt gacttttaca gagacatcat      180
```

```
ctcaggtccc tttgaaaagt taattagagg gtcaaagatt agggaattga gtggtcctga      240
gtactcaagg aaggttatgg agaactgtgt ggcacacttg aaatcagttg aacttatgg       300 agatgcagaa gctgaagcta tgcaaaaatt tgctgaagct ttcaagcctg ttaatttcc       360 acctggtgcc tctgttttct acaggcaatc acctgatgga atattagggc ttagtttctc      420
tccggataca agtataccag aaaaggaggc tgcactcata gagaacaagg cagtttcatc      480
agcagtgttg gagactatga tcggcgaaca cgctgtttcc cctgatctta agcgctgttt      540
ggctgcaaga ttacctgcgt tgttgaacga gggtgctttc aagattggaa actgatgatg     600
attatactct tatataaaaa catttccaaa agcgttgcag cacaagaatg agaccatgga      660
cttttttaag tctacacgtt taattttttg tatatctatt taccttctta ttagtatcaa      720
tagtatgaaa tgaaagatct tgcttctac tcttgtacta tttctgtgat agataatgtt       780
aatgagtatc ttcatcaata aaagtgattt gttttgtttg ttcaaaaaaa aaaaaa         836

<210> SEQ ID NO 10
<211> LENGTH: 1380
<212> TYPE: DNA
<213> ORGANISM: Medicago sativa

<400> SEQUENCE: 10
gaattcccaa caacaagta ctgcaaacca attgagtatt acatagaaac tactagagat        60
accaagatgg tgagtgtatc tgaaattcgc aaggctcaga gggcagaagg tcctgcaacc     120
attttggcca ttggcactgc aaatccagca aattgtgttg aacaaagtac atatcctgat     180
ttttacttta aaatcacaaa tagcgagcac aagactgaac tcaaagagaa attccaacgc    240
atgtgtgata atctatgat caagaggaga tacatgtacc taacagagga gattttgaaa      300
gagaatccta gtgtttgtga atatatggca ccttcattgg atgccaggca agacatggtg     360
gtggtagagg tacctagact agggaaggag gctgcagtga aggctataaa agaatggggt     420
caaccaaagt caaagattac tcacttaatt gtttgcacta caagtggtgt agacatgcct     480
ggagctgatt accaactcac aaaactcttg ggtcttcgcc catatgtgaa aaggtatatg      540
atgtaccaac aaggttgctt tgcaggaggc acggtgcttc gtttggctaa agatttggct     600
gagaacaaca aaggtgcccg tgtattggtt gtttgttctg aagtcactgc agtcacattc      660
cgcggcccta gtgatactca cttggacagc cttgttggac aagcactatt tggagacgga     720
gctgctgcac taattgttgg ttctgatcca gtaccagaaa ttgagaaacc tatatttgag     780
atggtttgga ctgcacaaac aattgctcca gatagtgaag agccattga tggtcacctt       840 cgtgaagctg gactaacatt ccaccttctt aaagatgttc ctgggattgt tcaaagaac      900 attgataaag cattagttga agctttccaa ccattgggaa tttctgatta caactcaatc      960
ttttggattg cacaccctgg tggccctgca atttttagatc aagtagagca aaagttagcc   1020
ttgaagcctg aaaagatgag agccactaga gaagtgctta gtgaatatgg aaatatgtca    1080
agtgcatgtg ttttgtttat cttagatgaa atgagaaaga aatcaactca agatggactg     1140
aagacaacag gagaaggact tgaatggggt gtgttatttg gctttggacc aggacttacc     1200
atagaaactg ttgttttgcg cagtgtcgct atatgaaatg cttaattatt ttatttttat      1260
ttatcacttt caaatttgct tgattttat gtaaggatga aaaactcgtc tacagttcaa       1320
catttactgt catattaaaa ataatacaat tgtgattccc tttaaaaaaa aaaggaattc     1380

<210> SEQ ID NO 11
<211> LENGTH: 1423
```

```
<212> TYPE: DNA
<213> ORGANISM: Medicago sativa

<400> SEQUENCE: 11
cgaattccca actaagtact gtaaaccata gagttcaaat tacagtactt tactttcatt      60
tgataccaac ctaccatatc attgctacac agaaactata tcaagatggt gagtgtatct     120
gaaattcgtc aggctcaaag ggcagaaggc cctgcaacca tcatggccat tggcactgca     180
aatccatcca actgtgttga acaaagcaca tatcctgatt tctacttcaa aatcacaaac     240
agtgagcaca aagttgaact caaagagaaa tttcaacgca tgtgtgataa atccatgatc     300
aagaggagat acatgtatct taccgaagag attttgaaag aaaatccaag tgtatgtgaa     360
tacatggcac cttcattgga tgctaggcag gacatggtgg tggtagaggt acctagactt     420
ggaaaggagg ctgcagtgaa ggctataaaa gaatggggcc aaccaaaatc aaagattaca     480
cacttaatat tttgtaccac aagtggtgta gacatgcctg gtgccgatta ccaactcaca     540
aaactcttag gtcttcgtcc atatgtgaaa aggtatatga tgtaccaaca agggtgcttt     600
gcaggtggga cggtccttcg tttggccaag gacttggctg agaacaataa aggtgctcgt     660
gtgttggttg tttgttctga agttactgcg gtgacattcc gtggtcctag tgatactcat     720
ttagacagtc ttgttggaca agcactcttt ggagatggtg ctgctgcact cattgttggt     780
tctgacccaa taccagaaat tgagaaacct atatttgaga tggtttggac tgcacaaaca     840
attgctccag acagtgaagg agccattgat ggtcaccttg tcgaagctgg tctaacattt     900
caccttctta aagatgttcc tgggattgtt tcaaagaaca ttgataaagc attgattgag     960
gctttccaac cattaaacat ctctgattac aattcaatct tctggattgc tcacccaggt    1020
ggacccgcaa ttctagacca agttgaagaa agttaggct taaaacctga aaagatgaag    1080
gccactaggg aagtacttag tgaatatggt aacatgtcaa gtgcatgtgt attgttcatc    1140
ttagatgaga tgagaaagaa atcggcacaa gcgggactta aaaccacagg agaaggcctt    1200
gactggggtg tgttgtttgg cttcggacct ggacttacca ttgaaaccgt tgttctccat    1260
agcgtggcta tatgaaatga ttgattgttt tattttattg tattacttt aaacttgctt    1320
gaaattccat gtaagaataa atacagagtt catgtaccat ggatgttaaa acgaatatac    1380
catttgtagc ttcttctttt tctcgcaaaa aaaaaaggaa ttc                      1423

<210> SEQ ID NO 12
<211> LENGTH: 7918
<212> TYPE: DNA
<213> ORGANISM: Arabidopsis thaliana

<400> SEQUENCE: 12
ggtaccttag attatccaaa tttgtagctg caaaagttgt tcctgtgttc aagaaagaaa      60
gacctgtaaa atgatctgga tgtgtttggt tatatatata agaagactta aaagataatg     120
acttaatctc gtaacgagtc acacggacgt gacgctgaaa ctcacacacg ttggtgccac     180
gtctttgtct ttcctctttt gctctacttt tttctcctca taggtgatag gtcccataag     240
caatgaaata aaaaaaatgg taattgactt ttctccaaac attttcgaat ctgatttct      300
ttttcaaggt tttataacct ctacattcca gaatatgact aatgacatca ttatccaatt     360
attttttata ctgtaaactc attattatga atattcttta tttcaaaaaa ttaccattga     420
tttataagtt tattagtata atatataaca tatggaataa aacttttatt taaaaaaaaa     480
tatttttccc caaaaaaagt aggattaata acctgattaa taaataaaaa gtgttatatt     540
tttaagcatt gtatgcattt actttatcat agttgtcttg tttttaagag ttaaaaaata     600
```

```
atgatgaaca atttcacgga caacgattcc acgataaagc tttccctgca acactcagat      660
tttctaaaga cggttttgca ttgcgttttc tgggattcga aacccaaaca tgatgtacaa      720
gtattaatga actcttagtt aaccattaga ttaaaaatat tttcactatt aattttctct      780
taaaaatatt aataattttt tgaaatcaaa aattatagtt attttatttt aataaacgag      840
aaacactaca aaaaagtta actgcattta gataatttaa taaactaaaa tatccacata       900
aaaatttcaa atttatcaaa aataaaacat caatttgttt tttgttttaa attaaagatt      960
tgctattgat tgcataagga agaaaacttt acaaagccga aaggcctaag agcccaacac     1020
acacaaaaga agaaccattt tggatcaagg gaaccgacca tgggtattag aagtagtggt     1080
ataaagccca tcatatccca acacataacc cacgaatgtt taatattaaa agtttgttgt     1140
tcggctcatg attagcgatg atcatacaga aagtttgtat ctaatacgtg ccttgaattt     1200
tatgtgtaca acaaacaaat taaattattc aaaaccataa attataaaaa ataattacag     1260
aaataaaact atattaagag cgagcctacc atccggtgtg caactttcta gtttatatac     1320
agtggcggat caacgttaat gaggcaaatt ggttcaaatt catctaaata agactagagt     1380
tcacaggttc gattcctcct tataacaatt tgctcccacc aatttttttt gctgggtccg     1440
cccctggtta tatatatact tctacaccag gtttgggttc gagtccacac ataattaacg     1500
acacaattat agtgcacgat agaatgaact aaaacagcta gagcgtagag ggctcattgt     1560
ctataaaaat ccttcgttaa cttgcaagaa accaagagta gagggctcac acttaagtct     1620
cctacatgac gattatattt cgtcaaaaag aagcaattag ttagctttac agcatatcat     1680
ttcgcctagg ttttccatcg tacacgtaaa ttttcatgca agaaagcaga aatatacaaa     1740
tactaacttt tagatactga aaatgagat cagattctag tcaaattttg ttaaaagtat      1800
ttataaattt aaattgcaag tcctcaaaaa gtacgactaa aaatgctttt cttagaaaat     1860
gataataaac cggcgtttta tatataagtg tttcttttc tcttctgtcc agaagtaaat      1920
cattaagaac caatatggct tttcttaaac taatctccgt gataatcaaa tctttgatca     1980
ttctccacac aatcccatca acaacatcga tctcactaga tgcaccaaca atgattctaa     2040
tcggcactac taactataga gatagttgtc ccaaaaaaaa aaaaaaaaac taactagaga     2100
gataaatcat attcaataca tgtactattt ctactatact taagaaaatt tgtataccac     2160
tatcttaact cttaacactg aacatactat acactatctt aactcccaac tcttgtaaaa     2220
gaatatctaa ttttaagaaa agacttcaaa tgcttgttaa atttctagtg aagatgcaca     2280
ttctaaaaac tggtaaaatg gtaagaaaaa aatatataaa aaaatagcct tattaaaatt     2340
tatatctcct atttctctat ccaaactaca cggatgaagc ttattgttat tcatccaccc     2400
tttttctcaa ttctgtccta tttcttgtgc atgaaacttc tccatcttgt aatcggataa     2460
atcatacca aatttttcct ttctgaaaac atatataccc gaacattaat tactatcgtc      2520
ctttctccta attttgttaa gaaacatgtt tgtttgtttt tagtactgaa aaaggatgga     2580
gatacttgct agatcctatg aaccttttct ctctaggaca aatcagtaac caaacaataa     2640
cttagcaaat taagcacgac agctaataca taaaatgtgg atatcaaaca tgcacgtcac     2700
ttccttttttt ccgtcacgtg ttttataaa ttttctcaca tactcacact ctctataaga     2760
cctccaatca tttgtgaaac catactatat ataccctctt ccttgaccaa tttacttata     2820
cctttttacaa tttgtttata tattttacgt atctatcttt gttccatgga gggttcgtcc     2880
aaagggctgc gaaaaggtgc ttggactact gaagaagata gtctcttgag acagtgcatt     2940
aataagtatg gagaaggcaa atggcaccaa gttcctgtaa gagctggtat gttatttacg     3000
```

```
aacacacaca cactaaccga cacacacaca cacaaatatg aatatctata atcactacca   3060
atagtcttcg ttctctctat tttctattca gaaaattgat taatacccgg tattaaaaaa   3120
aaaaaaaaaa atttgtttaa atgagtacaa atcattgtta caacttcttt atgctgtttt   3180
tacatgctat taaaggttgt gcatgaaaat ttcttttgct gttcgtattt gttttacacc   3240
taaacgaaga ttttttactta aaattaaaga aaaaaaatta tactaatttt agttacgttg    3300
cgtattgcta gcttctccta taaagtcgtt caaattttta cacgcttgtc ttcttgtaaa   3360
tgaattcgtg ggaaaatttt gtatgaacac gtgtttctgt gttggaacag ttctttattt   3420
ttattggtgt gcatagattc ttcctgataa aatatataga aggagacaaa taaaaaacag   3480
tcttagtatg taggtataat caaagaatca attattggtt ttgtagggct aaaccggtgc   3540
aggaaaagtt gtagattaag atggttgaac tatttgaagc caagtatcaa gagaggaaaa   3600
cttagctctg atgaagtcga tcttcttctt cgccttcata ggcttctagg aataggtat    3660
taattgttac ctcgatacta cttaactcgg agagtcgtca taagttaata ctaataacat   3720
atgtatattt tcttacaatt gttaggtggt ctttaattgc tggaagatta cctggtcgga   3780
ccgcaaatga cgtcaagaat tactggaaca ctcatctgag taagaaacat gaaccgtgtt   3840
gtaagataaa gatgaaaaag agagacatta cgcccattcc tacaacaccg gcactaaaaa   3900
acaatgttta taagcctcga cctcgatcct tcacagttaa caacgactgc aaccatctca   3960
atgccccacc aaaagttgac gttaatcctc catgccttgg acttaacatc aataatgttt   4020
gtgacaatag tatcatatac aacaaagata agaagaaaga ccaactagtg aataatttga   4080
ttgatggaga taatatgtgg ttagagaaat tcctagagga aagccaagag gtagatattt   4140
tggttcctga agcgacgaca acagaaaagg gggacacctt ggcttttgac gttgatcaac   4200
tttggagtct tttcgatgga gagactgtga aatttgatta gtgtttcgaa catttgtttg   4260
cgtttgtgta taggttttgct ttcaccttt aatttgtgtg ttttgataaa taagctaata   4320
gttttttagca ttttaatgaa atatttcaag tttccgtgtt tacattttga agaaaataaa   4380
atattaatat attctgaaga ttttttgtttt ttttggtta tctacatgac aacagtaaaa   4440
atagaaaaaa aatcttatttt tttgaaaaag gtatgtatcc ggtgtttaga atactttccg   4500
aaatcaaacc gcctatattt ctaatcacta tgtaaaattg taaaccaatt gggttaaaac   4560
tcaactaaca aactttctaa ataaatgtca tttttgtttt caaatatgat tgaactcgga   4620
tttaggagtt ttaccttca gtaccaaacc ttctctaccg accatgtatg gttgggcaaa   4680
tgtcatgttt tacaatgttt agattactaa acactttggt tgagaaggca atgctttatt   4740
tatatattct gaagtcatgt tttagtgtta ttttttattta tttttaaatg catagattgt   4800
taacgtgcag attctcatat gggcttagtt tctggatttt gattatcaaa accgtattcc   4860
actcttaaat gattacgaca aaaaaatcaa tactactaac aaacctatttt cccagttatt   4920
aattagtcaa taacaattgt caaatttaat aacgtacttg ctagtaataa agttttaacg   4980
acgatcatag ataggttttt gaaacccata ctcgcagaag ttctgataca aaaatttgta   5040
ctccctctat ttcaaaatat taaatgttttt agataaaagc acaatgttta agaaactaat   5100
taatcttgag tttcttacat tataaacata aattaatatc tattaaaaat aatttgacca   5160
atgatataac ttacagcata atataaatag ttaaaaaaaa actgtttact ttaataattt   5220
gcataacaac tagctagtct ggtccaagaa cggtagtagg atgagatttt agaaggtcgt   5280
aatgtgtaag actaataatc atgcgataga cgatcatgca tgaattattt tatgtaatac   5340
ttatatggtt ccaaaatcta taagaaccct caattataaa agtaatatct attaaatatt   5400
```

```
taaacgataa tttcatacgg aaaattaata gataaattct tctatttgtt tttaaatata   5460
tgtaaatgcg aaagtgtccc atgcaatttt atatatttaa tcaagtgaaa actcgaaaac   5520
aaaaaacttg atgtacttca aacaagtttt tttggcaagt aatacccatt ctgttccggt   5580
tggactataa atgcatggaa aagcaccaaa aaaggcatgg atactttcgc gattttttgcc  5640 atttttgtat ctttgttcat cgctccgttc aaaagaacct cttgtcgtta ctataataag   5700
ttatggacca acggtattgt catgtatcaa ataactatg tagcatacgt gtattgtgaa    5760
tcaatgaagc aatagagaga taacatactg aaacgtccac atctcgttta taaaaaaatc   5820
gtctacatgc ttctctttgg ctggacatcc caacttttct caccgtaacc agtgaaattg   5880
tattatttgg taagaattac ggatggagtt agatttattt tgttgtgtgt gtataaatca   5940
atacttatac agtttttacg tgtataacgg cacgcctcat gggttttgct aataaggtcc   6000
aagtagtgga cagaaaagaa cttgtgattg aatagtgttt tgtattgaaa ggttaaaacg   6060
tgtttccaaa tggattcaac caaattccaa catgttcagt gtcgtacatg cgaaaacatt   6120
atcgagtaaa ataagttcca ttatacttg attttgtatt gattccatag agtagaaatg    6180
tgtgctttag cttatagtta aacactatct tcaaaggggt aatgctggat tcgaagtatt   6240
taattagtcc tgttcgaccg aatcaaagtt caatcgattt tgaaaaacaa tcatttcggg   6300
tatagcttga aacatcccaa accacaagtt ccaaaagcac acatattatc accattcaac   6360
taaccattcg ggtttgataa ccggtagttg gatgttcaaa gatctcatca gatttggtgt   6420
caagaggata attgtgattg agttgtgaac ccttgtgatg gagatagttt ccttgtttgg   6480
atgttaagtt gaattttggg atcatccttg tttcaaaaag actggaaaac acacaaaaaa   6540
aaaaaaaaaa aaacttgcaa ataaatttaa tttttagaaa ttttatattg tagtgaaaaa   6600
tgtttgcaaa ttttagctgg agatgttttt ccatttggaa ttttttttct taattttgcc   6660
ttttatttta cattgtatat tgctagcttc ttccttgacaa gaaagaacga tgtcaacctc   6720
tgatttgtct tcttataaat gaatttgttg aaaattgctg tacgagcaag tgttttttgtg  6780 ttggaacatg tctctatttc tattggtgtg catagattct tcatgataaa atatataagg   6840
agacaaataa gaaagcagtc ttattaggta ggattgccta aaatattcgt tagattcgct   6900
tggatctatt attcggttaa attgattcga aaaatctgaa tatccataat tttacgaagc   6960
aaatcaaata ttaaaaattg atattcgtta aaaacagaaa aaataacaaa tattaaattt   7020
aaataggcgg atatcctctc taattcggta tacatgaata tatgtatatg tatatagata   7080
agtataaata tatatattaa taatcttact cttttatat gtaagtttta gaagtttatg    7140
ttcatcaaat tagttattta actattagtt taaaaaattg aaaagagata ttttttccaa   7200 tgaagttta cttattttgg attaaatttc taattttat gttttaaatt tttataattg     7260
tttttgagat atacttaaca aatcgaatat ctagcaaata actcggattt taacggaata   7320
tctggacagc cggatattcg gttactttcg aaacaaatac gaatcagaaa actaattatt   7380
ccgatatagc aaatcggatc acaaatacta ccaaaatcca tgatatatgt gtcgtgtcca   7440
cccctattag taggtataat taattgtaat tagtggtttt gtaagactaa atcagcccag   7500
gaagagttgt agactaagat gcttatacta tttgaagcca agtatcaaga gaggaagatt   7560
taggctctga tgaagttgat cttcttcttc gccttcccaa ccttctagga aatagtattt   7620
gttatacttt atactaatta attacttcgg gattcataag attattaata acatattatt   7680
cgtataatgt ttaacaactt ttagattggc tttgattgct ggtctattgg ctggtcagac   7740
cacaaacggt gtcaaaaatt acttgaacac tcaactgagt aagaaacatg aaccatgttg   7800
```

```
taagatttag ataaaaaaaa aaaaaaagca ttacttccaa tgctaccata ctgggctaaa    7860
aatggatgtt tttaatctcg accttaatcc ttctcattta acagcagtgg cctaccaa      7918
```

<210> SEQ ID NO 13
<211> LENGTH: 5777
<212> TYPE: DNA
<213> ORGANISM: Arabidopsis thaliana

<400> SEQUENCE: 13

```
gatcttttc  atgttttgtt  tttattcata  catatccaag  agactttaaa  tatttgttta    60
tcaatattac  aaattatcac  ataatatatt  cgtgttttgc  ttttattcat  atgattccaa  120
aaatcactta  ttaaaagcta  ttcattttaa  acttgttcca  acctaaacat  ctttattttt  180
aaagtctttt  cagaatatta  gaccaaaaat  ataaatacat  tttaataata  tatatgacca  240
aattaattat  ttaaaacttt  tgcagatgca  tcatctatat  atacattttt  gcagccactt  300
tgtgaaataa  atcctggagt  tgggatttat  ttacagcggc  tgccactgga  atttaataat  360
tatttttgat  aattagaaag  aaaatcttct  aattaaatat  ttgacattta  acaatcttcc  420
caaaatctct  ctaccttaac  tacacgatta  attactaaaa  taaaacttcc  aaaatattta  480
atattattta  attactacaa  aattatcatt  tttgatattg  cttttctaca  tgattataat  540
catcaaaccg  tagagatctt  tgatagcatt  taattactac  aaaattacaa  aatatttaga  600
caataattca  taaacatatc  ataaataaga  tcaacattaa  taaaataaat  gagttttttt  660
tagaggacgg  gttggcggga  cgggtttggc  aggacgttac  ttaataacaa  ttgtaaacta  720
taaaataaaa  acattttata  actatataca  atttacaaac  ttttatatat  attaatttaa  780
aaaataaatt  gttcccgcgg  tgtaccgcgg  gttaaaatct  agttatattt  taaaaatcga  840
gatgttacat  atgtgttaaa  ctttcttttt  tgtcttctta  tgtgatatca  aattttatga  900
tcttatcgat  tttaatcagg  tatatcttgg  tatagcctta  gatttcataa  tcgcatataa  960
aaatcataaa  ttatgtagaa  actagttata  atcaaataat  atttatttca  tatggtatac  1020
caaaattaag  tattcaattg  ctacgtggat  attaataatt  tgaattcggt  aacatactct  1080
ttttcttttt  gttaaaccaa  agaatctcaa  acaaaagttt  ttgatcatag  ttactaaatc  1140
atttttggtg  aataaccgag  agaatgtctc  ccgacttcta  ttaaaaaaca  aaaataacaa  1200
ttacacaatc  actcgtcttg  aacaaacagg  tctagaaaca  tcatcccgta  agatttcatc  1260
cgcacaccgg  agaacataaa  caagagcata  aaagcttaaa  gacaagcata  gtttgttaac  1320
atgtccgtaa  aatgattagc  ctctctatat  gtgaaacacg  gtcaatctag  ttttttcgata  1380 aaaaactata  gcgcaaacgt  actagaaatg  atagcagatg  agagtcccat  aactttgtct  1440
tcaaaatctc  aaccaccatt  taccacaaat  atggggatga  aaacaggcaa  acggtctcat  1500
acgtcgtaaa  taagcattct  taatgtcaag  ttggtagata  ggccataaaa  taagcatcct  1560
tatgtttagc  gcatagcctc  cacaccattc  accctcctca  ttacgtatca  gaccaccacc  1620
agccgcgagt  ctcgaattgc  cataaaatac  cccatcagta  tttaatttaa  accagcccat  1680
agacgagata  agccatttta  tcagcttctc  aacccgacca  gcccttttgtg  ttgcctttcc  1740 gctactagct  ctcgcctcca  atacctcctt  agctaactct  cttatgaacc  gcaccctatt  1800
cttccatact  ttattctccc  caaaaactag  ctaattgaat  taccaacatt  tgatcaagat  1860
aatatactag  gtagctaatt  aatgagctca  ttttttttttt  gtcgtcaatg  ggctaattta  1920
ttaattacag  tatgaactat  tgactattat  tctaaataag  tgaatatcac  gagtatgtac  1980
gaattattgg  atgtatctat  ttgtattgat  tgatgtaata  tcaaatagta  agaatttgga  2040
```

-continued

```
gtaaacgtgg gtttggggtt gaagcaggta gggcatgtca aagtagggcg tctttcgtta    2100 tgtcccttc  ctctaaattt gaacctctgt cattgtttac agaaaaatcg taataaccca    2160
taaatgtgtt ttaaaaaaca ttatttcgag ttttctacac atattctagt catgtttaat    2220
ttgaatcttt tcttatttaa gtaagcttta gacatttta  acctaagttt tcttctccct    2280
tcataaattt tgagatctat ataatgttct tacattttgg atcaagatct tcatattctc    2340
attccaatta gtaaaagatt ttttcacctt ttaatctctt atcttttatt tatattcttt    2400
agttatgttt atgcttttca tcatatttag tggttagttt ttattattta tttattgatt    2460
catgacttat gctagattat gataagaatt tatgttacca cttgataaat cctccatttg    2520
acatgtgttt aatgctagat ttatattgtc tccaaattta caactttgat gtcttatgat    2580
aaatgccaac aaccaaattt cagataaaga ttagcagact aactaagctt attattcact    2640
tgcaaggtgg agtgatgttg aaagaaccct cacagacacg tcattgggaa gactaaatct    2700 cttttagca  cgttacacct ttgagatcgc gtttattcca tatggagaga gagcaacaat    2760
acgagacatg gagaggcacc attaccgccg gcgcaactgc ttccaaatat tgacaaacaa    2820
atttgaatct ggatcttctc tattcgtgaa caaggagata gaagctacga tgaatgcatg    2880
gaagcttggt ttgctttaat ataaacacta aggggagta  gaactttctt gaaaaattgt    2940
atgcaaatta tttaccgaat gttaaaagct tttttcgaat aaattttaca ttttcttaat    3000
aataataata aaaaaggatt gttgattatc ttaatcacaa acaatttatt ttagctgaat    3060
tagacaattg ttagtaaaat gattagagtg tcacatatta atgttgttag tgtttcatgt    3120
catcctagtg atccaataat taggccattc tatagctcgt aacgttaaaa taaaaggccc    3180
attatctgaa tatacagaag cccattatca atagatacat taaaagatac tgattaatcc    3240
agagggttta tatctacgcc gtctccattg attatttctc cgtctcttga aaaatccgac    3300
tgacactgac ctcaaaactc tcctctcact ttcgtcgtga agaagccaaa tctcgaatcg    3360
aatcagcacc acacatttcc atggataatt cagctccaga ttcgttatcc agatcggaaa    3420
ccgccgtcac atacgactca ccatatccac tctacgccat ggctttctct tctctccgct    3480
catcctccgg tcacagaatc gccgtcggaa gcttcctcga agattacaac aaccgcatcg    3540
acattctctc tttcgattcc gattcaatga ccgttaagcc tctcccgaat ctctccttcg    3600
agcatcctta tcctccaaca aagctaatgt tcagtcctcc ttctctccgt cgtccttcct    3660
ccggagatct cctcgcttcc tccggcgatt tcctccgtct ttgggaaatt aacgaagatt    3720
catcaaccgt cgagccaatc tcggttctca acaacagcaa aacgagcgag ttttgtgcgc    3780
cgttgacttc cttcgattgg aacgatgtag agccgaaacg tctcggaact tgtagtattg    3840
atacgacgtg tacgatttgg gatattgaga agtctgttgt tgagactcag cttatagctc    3900
atgataaaga ggttcatgac attgcttggg gagaagctag ggttttcgca tcagtctctg    3960
ctgatggatc cgttaggatc tttgatttac gtgataagga acattctaca atcatttacg    4020
agagtcctca gcctgatacg cctttgttaa gacttgcttg gaacaaacaa gatcttagat    4080
atatggctac gattttgatg gattctaata aggttgtgat tctcgatatt cgttcgccga    4140
ctatgcctgt tgctgagctt gaaagacatc aggctagtgt gaatgctata gcttgggcgc    4200
ctcagagctg taaacatatt tgttctggtg gtgatgatac acaggctctt atttgggagc    4260
ttcctactgt tgctggaccc aatgggattg atccgatgtc ggtttattcg gctggttcgg    4320
agattaatca gttgcagtgg tcttcttcgc agcctgattg gattggtatt gcttttgcta    4380
acaaaatgca gctccttaga gtttgaggtg agagtttctc tttcgctaca taattctcat    4440
```

```
ttgctaggcc tagattctaa tgaggaagca ttgattattg gtttagattg tgttgcatta    4500
cagatagttc tctaggtttg gtaactaaac gttttttcga ttcttgataa caaagccact    4560
agagatttga cactaactcg ttttagattt acctgaatca atatctctgt taaaatcaat    4620
tactttgtta tgcatacata atcacagtt tagtagtcat atatattggc tcttattagc     4680
gacaggtctc acacttgctg taatggctga tagtgtagta gtcatatgtt ggctttcatc    4740
taagttgatg tatcatatga tgaatagttg tacactcgtc aggttctaat ttttacccat    4800
aattcttcag tctattttt tttgagacaa tctattctta atttaacgaa gccactagct     4860
acgtatacaa atattgttaa tttaacgaag tatctgagaa ttgtttactg ctgactctgc    4920
tgtatgccct cagaaacata tagaagtgga attggaaact tcatgctggt ttgaacatct    4980
ttgtatgtgt gcttcaggtt tttgtaactc atttagacaa cagcattgca tatatacacg    5040
cacatatgca acctagaaaa tcaaataacc tttccttata attactatcc atttcacttg    5100
atgtcaggtg cagatgtgaa gtgatcaata aggattttag catagacccg tataatcgtc    5160
atgtgcgtaa gtaggtttgg tttgcgctcc ctctcgcttt taggtccgca atgactctgt    5220
atctatctga ttgtaactaa aactgaattc atttgatgaa ccaaatgata ctattatctt    5280
atgttgtgta taaaacccaa ccaggatata ttgcggtttc tggtgtttag atttggtaat    5340
tggagcttag tacaatgcaa ccctgtcttg ctttattgga cgtctctaag ataaatcagc    5400
ttgcaatgaa ttccaatgga gtttgtcagt ttgaattaac ttctttgcat aattaacaca    5460
aagatttgca gtataaattc cattggaaga cttatttgtt tatttgacac agatttaaat    5520
tgaatttcaa tggagtttca gtcgactatg tgacacaaag atttgaaatg aactccaatg    5580
ggaatttgat gagtaaatta ttataaacaa tccaatgttt gacacaaata ttttagaatc    5640
ttcacatctg aagtcttata aatcgtagca aaattttcaa tcttgaaaat tataaaaaat    5700
gagaattaat ttaaatcact gatccgataa tctcctctag aaatataaga atctataaac    5760
cattaatagt agaattc                                                    5777
```

<210> SEQ ID NO 14
<211> LENGTH: 341
<212> TYPE: PRT
<213> ORGANISM: Arabidopsis thaliana

<400> SEQUENCE: 14

```
Met Asp Asn Ser Ala Pro Asp Ser Leu Ser Arg Ser Glu Thr Ala Val
1               5                   10                  15

Thr Tyr Asp Ser Pro Tyr Pro Leu Tyr Ala Met Ala Phe Ser Ser Leu
            20                  25                  30

Arg Ser Ser Gly His Arg Ile Ala Val Gly Ser Phe Leu Glu Asp
        35                  40                  45

Tyr Asn Asn Arg Ile Asp Ile Leu Ser Phe Asp Ser Asp Ser Met Thr
    50                  55                  60

Val Lys Pro Leu Pro Asn Leu Ser Phe Glu His Pro Tyr Pro Pro Thr
65                  70                  75                  80

Lys Leu Met Phe Ser Pro Pro Ser Leu Arg Arg Pro Ser Ser Gly Asp
                85                  90                  95

Leu Leu Ala Ser Ser Gly Asp Phe Leu Arg Leu Trp Glu Ile Asn Glu
            100                 105                 110

Asp Ser Ser Thr Val Glu Pro Ile Ser Val Leu Asn Asn Ser Lys Thr
        115                 120                 125

Ser Glu Phe Cys Ala Pro Leu Thr Ser Phe Asp Trp Asn Asp Val Glu
```

```
                130               135                140
Pro Lys Arg Leu Gly Thr Cys Ser Ile Asp Thr Thr Cys Thr Ile Trp
145                 150                 155                 160

Asp Ile Glu Lys Ser Val Val Glu Thr Gln Leu Ile Ala His Asp Lys
                165                 170                 175

Glu Val His Asp Ile Ala Trp Gly Glu Ala Arg Val Phe Ala Ser Val
            180                 185                 190

Ser Ala Asp Gly Ser Val Arg Ile Phe Asp Leu Arg Asp Lys Glu His
            195                 200                 205

Ser Thr Ile Ile Tyr Glu Ser Pro Gln Pro Asp Thr Pro Leu Leu Arg
        210                 215                 220

Leu Ala Trp Asn Lys Gln Asp Leu Arg Tyr Met Ala Thr Ile Leu Met
225                 230                 235                 240

Asp Ser Asn Lys Val Val Ile Leu Asp Ile Arg Ser Pro Thr Met Pro
                245                 250                 255

Val Ala Glu Leu Glu Arg His Gln Ala Ser Val Asn Ala Ile Ala Trp
            260                 265                 270

Ala Pro Gln Ser Cys Lys His Ile Cys Ser Gly Gly Asp Asp Thr Gln
            275                 280                 285

Ala Leu Ile Trp Glu Leu Pro Thr Val Ala Gly Pro Asn Gly Ile Asp
        290                 295                 300

Pro Met Ser Val Tyr Ser Ala Gly Ser Glu Ile Asn Gln Leu Gln Trp
305                 310                 315                 320

Ser Ser Ser Gln Pro Asp Trp Ile Gly Ile Ala Phe Ala Asn Lys Met
                325                 330                 335

Gln Leu Leu Arg Val
            340

<210> SEQ ID NO 15
<211> LENGTH: 1639
<212> TYPE: DNA
<213> ORGANISM: Arabidopsis thaliana

<400> SEQUENCE: 15
agggaaaaaa aaaacagagg aactaataaa cggaccatga gctccacaga gacatacgag      60
ccgttattga cacgactcca ctcggattct cagataactg aacggtcttc gccagagata     120
gaggagtttc tccgccgtcg tggatccaca gtgacaccac ggtggtggct aaagctggca     180
gtgtgggagt caaagcttct atggacactc tctggagcct ctatagtggt ctctgttctg     240
aattacatgc tcagcttcgt caccgtcatg ttcaccggtc atctcggttc tcttcagctc     300
gccggcgctt ccatcgccac cgtcggaatc caaggcctag cttacggtat catgttagga     360
atggcgagcg cggtccaaac agtgtgtggt caagcgtacg gagcgagaca gtactcatca     420
atgggaataa tctgccaacg agccatggtc ttgcaccttg cagctgcagt cttcctcacg     480
ttcctctact ggtactcggg tccaatcctt aaaacaatgg ccaatccgt agccatagca      540 cacgagggtc agatctttgc acgtggaatg attccacaaa tttacgcatt tgccctcgct     600
tgcccgatgc agaggtttct tcaggctcag aacatagtga acccttttggc ttacatgtcc    660 ttaggagttt tcttgctcca cacgttactc acgtggctgg ttaccaacgt gctggatttc     720
ggcttgcttg gggcggctct gattctcagt ttctcatggt ggctgctagt agctgtgaat     780
ggtatgtata tcttgatgag cccgaattgt aaggagacat ggacagggtt tcaacgagg     840 gcatttagag ggatatggcc ttacttcaag ctcacggtag cttcagcagt tatgctatgt     900
ttggagatat ggtacaacca aggctagtg attatctctg gtttactctc caatccgaca     960
```

-continued

```
atttctctag acgctatttc gatttgcatg tattacttga attgggatat gcagttcatg   1020
cttggtctaa gtgcagcaat cagtgtgcga gtgagcaatg agctaggagc gggaaatcca   1080
cgagtggcta tgttatcagt agtggttgtc aacatcacga ctgttctcat cagctcagtt   1140
ctctgtgtca tcgtgcttgt gttccgcgtt ggccttagca aagccttcac cagcgatgca   1200
gaagttatag cagccgtctc tgacctcttt cctcttctcg ccgtttccat tttcttaaac   1260
ggaatccagc caattctctc tggggttgct attgggagtg ggtggcaagc agtggtggct   1320
tatgtgaatc ttgttacgta ctatgtcatt ggtcttccta ttggctgtgt ccttggcttc   1380
aaaaccagtc ttggagttgc tgggatctgg tgggggatga ttgcaggagt catacttcaa   1440
accctaactt tgattgttct tacacttaaa actaattgga cttccgaggt agaaaatgca   1500
gctcagagag taaagacttc ggcaactgag aatcaagaga tggctaacgc aggtgtttaa   1560
gataacagca acagtgactc tgttttttttt cccctctttt ggtgaaaaga gatataagat   1620
gaaaaaaaaa aaaaaaaaa                                                1639
```

<210> SEQ ID NO 16
<211> LENGTH: 507
<212> TYPE: PRT
<213> ORGANISM: Arabidopsis thaliana

<400> SEQUENCE: 16

```
Met Ser Ser Thr Glu Thr Tyr Glu Pro Leu Leu Thr Arg Leu His Ser
1               5                   10                  15

Asp Ser Gln Ile Thr Glu Arg Ser Ser Pro Glu Ile Glu Glu Phe Leu
            20                  25                  30

Arg Arg Arg Gly Ser Thr Val Thr Pro Arg Trp Trp Leu Lys Leu Ala
        35                  40                  45

Val Trp Glu Ser Lys Leu Leu Trp Thr Leu Ser Gly Ala Ser Ile Val
    50                  55                  60

Val Ser Val Leu Asn Tyr Met Leu Ser Phe Val Thr Val Met Phe Thr
65                  70                  75                  80

Gly His Leu Gly Ser Leu Gln Leu Ala Gly Ala Ser Ile Ala Thr Val
                85                  90                  95

Gly Ile Gln Gly Leu Ala Tyr Gly Ile Met Leu Gly Met Ala Ser Ala
            100                 105                 110

Val Gln Thr Val Cys Gly Gln Ala Tyr Gly Ala Arg Gln Tyr Ser Ser
        115                 120                 125

Met Gly Ile Ile Cys Gln Arg Ala Met Val Leu Leu Ala Ala Ala
    130                 135                 140

Val Phe Leu Thr Phe Leu Tyr Trp Tyr Ser Gly Pro Ile Leu Lys Thr
145                 150                 155                 160

Met Gly Gln Ser Val Ala Ile Ala His Glu Gly Gln Ile Phe Ala Arg
                165                 170                 175

Gly Met Ile Pro Gln Ile Tyr Ala Phe Ala Leu Ala Cys Pro Met Gln
            180                 185                 190

Arg Phe Leu Gln Ala Gln Asn Ile Val Asn Pro Leu Ala Tyr Met Ser
        195                 200                 205

Leu Gly Val Phe Leu Leu His Thr Leu Leu Thr Trp Leu Val Thr Asn
    210                 215                 220

Val Leu Asp Phe Gly Leu Leu Gly Ala Ala Leu Ile Leu Ser Phe Ser
225                 230                 235                 240

Trp Trp Leu Leu Val Ala Val Asn Gly Met Tyr Ile Leu Met Ser Pro
                245                 250                 255
```

Asn Cys Lys Glu Thr Trp Thr Gly Phe Ser Thr Arg Ala Phe Arg Gly
                260                 265                 270

Ile Trp Pro Tyr Phe Lys Leu Thr Val Ala Ser Ala Val Met Leu Cys
            275                 280                 285

Leu Glu Ile Trp Tyr Asn Gln Gly Leu Val Ile Ser Gly Leu Leu
290                 295                 300

Ser Asn Pro Thr Ile Ser Leu Asp Ala Ile Ser Ile Cys Met Tyr Tyr
305                 310                 315                 320

Leu Asn Trp Asp Met Gln Phe Met Leu Gly Leu Ser Ala Ala Ile Ser
                325                 330                 335

Val Arg Val Ser Asn Glu Leu Gly Ala Gly Asn Pro Arg Val Ala Met
            340                 345                 350

Leu Ser Val Val Val Asn Ile Thr Thr Val Leu Ile Ser Ser Val
355                 360                 365

Leu Cys Val Ile Val Leu Val Phe Arg Val Gly Leu Ser Lys Ala Phe
370                 375                 380

Thr Ser Asp Ala Glu Val Ile Ala Ala Val Ser Asp Leu Phe Pro Leu
385                 390                 395                 400

Leu Ala Val Ser Ile Phe Leu Asn Gly Ile Gln Pro Ile Leu Ser Gly
                405                 410                 415

Val Ala Ile Gly Ser Gly Trp Gln Ala Val Val Ala Tyr Val Asn Leu
            420                 425                 430

Val Thr Tyr Tyr Val Ile Gly Leu Pro Ile Gly Cys Val Leu Gly Phe
435                 440                 445

Lys Thr Ser Leu Gly Val Ala Gly Ile Trp Trp Gly Met Ile Ala Gly
450                 455                 460

Val Ile Leu Gln Thr Leu Thr Leu Ile Val Leu Thr Leu Lys Thr Asn
465                 470                 475                 480

Trp Thr Ser Glu Val Glu Asn Ala Ala Gln Arg Val Lys Thr Ser Ala
                485                 490                 495

Thr Glu Asn Gln Glu Met Ala Asn Ala Gly Val
            500                 505

<210> SEQ ID NO 17
<211> LENGTH: 258
<212> TYPE: PRT
<213> ORGANISM: Arabidopsis thaliana

<400> SEQUENCE: 17

Met Gly Lys Arg Ala Thr Thr Ser Val Arg Arg Glu Glu Leu Asn Arg
1               5                   10                  15

Gly Ala Trp Thr Asp His Glu Asp Lys Ile Leu Arg Asp Tyr Ile Thr
                20                  25                  30

Thr His Gly Glu Gly Lys Trp Ser Thr Leu Pro Asn Gln Ala Gly Leu
            35                  40                  45

Lys Arg Cys Gly Lys Ser Cys Arg Leu Arg Trp Lys Asn Tyr Leu Arg
        50                  55                  60

Pro Gly Ile Lys Arg Gly Asn Ile Ser Ser Asp Glu Glu Leu Ile
65                  70                  75                  80

Ile Arg Leu His Asn Leu Leu Gly Asn Arg Trp Ser Leu Ile Ala Gly
                85                  90                  95

Arg Leu Pro Gly Arg Thr Asp Asn Glu Ile Lys Asn His Trp Asn Ser
            100                 105                 110

Asn Leu Arg Lys Arg Leu Pro Lys Thr Gln Thr Lys Gln Pro Lys Arg
        115                 120                 125

```
Ile Lys His Ser Thr Asn Asn Glu Asn Asn Val Cys Val Ile Arg Thr
        130                 135                 140
Lys Ala Ile Arg Cys Ser Lys Thr Leu Leu Phe Ser Asp Leu Ser Leu
145                 150                 155                 160
Gln Lys Lys Ser Ser Thr Ser Pro Leu Pro Leu Lys Glu Gln Glu Met
                165                 170                 175
Asp Gln Gly Gly Ser Ser Leu Met Gly Asp Leu Glu Phe Asp Phe Asp
            180                 185                 190
Arg Ile His Ser Glu Phe His Phe Pro Asp Leu Met Asp Phe Asp Gly
                195                 200                 205
Leu Asp Cys Gly Asn Val Thr Ser Leu Val Ser Ser Asn Glu Ile Leu
        210                 215                 220
Gly Glu Leu Val Pro Ala Gln Gly Asn Leu Asp Leu Asn Arg Pro Phe
225                 230                 235                 240
Thr Ser Cys His His Arg Gly Asp Asp Glu Asp Trp Leu Arg Asp Phe
                245                 250                 255
Thr Cys

<210> SEQ ID NO 18
<211> LENGTH: 303
<212> TYPE: PRT
<213> ORGANISM: Arabidopsis thaliana

<400> SEQUENCE: 18

Met Glu Ser Pro Pro Leu Tyr Glu Ile Ser Ser Ser Ser Ser Ser Glu
1               5                   10                  15
Lys Pro Arg His His Phe Gln Ser Leu Asp Leu Phe Pro Asn Leu Asn
                20                  25                  30
Gln Asn Ser Cys Ile Asn Asn Thr Leu Ile Glu Pro Leu Pro Leu Ile
            35                  40                  45
Asp Arg Ile Asn Leu Asn Ser Asn Leu Asp Leu Asn Pro Asn Pro Leu
        50                  55                  60
Tyr Ala Glu Glu Gly Glu Gln Glu Glu Glu Glu Glu Glu Glu Glu Asp
65                  70                  75                  80
Arg Glu Val Asp Val Asp Leu His Ile Gly Leu Pro Gly Phe Gly Lys
                85                  90                  95
Pro Ser Asn Asp Ala Lys Gln Leu Lys Lys Arg Asn Gly Lys Glu Ile
                100                 105                 110
Ala Thr Tyr Asp Ala Gly Lys Gly Ile Glu Asn Glu Leu Ser Gly Lys
            115                 120                 125
Ala Tyr Trp Ile Pro Ala Pro Glu Gln Ile Leu Ile Gly Phe Thr His
        130                 135                 140
Phe Ser Cys His Val Cys Phe Lys Thr Phe Asn Arg Tyr Asn Asn Leu
145                 150                 155                 160
Gln Met His Met Trp Gly His Gly Ser Gln Tyr Arg Lys Gly Pro Glu
                165                 170                 175
Ser Leu Lys Gly Thr Gln Pro Arg Ala Met Leu Gly Ile Pro Cys Tyr
            180                 185                 190
Cys Cys Val Glu Gly Cys Arg Asn His Ile Asp His Pro Arg Ser Lys
                195                 200                 205
Pro Leu Lys Asp Phe Arg Thr Leu Gln Thr His Tyr Lys Arg Lys His
        210                 215                 220
Gly His Lys Pro Phe Ser Cys Arg Leu Cys Gly Lys Leu Leu Ala Val
225                 230                 235                 240
```

```
Lys Gly Asp Trp Arg Thr His Glu Lys Asn Cys Gly Lys Arg Trp Val
                245                 250                 255

Cys Val Cys Gly Ser Asp Phe Lys His Lys Arg Ser Leu Lys Asp His
            260                 265                 270

Val Lys Ala Phe Gly Ser Gly His Gly Pro Tyr Pro Thr Gly Leu Phe
        275                 280                 285

Glu Glu Gln Ala Ser Asn Ser Ser Val Ser Glu Thr Leu Phe Phe
    290                 295                 300
```

<210> SEQ ID NO 19
<211> LENGTH: 518
<212> TYPE: PRT
<213> ORGANISM: Arabidopsis thaliana

<400> SEQUENCE: 19

```
Met Asp Glu Ser Ser Ile Ile Pro Ala Glu Lys Val Ala Gly Ala Glu
1               5                   10                  15

Lys Lys Glu Leu Gln Gly Leu Leu Lys Thr Ala Val Gln Ser Val Asp
            20                  25                  30

Trp Thr Tyr Ser Val Phe Trp Gln Phe Cys Pro Gln Gln Arg Val Leu
        35                  40                  45

Val Trp Gly Asn Gly Tyr Tyr Asn Gly Ala Ile Lys Thr Arg Lys Thr
    50                  55                  60

Thr Gln Pro Ala Glu Val Thr Ala Glu Glu Ala Leu Glu Arg Ser
65                  70                  75                  80

Gln Gln Leu Arg Glu Leu Tyr Glu Thr Leu Leu Ala Gly Glu Ser Thr
                85                  90                  95

Ser Glu Ala Arg Ala Cys Thr Ala Leu Ser Pro Glu Asp Leu Thr Glu
            100                 105                 110

Thr Glu Trp Phe Tyr Leu Met Cys Val Ser Phe Ser Phe Pro Pro Pro
        115                 120                 125

Ser Gly Met Pro Gly Lys Ala Tyr Ala Arg Arg Lys His Val Trp Leu
    130                 135                 140

Ser Gly Ala Asn Glu Val Asp Ser Lys Thr Phe Ser Arg Ala Ile Leu
145                 150                 155                 160

Ala Lys Ser Ala Lys Ile Gln Thr Val Val Cys Ile Pro Met Leu Asp
                165                 170                 175

Gly Val Val Glu Leu Gly Thr Thr Lys Lys Val Arg Glu Asp Val Glu
            180                 185                 190

Phe Val Glu Leu Thr Lys Ser Phe Phe Tyr Asp His Cys Lys Thr Asn
        195                 200                 205

Pro Lys Pro Ala Leu Ser Glu His Ser Thr Tyr Glu Val His Glu Glu
    210                 215                 220

Ala Glu Asp Glu Glu Val Glu Glu Met Thr Met Ser Glu Glu
225                 230                 235                 240

Met Arg Leu Gly Ser Pro Asp Asp Glu Val Ser Asn Gln Asn Leu
                245                 250                 255

His Ser Asp Leu His Ile Glu Ser Thr His Thr Leu Asp Thr His Met
            260                 265                 270

Asp Met Met Asn Leu Met Glu Glu Gly Gly Asn Tyr Ser Gln Thr Val
        275                 280                 285

Thr Thr Leu Leu Met Ser His Pro Thr Ser Leu Leu Ser Asp Ser Val
    290                 295                 300

Ser Thr Tyr Ser Tyr Ile Gln Ser Ser Phe Ala Thr Trp Arg Val Glu
305                 310                 315                 320
```

```
Asn Gly Lys Glu His Gln Gln Val Lys Thr Ala Pro Ser Ser Gln Trp
            325                 330                 335

Val Leu Lys Gln Met Ile Phe Arg Val Pro Phe Leu His Asp Asn Thr
        340                 345                 350

Lys Asp Lys Arg Leu Pro Arg Glu Asp Leu Ser His Val Val Ala Glu
        355                 360                 365

Arg Arg Arg Arg Glu Lys Leu Asn Glu Lys Phe Ile Thr Leu Arg Ser
370                 375                 380

Met Val Pro Phe Val Thr Lys Met Asp Lys Val Ser Ile Leu Gly Asp
385                 390                 395                 400

Thr Ile Ala Tyr Val Asn His Leu Arg Lys Arg Val His Glu Leu Glu
                405                 410                 415

Asn Thr His His Glu Gln Gln His Lys Arg Thr Arg Thr Cys Lys Arg
            420                 425                 430

Lys Thr Ser Glu Glu Val Glu Val Ser Ile Ile Glu Asn Asp Val Leu
        435                 440                 445

Leu Glu Met Arg Cys Glu Tyr Arg Asp Gly Leu Leu Leu Asp Ile Leu
    450                 455                 460

Gln Val Leu His Glu Leu Gly Ile Glu Thr Thr Ala Val His Thr Ser
465                 470                 475                 480

Val Asn Asp His Asp Phe Glu Ala Glu Ile Arg Ala Lys Val Arg Gly
                485                 490                 495

Lys Lys Ala Ser Ile Ala Glu Val Lys Arg Ala Ile His Gln Val Ile
            500                 505                 510

Ile His Asp Thr Asn Leu
        515

<210> SEQ ID NO 20
<211> LENGTH: 1213
<212> TYPE: DNA
<213> ORGANISM: Arabidopsis thaliana

<400> SEQUENCE: 20
caataacaac taaatctcta tctctgtaat ttcaaaagta caatcatgga ccagactctt      60
acacacaccg gatcgaagaa ggcttgtgtc attggtggca cgggaaactt agcctctatt     120
ctcatcaagc atttgcttca aagtggctac aaagttaaca ctacagttag agatccagaa     180
aacgagaaga aaatagctca ccttaggcaa cttcaagaac ttggcgacct gaagatcttc     240
aaggcagatt tgactgatga agacagtttc gaatcctcat tctccggctg tgaatacatc     300
ttccatgtcg caactccgat caactttaaa tccgaagatc ccgagaaaga catgatcaag     360
ccggcgatac aaggagtgat caatgtgttg aaatcttgct taaaatcgaa atcagtcaag     420
cgtgtgatct acacatcttc agctgctgct gtttccatca caatctttc tggaaccgga     480 ctcgtgatga acgaagaaaa ctggactgac attgattttc tcacagagga gaagcctttt     540
aactggggtt acccaatctc gaaggtgcta gcagaaaaga agcttggga atttgcagaa     600 gagaataaga tcaatctcgt aaccgtgatt ccggcactta tagccggaaa ctctctcctc     660
tccgatcctc cgagcagttt atctctctcg atgtctttca tcaccgggaa agaaatgcat     720
gtgacgggtc tcaaggaaat gcagaagcta tctggctcga tctcgttcgt gcacgtagac     780
gatttagctc gtgcccattt gtttcttgcg agaaagaaa ctgcttctgg tcgctacatt     840
tgctgtgctt acaacacaag tgttccagag attgcggatt ttctcataca gagatatcct     900
aagtacaatg tgttgtccga attcgaagag ggcttgtcga ttccgaaatt aacactatct     960
tcgcaaaaac ttatcaatga aggctttcga ttcgaatatg ggatcaatga gatgtatgat    1020
```

```
cagatgatag agtacttcga gtcaaaagga ttgatcaaag ctaaagaatc ttgattttt    1080 ataatgtcaa aatggattct aatagtatat gagtctttgg tctcattctc gttctataaa   1140
atggtattgt ataatattta ttatatattg gttgagttaa tgtctttga tacataaata    1200 ttacatactc tcc                                                      1213
```

<210> SEQ ID NO 21
<211> LENGTH: 342
<212> TYPE: PRT
<213> ORGANISM: Arabidopsis thaliana

<400> SEQUENCE: 21

```
Met Asp Gln Thr Leu Thr His Thr Gly Ser Lys Lys Ala Cys Val Ile
1               5                   10                  15

Gly Gly Thr Gly Asn Leu Ala Ser Ile Leu Ile Lys His Leu Leu Gln
            20                  25                  30

Ser Gly Tyr Lys Val Asn Thr Thr Val Arg Asp Pro Glu Asn Glu Lys
        35                  40                  45

Lys Ile Ala His Leu Arg Gln Leu Gln Glu Leu Gly Asp Leu Lys Ile
    50                  55                  60

Phe Lys Ala Asp Leu Thr Asp Glu Asp Ser Phe Glu Ser Ser Phe Ser
65                  70                  75                  80

Gly Cys Glu Tyr Ile Phe His Val Ala Thr Pro Ile Asn Phe Lys Ser
                85                  90                  95

Glu Asp Pro Glu Lys Asp Met Ile Lys Pro Ala Ile Gln Gly Val Ile
            100                 105                 110

Asn Val Leu Lys Ser Cys Leu Lys Ser Lys Ser Val Lys Arg Val Ile
        115                 120                 125

Tyr Thr Ser Ser Ala Ala Ala Val Ser Ile Asn Asn Leu Ser Gly Thr
    130                 135                 140

Gly Leu Val Met Asn Glu Glu Asn Trp Thr Asp Ile Asp Phe Leu Thr
145                 150                 155                 160

Glu Glu Lys Pro Phe Asn Trp Gly Tyr Pro Ile Ser Lys Val Leu Ala
                165                 170                 175

Glu Lys Lys Ala Trp Glu Phe Ala Glu Glu Asn Lys Ile Asn Leu Val
            180                 185                 190

Thr Val Ile Pro Ala Leu Ile Ala Gly Asn Ser Leu Leu Ser Asp Pro
        195                 200                 205

Pro Ser Ser Leu Ser Leu Ser Met Ser Phe Ile Thr Gly Lys Glu Met
    210                 215                 220

His Val Thr Gly Leu Lys Glu Met Gln Lys Leu Ser Gly Ser Ile Ser
225                 230                 235                 240

Phe Val His Val Asp Asp Leu Ala Arg Ala His Leu Phe Leu Ala Glu
                245                 250                 255

Lys Glu Thr Ala Ser Gly Arg Tyr Ile Cys Cys Ala Tyr Asn Thr Ser
            260                 265                 270

Val Pro Glu Ile Ala Asp Phe Leu Ile Gln Arg Tyr Pro Lys Tyr Asn
        275                 280                 285

Val Leu Ser Glu Phe Glu Gly Leu Ser Ile Pro Lys Leu Thr Leu
    290                 295                 300

Ser Ser Gln Lys Leu Ile Asn Glu Gly Phe Arg Phe Glu Tyr Gly Ile
305                 310                 315                 320

Asn Glu Met Tyr Asp Gln Met Ile Glu Tyr Phe Glu Ser Lys Gly Leu
                325                 330                 335
```

```
Ile Lys Ala Lys Glu Ser
            340

<210> SEQ ID NO 22
<211> LENGTH: 338
<212> TYPE: PRT
<213> ORGANISM: Medicago truncatula

<400> SEQUENCE: 22

Met Ala Ser Ile Lys Gln Ile Glu Ile Glu Lys Lys Ala Cys Val
 1               5                  10                  15

Ile Gly Gly Thr Gly Phe Val Ala Ser Leu Leu Ile Lys Gln Leu Leu
                20                  25                  30

Glu Lys Gly Tyr Ala Val Asn Thr Thr Val Arg Asp Leu Asp Ser Ala
            35                  40                  45

Asn Lys Thr Ser His Leu Ile Ala Leu Gln Ser Leu Gly Glu Leu Asn
    50                  55                  60

Leu Phe Lys Ala Glu Leu Thr Ile Glu Gly Asp Phe Asp Ala Pro Ile
65                  70                  75                  80

Ser Gly Cys Glu Leu Val Phe Gln Leu Ala Thr Pro Val Asn Phe Ala
                85                  90                  95

Ser Gln Asp Pro Glu Asn Asp Met Ile Lys Pro Ala Ile Lys Gly Val
            100                 105                 110

Leu Asn Val Leu Lys Ala Cys Val Arg Ala Lys Glu Val Lys Arg Val
        115                 120                 125

Ile Leu Thr Ser Ser Ala Ala Ala Val Thr Ile Asn Glu Leu Glu Gly
    130                 135                 140

Thr Gly His Val Met Asp Glu Thr Asn Trp Ser Asp Val Glu Phe Leu
145                 150                 155                 160

Asn Thr Ala Lys Pro Pro Thr Trp Gly Tyr Pro Val Ser Lys Val Leu
                165                 170                 175

Ala Glu Lys Ala Ala Trp Lys Phe Ala Glu Glu Asn Asn Ile Asp Leu
            180                 185                 190

Ile Thr Val Ile Pro Thr Leu Thr Ile Gly Pro Ser Leu Thr Gln Asp
        195                 200                 205

Ile Pro Ser Ser Val Ala Met Gly Met Ser Leu Leu Thr Gly Asn Asp
    210                 215                 220

Phe Leu Ile Asn Ala Leu Lys Gly Met Gln Phe Leu Ser Gly Ser Ile
225                 230                 235                 240

Ser Ile Thr His Val Glu Asp Ile Cys Arg Ala His Ile Phe Val Ala
                245                 250                 255

Glu Lys Glu Ser Thr Ser Gly Arg Tyr Ile Cys Cys Ala His Asn Thr
            260                 265                 270

Ser Val Pro Glu Leu Ala Lys Phe Leu Ser Lys Arg Tyr Pro Gln Tyr
        275                 280                 285

Lys Val Pro Thr Glu Phe Asp Asp Phe Pro Ser Lys Ala Lys Leu Ile
    290                 295                 300

Ile Ser Ser Gly Lys Leu Ile Lys Glu Gly Phe Ser Phe Lys His Ser
305                 310                 315                 320

Ile Ala Glu Thr Phe Asp Gln Thr Val Glu Tyr Leu Lys Thr Gln Gly
                325                 330                 335

Ile Lys

<210> SEQ ID NO 23
<211> LENGTH: 777
<212> TYPE: DNA
```

<213> ORGANISM: Arabidopsis thaliana

<400> SEQUENCE: 23

```
atgggaaaga gagcaactac tagtgtgagg agagaagagt taaacagagg agcttggact      60
gatcatgaag acaagatcct tagagattac atcaccactc acggcgaagg caaatggagc     120
actctcccta accaagctgg tctcaagagg tgtggcaaaa gctgtagact cggtggaag      180
aactacctaa gaccggggat aaagcgcggt aacatctcat ctgatgaaga agaactcata     240
atccgtctcc ataatcttct tggaaacaga tggtcgttga tagctgggag gcttccaggc     300
cgaacagaca atgaaataaa gaatcattgg aactcaaacc tccgcaaaag acttcccaaa     360
actcaaacca agcaaccaaa acgtataaaa cattcgacga caacgagaa taatgtatgt      420
gttatacgta caaaggcgat taggtgctca aagactcttc tcttctcgga tctctctctt     480
cagaagaaga gtagtactag tccactacct ctgaaagaac aagagatgga tcaaggtgga     540
tcttcgttga tgggagatct cgaattcgat ttcgatagga tccattcgga gtttcacttc     600
ccggatttga tggattttga tggtttggac tgtggaaacg ttacatctct tgtttcatct     660
aacgagattt tgggagagtt ggttcctgct caaggtaatc tcgatctcaa tagaccttc      720
acttcttgtc atcatcgtgg cgacgatgaa gattggctcc gagacttcac ttgttga         777
```

<210> SEQ ID NO 24
<211> LENGTH: 1102
<212> TYPE: DNA
<213> ORGANISM: Arabidopsis thaliana

<400> SEQUENCE: 24

```
aaaacatttc atctctctcc aacaactatt caccacattc aatggagtca ccaccactat      60
acgagatatc ctcaagctct tcttctgaaa aacctagaca ccatttccaa tcccttgatc     120
tcttccctaa cctcaaccaa aactcttgta tcaacaatac cctaattgag cctttaccgc     180
ttattgatcg cataaacttg aactcaaacc tagacctaaa ccctaatccc ttgtatgcgg     240
aagaaggaga gcaagaggag gaagaagaag aagaagaaga ccgtgaagtg gacgtggact     300
tacacatcgg ccttcctggt tttggtaaac caagcaatga tgctaaacag ctgaagaaga     360
gaaatgggaa ggagatcgcc acatatgacg ccggaaaagg catcgagaat gaactttccg     420
gaaaggcata ctggatcccg gcgccggagc aaattctcat agggttcact cattttttctt     480
gccatgtatg cttcaagaca ttcaatcgct acaacaatct tcagatgcac atgtggggac     540
atggttcaca atacaggaaa ggaccggagt cactgaaagg cacacagcca cgagccatgt     600
tagggatccc ttgttactgc tgcgttgaag ggtgcaggaa ccacattgac catcctcgtt     660
ccaagccact gaaagacttt aggacgctcc aaacgcacta caaacgcaaa cacgacaca      720
aaccettctc gtgtcgcctt tgcggtaagc ttttggctgt caagggcgat tggcgaacac     780
atgagaagaa ttgtgaaaaa cgttgggttt gcgtttgcgg ttctgatttt aaacacaaac     840
gttctcttaa ggaccatgtt aaggcgtttg ggtctggtca tgggccttat ccaactggtt     900
tgtttgaaga gcaggcttct aattcatctg tctccgagac tttgtttttt taaatttggg     960
catcttttc tttcgcttat gaaatatcta tttactttag aaaaataata atgtggtatc    1020
taattgttcc aaattaggaa cacgaagtgt accattatat ttttcatcac tacaaatgtt    1080
attcagagaa aattatcatt aa                                              1102
```

<210> SEQ ID NO 25
<211> LENGTH: 29
<212> TYPE: DNA

-continued

```
<213> ORGANISM: Artificial sequence
<220> FEATURE:
<223> OTHER INFORMATION: Synthetic primer

<400> SEQUENCE: 25
caccatgaac ttggcctcaa atttcatgg                                          29

<210> SEQ ID NO 26
<211> LENGTH: 25
<212> TYPE: DNA
<213> ORGANISM: Artificial sequence
<220> FEATURE:
<223> OTHER INFORMATION: Synthetic primer

<400> SEQUENCE: 26
ttaaatctgg tttttctgca ccaaa                                              25

<210> SEQ ID NO 27
<211> LENGTH: 33
<212> TYPE: DNA
<213> ORGANISM: Artificial sequence
<220> FEATURE:
<223> OTHER INFORMATION: Synthetic primer

<400> SEQUENCE: 27
cgggatccat gaacttggcc tcaaatttca tgg                                     33

<210> SEQ ID NO 28
<211> LENGTH: 31
<212> TYPE: DNA
<213> ORGANISM: Artificial sequence
<220> FEATURE:
<223> OTHER INFORMATION: Synthetic primer

<400> SEQUENCE: 28
tgaactgcag ttaaatctgg tttttctgca c                                       31

<210> SEQ ID NO 29
<211> LENGTH: 470
<212> TYPE: PRT
<213> ORGANISM: Rauvolfia serpentina

<400> SEQUENCE: 29

Met Glu His Thr Pro His Ile Ala Met Val Pro Thr Pro Gly Met Gly
  1               5                  10                  15

His Leu Ile Pro Leu Val Glu Phe Ala Lys Arg Leu Val Leu Arg His
                 20                  25                  30

Asn Phe Gly Val Thr Phe Ile Ile Pro Thr Asp Gly Pro Leu Pro Lys
             35                  40                  45

Ala Gln Lys Ser Phe Leu Asp Ala Leu Pro Ala Gly Val Asn Tyr Val
         50                  55                  60

Leu Leu Pro Pro Val Ser Phe Asp Asp Leu Pro Ala Asp Val Arg Ile
 65                  70                  75                  80

Glu Thr Arg Ile Cys Leu Thr Ile Thr Arg Ser Leu Pro Phe Val Arg
                 85                  90                  95

Asp Ala Val Lys Thr Leu Leu Ala Thr Thr Lys Leu Ala Ala Leu Val
                100                 105                 110

Val Asp Leu Phe Gly Thr Asp Ala Phe Asp Val Ala Ile Glu Phe Lys
            115                 120                 125

Val Ser Pro Tyr Ile Phe Tyr Pro Thr Thr Ala Met Cys Leu Ser Leu
        130                 135                 140

Phe Phe His Leu Pro Lys Leu Asp Gln Met Val Ser Cys Glu Tyr Arg
```

```
            145                 150                 155                 160
Asp Val Pro Glu Pro Leu Gln Ile Pro Gly Cys Ile Pro Ile His Gly
                165                 170                 175

Lys Asp Phe Leu Asp Pro Ala Gln Asp Arg Lys Asn Asp Ala Tyr Lys
            180                 185                 190

Cys Leu Leu His Gln Ala Lys Arg Tyr Arg Leu Ala Glu Gly Ile Met
        195                 200                 205

Val Asn Thr Phe Asn Asp Leu Glu Pro Gly Pro Leu Lys Ala Leu Gln
    210                 215                 220

Glu Glu Asp Gln Gly Lys Pro Pro Val Tyr Pro Ile Gly Pro Leu Ile
225                 230                 235                 240

Arg Ala Asp Ser Ser Lys Val Asp Asp Cys Glu Cys Leu Lys Trp
                245                 250                 255

Leu Asp Asp Gln Pro Arg Gly Ser Val Leu Phe Ile Ser Phe Gly Ser
            260                 265                 270

Gly Gly Ala Val Ser His Asn Gln Phe Ile Glu Leu Ala Leu Gly Leu
        275                 280                 285

Glu Met Ser Glu Gln Arg Phe Leu Trp Val Val Arg Ser Pro Asn Asp
290                 295                 300

Lys Ile Ala Asn Ala Thr Tyr Phe Ser Ile Gln Asn Gln Asn Asp Ala
305                 310                 315                 320

Leu Ala Tyr Leu Pro Glu Gly Phe Leu Glu Arg Thr Lys Gly Arg Cys
                325                 330                 335

Leu Leu Val Pro Ser Trp Ala Pro Gln Thr Glu Ile Leu Ser His Gly
            340                 345                 350

Ser Thr Gly Gly Phe Leu Thr His Cys Gly Trp Asn Ser Ile Leu Glu
        355                 360                 365

Ser Val Val Asn Gly Val Pro Leu Ile Ala Trp Pro Leu Tyr Ala Glu
    370                 375                 380

Gln Lys Met Asn Ala Val Met Leu Thr Glu Gly Leu Lys Val Ala Leu
385                 390                 395                 400

Arg Pro Lys Ala Gly Glu Asn Gly Leu Ile Gly Arg Val Glu Ile Ala
                405                 410                 415

Asn Ala Val Lys Gly Leu Met Glu Gly Glu Gly Lys Lys Phe Arg
            420                 425                 430

Ser Thr Met Lys Asp Leu Lys Asp Ala Ala Ser Arg Ala Leu Ser Asp
        435                 440                 445

Asp Gly Ser Ser Thr Lys Ala Leu Ala Glu Leu Ala Cys Lys Trp Glu
    450                 455                 460

Asn Lys Ile Ser Ser Thr
465                 470

<210> SEQ ID NO 30
<211> LENGTH: 505
<212> TYPE: PRT
<213> ORGANISM: Medicago truncatula

<400> SEQUENCE: 30

Met Val Ser Gln Asp Pro Lys Val His Phe Val Leu Phe Pro Met Met
1               5                   10                  15

Ala Gln Gly His Met Ile Pro Met Met Asp Ile Ala Lys Ile Leu Ala
            20                  25                  30

Gln His Gln Asn Val Ile Val Thr Ile Val Thr Thr Pro Lys Asn Ala
        35                  40                  45

Ser Arg Phe Thr Ser Ile Val Ala Arg Cys Val Glu Tyr Gly Leu Asp
```

-continued

```
               50                  55                  60
Ile Gln Leu Val Gln Leu Glu Phe Pro Cys Lys Glu Ser Gly Leu Pro
 65                  70                  75                  80

Glu Gly Cys Glu Asn Leu Asp Met Leu Pro Ala Leu Gly Met Ala Ser
                 85                  90                  95

Asn Phe Leu Asn Ala Leu Lys Phe Phe Gln Gln Glu Val Glu Lys Leu
                100                 105                 110

Phe Glu Glu Phe Thr Thr Pro Ala Thr Cys Ile Ile Ser Asp Met Cys
                115                 120                 125

Leu Pro Tyr Thr Ser His Val Ala Arg Lys Phe Asn Ile Pro Arg Ile
130                 135                 140

Thr Phe Leu Gly Val Ser Cys Phe His Leu Phe Asn Met His Asn Phe
145                 150                 155                 160

His Val Asn Asn Met Ala Glu Ile Met Ala Asn Lys Glu Ser Glu Tyr
                165                 170                 175

Phe Glu Leu Pro Gly Ile Pro Asp Lys Ile Glu Met Thr Ile Ala Gln
                180                 185                 190

Thr Gly Leu Gly Gly Leu Lys Gly Glu Val Trp Lys Gln Phe Asn Asp
                195                 200                 205

Asp Leu Leu Glu Ala Glu Ile Gly Ser Tyr Gly Met Leu Val Asn Ser
210                 215                 220

Phe Glu Glu Leu Glu Pro Thr Tyr Ala Arg Asp Tyr Lys Lys Val Arg
225                 230                 235                 240

Asn Asp Lys Val Trp Cys Ile Gly Pro Val Ser Leu Ser Asn Thr Asp
                245                 250                 255

Tyr Leu Asp Lys Val Gln Arg Gly Asn Asn Asn Lys Val Ser Asn
                260                 265                 270

Asp Glu Trp Glu His Leu Lys Trp Leu Asp Ser His Lys Gln Gly Ser
                275                 280                 285

Val Ile Tyr Ala Cys Phe Gly Ser Leu Cys Asn Leu Thr Pro Pro Gln
                290                 295                 300

Leu Ile Glu Leu Gly Leu Ala Leu Glu Ala Thr Lys Arg Pro Phe Ile
305                 310                 315                 320

Trp Val Leu Arg Glu Gly Asn Gln Leu Glu Glu Leu Lys Lys Trp Leu
                325                 330                 335

Glu Glu Ser Gly Phe Glu Gly Arg Ile Asn Gly Arg Gly Leu Val Ile
                340                 345                 350

Lys Gly Trp Ala Pro Gln Leu Leu Ile Leu Ser His Leu Ala Ile Gly
                355                 360                 365

Gly Phe Leu Thr His Cys Gly Trp Asn Ser Thr Leu Glu Ala Ile Cys
370                 375                 380

Ala Gly Val Pro Met Val Thr Trp Pro Leu Phe Ala Asp Gln Phe Leu
385                 390                 395                 400

Asn Glu Ser Phe Val Val Gln Ile Leu Lys Val Gly Val Lys Ile Gly
                405                 410                 415

Val Lys Ser Pro Met Lys Trp Gly Glu Glu Asp Gly Val Leu Val
                420                 425                 430

Lys Lys Glu Asp Ile Glu Arg Gly Ile Glu Lys Leu Met Asp Glu Thr
                435                 440                 445

Ser Glu Cys Lys Glu Arg Arg Lys Arg Ile Arg Glu Leu Ala Glu Met
                450                 455                 460

Ala Lys Lys Ala Val Glu Lys Gly Gly Ser Ser His Ser Asn Ile Ser
465                 470                 475                 480
```

```
Leu Phe Ile Gln Asp Ile Met Lys Lys Asn Lys Asp Met Met Ser Ser
                485                 490                 495

Phe Ile His Gly Asn Ala Asn Ser Lys
            500                 505

<210> SEQ ID NO 31
<211> LENGTH: 479
<212> TYPE: PRT
<213> ORGANISM: Medicago truncatula

<400> SEQUENCE: 31

Met Lys Asp Thr Ile Val Leu Tyr Pro Ala Phe Gly Ser Gly His Leu
1               5                   10                  15

Met Ser Met Val Glu Leu Gly Lys Leu Ile Leu Thr His His Pro Ser
            20                  25                  30

Phe Ser Ile Lys Ile Leu Ile Leu Thr Pro Pro Asn Gln Asp Thr Asn
        35                  40                  45

Thr Ile Asn Val Ser Thr Ser Gln Tyr Ile Ser Val Ser Asn Lys
    50                  55                  60

Phe Pro Ser Ile Asn Phe His Tyr Ile Pro Ser Ile Ser Phe Thr Phe
65                  70                  75                  80

Thr Leu Pro Pro His Leu Gln Thr Leu Glu Leu Ser Pro Arg Ser Asn
                85                  90                  95

His His Val His His Ile Leu Gln Ser Ile Ala Lys Thr Ser Asn Leu
            100                 105                 110

Lys Ala Val Met Leu Asp Phe Leu Asn Tyr Ser Ala Ser Gln Val Thr
        115                 120                 125

Asn Asn Leu Glu Ile Pro Thr Tyr Phe Tyr Tyr Thr Ser Gly Ala Ser
130                 135                 140

Leu Leu Cys Leu Phe Leu Asn Phe Pro Thr Phe His Lys Asn Ala Thr
145                 150                 155                 160

Ile Pro Ile Lys Asp Tyr Asn Met His Thr Pro Ile Glu Leu Pro Gly
                165                 170                 175

Leu Pro Arg Leu Ser Lys Glu Asp Tyr Pro Asp Glu Gly Lys Asp Pro
            180                 185                 190

Ser Ser Pro Ser Tyr Gln Val Leu Leu Gln Ser Ala Lys Ser Leu Arg
        195                 200                 205

Glu Ser Asp Gly Ile Ile Val Asn Thr Phe Asp Ala Ile Glu Lys Lys
210                 215                 220

Ala Ile Lys Ala Leu Arg Asn Gly Leu Cys Val Pro Asp Gly Thr Thr
225                 230                 235                 240

Pro Leu Leu Phe Cys Ile Gly Pro Val Val Ser Thr Ser Cys Glu Glu
                245                 250                 255

Asp Lys Ser Gly Cys Leu Ser Trp Leu Asp Ser Gln Pro Gly Gln Ser
            260                 265                 270

Val Val Leu Leu Ser Phe Gly Ser Leu Gly Arg Phe Ser Lys Ala Gln
        275                 280                 285

Ile Asn Gln Ile Ala Ile Gly Leu Glu Lys Ser Glu Gln Arg Phe Leu
290                 295                 300

Trp Ile Val Arg Ser Asp Met Glu Ser Glu Glu Leu Ser Leu Asp Glu
305                 310                 315                 320

Leu Leu Pro Glu Gly Phe Leu Glu Arg Thr Lys Glu Lys Gly Met Val
                325                 330                 335

Val Arg Asn Trp Ala Pro Gln Gly Ser Ile Leu Arg His Ser Ser Val
            340                 345                 350
```

```
Gly Gly Phe Val Thr His Cys Gly Trp Asn Ser Val Leu Glu Ala Ile
            355                 360                 365

Cys Glu Gly Val Pro Met Ile Thr Trp Pro Leu Tyr Ala Glu Gln Lys
370                 375                 380

Met Asn Arg Leu Ile Leu Val Gln Glu Trp Lys Val Ala Leu Glu Leu
385                 390                 395                 400

Asn Glu Ser Lys Asp Gly Phe Val Ser Glu Asn Glu Leu Gly Glu Arg
            405                 410                 415

Val Lys Glu Leu Met Glu Ser Glu Lys Gly Lys Glu Val Arg Glu Thr
            420                 425                 430

Ile Leu Lys Met Lys Ile Ser Ala Lys Glu Ala Arg Gly Gly Gly Gly
            435                 440                 445

Ser Ser Leu Val Asp Leu Lys Lys Leu Gly Asp Ser Trp Arg Glu His
            450                 455                 460

Ala Ser Trp Thr Ser Val Ser Pro Asn Ser Pro Phe Leu Phe Ala
465                 470                 475

<210> SEQ ID NO 32
<211> LENGTH: 482
<212> TYPE: PRT
<213> ORGANISM: Medicago truncatula

<400> SEQUENCE: 32

Met Lys Asp Thr Leu Val Leu Tyr Pro Ala Leu Gly Lys Gly His Leu
1               5                   10                  15

Asn Ser Met Ile Glu Leu Gly Lys Leu Ile Leu Thr His Asn Pro Ser
            20                  25                  30

Tyr Ser Ile Thr Ile Leu Ile Leu Thr Pro Asn Thr Thr Leu Gln
            35                  40                  45

Pro Pro Gln Glu Ile Gln Lys Leu Thr Thr Thr Thr Phe Gly Cys
50                  55                  60

Glu Ser Phe Pro Ser Ile Thr Phe His His Ile Pro Pro Ile Ser Phe
65                  70                  75                  80

Pro Val Thr Leu Pro Pro His Ile Val Pro Leu Glu Val Cys Gly Arg
            85                  90                  95

Ser Asn His His Val Asn His Val Leu Gln Ser Ile Ser Lys Thr Ser
            100                 105                 110

Asn Leu Lys Gly Val Ile Leu Asp Phe Met Asn Tyr Ser Thr Asn Gln
            115                 120                 125

Ile Thr Ser Thr Leu Asp Ile Pro Thr Tyr Phe Phe Tyr Thr Ser Gly
            130                 135                 140

Ala Ser Thr Leu Ala Val Phe Leu Gln Leu Pro Thr Ile His Gln Ser
145                 150                 155                 160

Thr Thr Lys Ser Leu Lys Glu Phe His Met Tyr Pro Arg Ile Pro Gly
                165                 170                 175

Leu Pro Leu Val Pro Ile Val Asp Met Pro Asp Glu Val Lys Asp Arg
            180                 185                 190

Glu Ser Lys Ser Tyr Lys Val Phe Leu Asp Met Ala Thr Ser Met Arg
            195                 200                 205

Glu Ser Asp Gly Val Ile Ile Asn Thr Phe Asp Ala Ile Glu Gly Arg
            210                 215                 220

Ala Ala Lys Ala Leu Lys Ala Gly Leu Cys Leu Pro Glu Gly Thr Thr
225                 230                 235                 240

Pro Pro Leu Phe Cys Ile Gly Pro Met Ile Ser Pro Pro Cys Lys Gly
                245                 250                 255
```

```
Glu Asp Glu Arg Gly Ser Ser Cys Leu Ser Trp Leu Asp Ser Gln Pro
            260                 265                 270

Ser Gln Ser Val Val Leu Leu Ser Phe Gly Ser Met Gly Arg Phe Ser
        275                 280                 285

Arg Ala Gln Leu Asn Glu Ile Ala Ile Gly Leu Glu Lys Ser Glu Gln
    290                 295                 300

Arg Phe Leu Trp Val Val Arg Ser Glu Pro Asp Ser Asp Lys Leu Ser
305                 310                 315                 320

Leu Asp Glu Leu Phe Pro Gly Phe Leu Glu Arg Thr Lys Asp Lys
                325                 330                 335

Gly Met Val Val Arg Asn Trp Ala Pro Gln Val Ala Ile Leu Ser His
            340                 345                 350

Asn Ser Val Gly Gly Phe Val Thr His Cys Gly Trp Asn Ser Val Leu
        355                 360                 365

Glu Ala Ile Cys Glu Gly Val Pro Met Ile Ala Trp Pro Leu Phe Ala
    370                 375                 380

Glu Gln Arg Leu Asn Arg Leu Val Leu Val Asp Glu Met Lys Val Ala
385                 390                 395                 400

Leu Lys Val Asn Gln Ser Glu Asn Arg Phe Val Ser Gly Thr Glu Leu
                405                 410                 415

Gly Glu Arg Val Lys Glu Leu Met Glu Ser Asp Arg Gly Lys Asp Ile
            420                 425                 430

Lys Glu Arg Ile Leu Lys Met Lys Ile Ser Ala Lys Glu Ala Arg Gly
        435                 440                 445

Gly Gly Gly Ser Ser Leu Val Asp Leu Lys Lys Leu Gly Asp Ser Trp
    450                 455                 460

Arg Glu His Ala Ser Trp Asn Ser Leu Ser Pro Asn Ser Pro Phe Leu
465                 470                 475                 480

Leu Arg

<210> SEQ ID NO 33
<211> LENGTH: 465
<212> TYPE: PRT
<213> ORGANISM: Medicago truncatula

<400> SEQUENCE: 33

Met Ser Met Ser Asp Ile Asn Lys Asn Ser Glu Leu Ile Phe Ile Pro
1               5                   10                  15

Ala Pro Gly Ile Gly His Leu Ala Ser Ala Leu Glu Phe Ala Lys Leu
            20                  25                  30

Leu Thr Asn His Asp Lys Asn Leu Tyr Ile Thr Val Phe Cys Ile Lys
        35                  40                  45

Phe Pro Gly Met Pro Phe Ala Asp Ser Tyr Ile Lys Ser Val Leu Ala
    50                  55                  60

Ser Gln Pro Gln Ile Gln Leu Ile Asp Leu Pro Glu Val Glu Pro Pro
65                  70                  75                  80

Pro Gln Glu Leu Leu Lys Ser Pro Glu Phe Tyr Ile Leu Thr Phe Leu
                85                  90                  95

Glu Ser Leu Ile Pro His Val Lys Ala Thr Ile Lys Thr Ile Leu Ser
            100                 105                 110

Asn Lys Val Val Gly Leu Val Leu Asp Phe Phe Cys Val Ser Met Ile
        115                 120                 125

Asp Val Gly Asn Glu Phe Gly Ile Pro Ser Tyr Leu Phe Leu Thr Ser
    130                 135                 140

Asn Val Gly Phe Leu Ser Leu Met Leu Ser Leu Lys Asn Arg Gln Ile
```

```
                145                 150                 155                 160
Glu Glu Val Phe Asp Asp Ser Asp Arg Asp His Gln Leu Leu Asn Ile
                165                 170                 175
Pro Gly Ile Ser Asn Gln Val Pro Ser Asn Val Leu Pro Asp Ala Cys
            180                 185                 190
Phe Asn Lys Asp Gly Gly Tyr Ile Ala Tyr Tyr Lys Leu Ala Glu Arg
        195                 200                 205
Phe Arg Asp Thr Lys Gly Ile Ile Val Asn Thr Phe Ser Asp Leu Glu
    210                 215                 220
Gln Ser Ser Ile Asp Ala Leu Tyr Asp His Asp Glu Lys Ile Pro Pro
225                 230                 235                 240
Ile Tyr Ala Val Gly Pro Leu Leu Asp Leu Lys Gly Gln Pro Asn Pro
                245                 250                 255
Lys Leu Asp Gln Ala Gln His Asp Leu Ile Leu Lys Trp Leu Asp Glu
            260                 265                 270
Gln Pro Asp Lys Ser Val Val Phe Leu Cys Phe Gly Ser Met Gly Val
        275                 280                 285
Ser Phe Gly Pro Ser Gln Ile Arg Glu Ile Ala Leu Gly Leu Lys His
    290                 295                 300
Ser Gly Val Arg Phe Leu Trp Ser Asn Ser Ala Glu Lys Lys Val Phe
305                 310                 315                 320
Pro Glu Gly Phe Leu Glu Trp Met Glu Leu Gly Lys Gly Met Ile
                325                 330                 335
Cys Gly Trp Ala Pro Gln Val Glu Val Leu Ala His Lys Ala Ile Gly
            340                 345                 350
Gly Phe Val Ser His Cys Gly Trp Asn Ser Ile Leu Glu Ser Met Trp
        355                 360                 365
Phe Gly Val Pro Ile Leu Thr Trp Pro Ile Tyr Ala Glu Gln Gln Leu
    370                 375                 380
Asn Ala Phe Arg Leu Val Lys Glu Trp Gly Val Gly Leu Gly Leu Arg
385                 390                 395                 400
Val Asp Tyr Arg Lys Gly Ser Asp Val Val Ala Ala Glu Glu Ile Glu
                405                 410                 415
Lys Gly Leu Lys Asp Leu Met Asp Lys Asp Ser Ile Val His Lys Lys
            420                 425                 430
Val Gln Glu Met Lys Glu Met Ser Arg Asn Ala Val Val Asp Gly Gly
        435                 440                 445
Ser Ser Leu Ile Ser Val Gly Lys Leu Ile Asp Asp Ile Thr Gly Ser
    450                 455                 460
Asn
465

<210> SEQ ID NO 34
<211> LENGTH: 459
<212> TYPE: PRT
<213> ORGANISM: Medicago truncatula

<400> SEQUENCE: 34

Met Ala Ser Glu Ala Ser Ile His Ile Leu Val Ser Phe Pro Ala
1               5                   10                  15

Gln Gly His Ile Asn Pro Leu Leu Arg Leu Gly Lys Cys Leu Ala Ala
                20                  25                  30

Lys Gly Ala Ser Val Ile Phe Ile Thr Thr Glu Lys Gly Gly Lys Asn
            35                  40                  45

Met Arg Ile Thr Asn Lys Leu Ala Thr Pro Ile Gly Asp Gly Ser Leu
```

```
            50                  55                  60
Met Phe Gln Phe Phe Asp Asp Gly Leu Pro Asp Tyr Ala His Pro Leu
 65                  70                  75                  80

Asp His His Lys Lys Leu Glu Leu Val Gly Arg Gln Phe Ile Ser Gln
                 85                  90                  95

Met Ile Lys Asn His Ala Asp Ser Asn Lys Pro Ile Ser Cys Ile Ile
                100                 105                 110

Asn Asn Pro Phe Pro Trp Val Ser Asp Ile Ala Phe Glu His Asn
                115                 120                 125

Ile Pro Ser Ala Leu Leu Trp Thr Asn Ser Ser Ala Val Phe Thr Ile
130                 135                 140

Cys Tyr Asp Tyr Val His Lys Leu Leu Pro Phe Pro Ser Asn Glu Glu
145                 150                 155                 160

Pro Tyr Ile Asp Val Gln Leu Asn Ser Ser Ile Val Leu Lys Tyr Asn
                165                 170                 175

Glu Ile Pro Asp Phe Ile His Pro Phe Cys Arg Tyr Pro Ile Leu Gly
                180                 185                 190

Thr Leu Thr Thr Ala Gln Ile Lys Asp Met Ser Lys Val Phe Cys Val
                195                 200                 205

Leu Val Asp Thr Phe Glu Glu Leu Glu His Asp Phe Ile Asp Tyr Ile
210                 215                 220

Ser Glu Lys Ser Ile Ala Ile Arg Pro Val Gly Pro Leu Phe Lys Asn
225                 230                 235                 240

Pro Lys Ala Asn Gly Ala Ser Asn Asn Ile Leu Gly Asp Phe Thr Lys
                245                 250                 255

Ser Asn Asp Asp Cys Asn Ile Ile Glu Trp Leu Asn Thr Lys Pro Lys
                260                 265                 270

Gly Ser Val Val Tyr Ile Ser Phe Gly Thr Val Val Tyr Leu Pro Gln
                275                 280                 285

Glu Leu Val Tyr Glu Ile Ala Tyr Gly Leu Leu Asp Ser Gln Val Thr
                290                 295                 300

Phe Leu Trp Ala Lys Lys Gln His Asp Asp Leu Pro Tyr Gly Phe Leu
305                 310                 315                 320

Glu Glu Thr Ser Gly Arg Gly Lys Val Val Asn Trp Ser Pro Gln Glu
                325                 330                 335

Gln Val Leu Ala His Pro Ser Val Ala Cys Phe Ile Thr His Cys Gly
                340                 345                 350

Trp Asn Ser Ser Met Glu Ala Leu Thr Leu Gly Val Pro Met Leu Thr
                355                 360                 365

Phe Pro Thr Phe Gly Asp Gln Leu Thr Asn Ala Lys Phe Leu Val Asp
                370                 375                 380

Val Tyr Gly Val Gly Ile Arg Leu Ala Arg Gly Glu Arg Lys Leu Val
385                 390                 395                 400

Arg Arg Asp Asp Leu Lys Lys Cys Leu Leu Glu Val Thr Thr Gly Glu
                405                 410                 415

Lys Ala Glu Thr Leu Lys Lys Asn Ala Thr Lys Leu Lys Lys Ala Ala
                420                 425                 430

Glu Glu Ala Val Ala Val Gly Gly Ser Ser Asp Arg His Leu Asp Ala
                435                 440                 445

Phe Met Glu Asp Ile Lys Lys His Lys Arg Cys
                450                 455

<210> SEQ ID NO 35
<211> LENGTH: 482
```

```
<212> TYPE: PRT
<213> ORGANISM: Medicago truncatula

<400> SEQUENCE: 35

Met Gly Asn Phe Ala Asn Arg Lys Pro His Val Val Met Ile Pro Tyr
1               5                   10                  15

Pro Val Gln Gly His Ile Asn Pro Leu Phe Lys Leu Ala Lys Leu Leu
            20                  25                  30

His Leu Arg Gly Phe His Ile Thr Phe Val Asn Thr Glu Tyr Asn His
        35                  40                  45

Lys Arg Leu Leu Lys Ser Arg Gly Pro Lys Ala Phe Asp Gly Phe Thr
    50                  55                  60

Asp Phe Asn Phe Glu Ser Ile Pro Asp Gly Leu Thr Pro Met Glu Gly
65                  70                  75                  80

Asp Gly Asp Val Ser Gln Asp Val Pro Thr Leu Cys Gln Ser Val Arg
                85                  90                  95

Lys Asn Phe Leu Lys Pro Tyr Cys Glu Leu Leu Thr Arg Leu Asn His
            100                 105                 110

Ser Thr Asn Val Pro Pro Val Thr Cys Leu Val Ser Asp Cys Cys Met
        115                 120                 125

Ser Phe Thr Ile Gln Ala Ala Glu Glu Phe Glu Leu Pro Asn Val Leu
    130                 135                 140

Tyr Phe Ser Ser Ser Ala Cys Ser Leu Leu Asn Val Met His Phe Arg
145                 150                 155                 160

Ser Phe Val Glu Arg Gly Ile Ile Pro Phe Lys Asp Glu Ser Tyr Leu
                165                 170                 175

Thr Asn Gly Cys Leu Glu Thr Lys Val Asp Trp Ile Pro Gly Leu Lys
            180                 185                 190

Asn Phe Arg Leu Lys Asp Ile Val Asp Phe Ile Arg Thr Thr Asn Pro
        195                 200                 205

Asn Asp Ile Met Leu Glu Phe Phe Ile Glu Val Ala Asp Arg Val Asn
    210                 215                 220

Lys Asp Thr Thr Ile Leu Leu Asn Thr Phe Asn Glu Leu Glu Ser Asp
225                 230                 235                 240

Val Ile Asn Ala Leu Ser Ser Thr Ile Pro Ser Ile Tyr Pro Ile Gly
                245                 250                 255

Pro Leu Pro Ser Leu Leu Lys Gln Thr Pro Gln Ile His Gln Leu Asp
            260                 265                 270

Ser Leu Asp Ser Asn Leu Trp Lys Glu Asp Thr Glu Cys Leu Asp Trp
        275                 280                 285

Leu Glu Ser Lys Glu Pro Gly Ser Val Val Tyr Val Asn Phe Gly Ser
    290                 295                 300

Ile Thr Val Met Thr Pro Glu Gln Leu Leu Glu Phe Ala Trp Gly Leu
305                 310                 315                 320

Ala Asn Cys Lys Lys Ser Phe Leu Trp Ile Ile Arg Pro Asp Leu Val
                325                 330                 335

Ile Gly Gly Ser Val Ile Phe Ser Ser Glu Phe Thr Asn Glu Ile Ala
            340                 345                 350

Asp Arg Gly Leu Ile Ala Ser Trp Cys Pro Gln Asp Lys Val Leu Asn
        355                 360                 365

His Pro Ser Ile Gly Gly Phe Leu Thr His Cys Gly Trp Asn Ser Thr
    370                 375                 380

Thr Glu Ser Ile Cys Ala Gly Val Pro Met Leu Cys Trp Pro Phe Phe
385                 390                 395                 400
```

```
Ala Asp Gln Pro Thr Asp Cys Arg Phe Ile Cys Asn Glu Trp Glu Ile
                405                 410                 415

Gly Met Glu Ile Asp Thr Asn Val Lys Arg Glu Glu Leu Ala Lys Leu
            420                 425                 430

Ile Asn Glu Val Ile Ala Gly Asp Lys Gly Lys Met Lys Gln Lys
        435                 440                 445

Ala Met Glu Leu Lys Lys Ala Glu Glu Asn Thr Arg Pro Gly Gly
    450                 455                 460

Cys Ser Tyr Met Asn Leu Asn Lys Val Ile Lys Asp Val Leu Leu Lys
465                 470                 475                 480

Gln Asn
```

<210> SEQ ID NO 36
<211> LENGTH: 454
<212> TYPE: PRT
<213> ORGANISM: Medicago truncatula

<400> SEQUENCE: 36

```
Met Ser Thr Phe Lys Asn Glu Met Asn Gly Asn Asn Leu Leu His Val
1               5                   10                  15

Ala Val Leu Ala Phe Pro Phe Gly Thr His Ala Ala Pro Leu Leu Ser
            20                  25                  30

Leu Val Lys Lys Ile Ala Thr Glu Ala Pro Lys Val Thr Phe Ser Phe
        35                  40                  45

Phe Cys Thr Thr Thr Thr Asn Asp Thr Leu Phe Ser Arg Ser Asn Glu
    50                  55                  60

Phe Leu Pro Asn Ile Lys Tyr Tyr Asn Val His Asp Gly Leu Pro Lys
65                  70                  75                  80

Gly Tyr Val Ser Ser Gly Asn Pro Arg Glu Pro Ile Phe Leu Phe Ile
                85                  90                  95

Lys Ala Met Gln Glu Asn Phe Lys His Val Ile Asp Glu Ala Val Ala
            100                 105                 110

Glu Thr Gly Lys Asn Ile Thr Cys Leu Val Thr Asp Ala Phe Phe Trp
        115                 120                 125

Phe Gly Ala Asp Leu Ala Glu Glu Met His Ala Lys Trp Val Pro Leu
    130                 135                 140

Trp Thr Ala Gly Pro His Ser Leu Leu Thr His Val Tyr Thr Asp Leu
145                 150                 155                 160

Ile Arg Glu Lys Thr Gly Ser Lys Glu Val His Asp Val Lys Ser Ile
                165                 170                 175

Asp Val Leu Pro Gly Phe Pro Glu Leu Lys Ala Ser Asp Leu Pro Glu
            180                 185                 190

Gly Val Ile Lys Asp Ile Asp Val Pro Phe Ala Thr Met Leu His Lys
        195                 200                 205

Met Gly Leu Glu Leu Pro Arg Ala Asn Ala Val Ala Ile Asn Ser Phe
    210                 215                 220

Ala Thr Ile His Pro Leu Ile Glu Asn Glu Leu Asn Ser Lys Phe Lys
225                 230                 235                 240

Leu Leu Leu Asn Val Gly Pro Phe Asn Leu Thr Thr Pro Gln Arg Lys
                245                 250                 255

Val Ser Asp Glu His Gly Cys Leu Glu Trp Leu Asp Gln His Glu Asn
            260                 265                 270

Ser Ser Val Val Tyr Ile Ser Phe Gly Ser Val Thr Pro Pro Pro
        275                 280                 285

His Glu Leu Thr Ala Leu Ala Glu Ser Leu Glu Glu Cys Gly Phe Pro
```

```
            290                 295                 300
Phe Ile Trp Ser Phe Arg Gly Asp Pro Lys Glu Lys Leu Pro Lys Gly
305                 310                 315                 320

Phe Leu Glu Arg Thr Lys Thr Lys Gly Lys Ile Val Ala Trp Ala Pro
            325                 330                 335

Gln Val Glu Ile Leu Lys His Ser Ser Val Gly Val Phe Leu Thr His
                340                 345                 350

Ser Gly Trp Asn Ser Val Leu Glu Cys Ile Val Gly Gly Val Pro Met
            355                 360                 365

Ile Ser Arg Pro Phe Phe Gly Asp Gln Gly Leu Asn Thr Ile Leu Thr
370                 375                 380

Glu Ser Val Leu Glu Ile Gly Val Gly Val Asp Asn Gly Val Leu Thr
385                 390                 395                 400

Lys Glu Ser Ile Lys Lys Ala Leu Glu Leu Thr Met Ser Ser Glu Lys
                405                 410                 415

Gly Gly Ile Met Arg Gln Lys Ile Val Lys Leu Lys Glu Ser Ala Phe
            420                 425                 430

Lys Ala Val Glu Gln Asn Gly Thr Ser Ala Met Asp Phe Thr Thr Leu
            435                 440                 445

Ile Gln Ile Val Thr Ser
450

<210> SEQ ID NO 37
<211> LENGTH: 502
<212> TYPE: PRT
<213> ORGANISM: Medicago truncatula

<400> SEQUENCE: 37

Met Glu Ser Phe Gly Val Lys Val Glu Glu Thr Met Leu Lys Ala
1               5                   10                  15

Val Phe Leu Pro Phe Ile Ser Lys Ser His Leu Ile Phe Val Val Asp
                20                  25                  30

Ile Ala Arg Leu Phe Ala Met His Asn Val Asp Val Thr Ile Ile Thr
            35                  40                  45

Thr Pro Ala Asn Ala Ala Ile Phe Gln Thr Ser Ile Asp His Asp Ser
        50                  55                  60

Ser Arg Gly Arg Ser Ile Arg Thr His Ile Val Lys Phe Pro Gln Val
65                  70                  75                  80

Pro Gly Leu Pro Gln Gly Met Glu Ser Phe Asn Ala Asp Thr Pro Lys
                85                  90                  95

Asp Ile Ile Ser Lys Ile Tyr Gln Gly Leu Ala Ile Leu Gln Glu Gln
            100                 105                 110

Phe Thr Gln Leu Phe Arg Asp Met Lys Pro Asp Phe Ile Val Thr Asp
        115                 120                 125

Met Phe Tyr Pro Trp Ser Val Asp Val Ala Asp Glu Leu Gly Ile Pro
130                 135                 140

Arg Leu Ile Cys Ile Gly Gly Ser Tyr Phe Ala His Ser Ala Met Asn
145                 150                 155                 160

Ser Ile Glu Gln Phe Glu Pro His Ala Lys Val Lys Ser Asn Ser Val
                165                 170                 175

Ser Phe Leu Leu Pro Gly Leu Pro His Asn Val Glu Met Thr Arg Leu
            180                 185                 190

Gln Leu Pro Asp Trp Leu Arg Ala Pro Asn Gly Tyr Thr Tyr Leu Met
        195                 200                 205

Lys Met Ile Lys Asp Ser Glu Lys Lys Ser Tyr Gly Ser Leu Phe Asp
```

```
            210                 215                 220
Ser Tyr Tyr Glu Ile Glu Gly Thr Tyr Glu Asp Tyr Lys Ile Ala
225                 230                 235                 240

Met Gly Ser Lys Ser Trp Ser Val Gly Pro Val Ser Leu Trp Met Asn
                245                 250                 255

Lys Asp Asp Ser Asp Lys Ala Gly Arg Gly His Gly Lys Glu Glu Asp
                260                 265                 270

Glu Glu Glu Gly Val Leu Lys Trp Leu Asp Ser Lys Lys Tyr Asp Ser
                275                 280                 285

Val Leu Tyr Val Ser Phe Gly Ser Met Asn Lys Phe Pro Thr Pro Gln
            290                 295                 300

Leu Val Glu Ile Ala His Ala Leu Glu Asp Ser Gly His Asp Phe Ile
305                 310                 315                 320

Trp Val Val Arg Lys Ile Glu Asp Ala Glu Asp Gly Asp Asp Gly Phe
                325                 330                 335

Leu Ser Glu Phe Glu Lys Arg Met Lys Glu Arg Asn Lys Gly Tyr Leu
                340                 345                 350

Ile Trp Gly Trp Ala Pro Gln Leu Leu Ile Leu Glu His Gly Ala Val
            355                 360                 365

Gly Ala Val Val Thr His Cys Gly Trp Asn Thr Ile Met Glu Ser Val
370                 375                 380

Asn Ala Gly Leu Pro Leu Ala Thr Trp Pro Leu Phe Ala Glu Gln Phe
385                 390                 395                 400

Phe Asn Glu Arg Leu Leu Val Asp Val Leu Lys Ile Gly Val Ala Val
                405                 410                 415

Gly Ala Lys Glu Trp Arg Asn Trp Asn Glu Phe Gly Asp Asp Val Val
                420                 425                 430

Lys Arg Glu Asp Ile Gly Lys Ala Ile Gly Leu Leu Met Gly Gly Gly
                435                 440                 445

Glu Glu Cys Leu Glu Met Arg Lys Arg Val Lys Ala Leu Ser Gly Ala
            450                 455                 460

Ala Lys Lys Ala Ile Glu Val Gly Gly Ser Ser Tyr Thr Lys Leu Lys
465                 470                 475                 480

Glu Leu Ile Glu Glu Leu Lys Ser Phe Lys Leu Glu Lys Ile Asn Lys
                485                 490                 495

Lys Leu Val Ser Val Thr
            500

<210> SEQ ID NO 38
<211> LENGTH: 243
<212> TYPE: PRT
<213> ORGANISM: Medicago truncatula

<400> SEQUENCE: 38

Met Glu Asn Thr Gly Gly Val Arg Lys Gly Ala Trp Thr Tyr Lys Glu
1               5                   10                  15

Asp Glu Leu Leu Lys Ala Cys Ile Asn Thr Tyr Gly Glu Gly Lys Trp
                20                  25                  30

Asn Leu Val Pro Gln Arg Ser Gly Leu Asn Arg Cys Arg Lys Ser Cys
            35                  40                  45

Arg Leu Arg Trp Leu Asn Tyr Leu Ser Pro Asn Ile Asn Arg Gly Arg
        50                  55                  60

Phe Ser Glu Asp Glu Glu Asp Leu Ile Leu Arg Leu His Lys Leu Leu
65                  70                  75                  80

Gly Asn Arg Trp Ser Leu Ile Ala Gly Arg Leu Pro Gly Arg Thr Ala
```

```
                    85                  90                  95
Asn Asp Val Lys Asn Tyr Trp His Thr Asn Leu Ala Lys Lys Val Val
                100                 105                 110

Ser Glu Lys Glu Glu Lys Glu Asn Asp Lys Pro Lys Glu Thr Met
        115                 120                 125

Lys Ala His Glu Val Ile Lys Pro Arg Pro Ile Thr Leu Ser Ser His
        130                 135                 140

Ser Asn Trp Leu Lys Gly Lys Asn Ser Ile Pro Arg Asp Leu Asp Tyr
145                 150                 155                 160

Ser Glu Asn Met Ala Ser Asn Gln Ile Gly Arg Glu Cys Ala Ser Thr
                165                 170                 175

Ser Lys Pro Asp Leu Gly Asn Ala Pro Ile Pro Cys Glu Met Trp Cys
                180                 185                 190

Asp Ser Leu Trp Asn Leu Gly Glu His Val Asp Ser Glu Lys Ile Gly
                195                 200                 205

Ser Cys Ser Ser Leu Gln Glu Glu Leu Met Glu Phe Pro Asn Val Asp
        210                 215                 220

Asp Asp Ser Phe Trp Asp Phe Asn Leu Cys Asp Leu Asn Ser Leu Trp
225                 230                 235                 240

Asp Leu Pro

<210> SEQ ID NO 39
<211> LENGTH: 32
<212> TYPE: DNA
<213> ORGANISM: Artificial sequence
<220> FEATURE:
<223> OTHER INFORMATION: Synthetic primer

<400> SEQUENCE: 39
gggcccatgg accagactct tacacacacc ga                              32

<210> SEQ ID NO 40
<211> LENGTH: 35
<212> TYPE: DNA
<213> ORGANISM: Artificial sequence
<220> FEATURE:
<223> OTHER INFORMATION: Synthetic primer

<400> SEQUENCE: 40
cccagatcta gaatgagacc aaagactcat atact                           35

<210> SEQ ID NO 41
<211> LENGTH: 37
<212> TYPE: DNA
<213> ORGANISM: Artificial sequence
<220> FEATURE:
<223> OTHER INFORMATION: Synthetic primer

<400> SEQUENCE: 41
ggggatatca tgagctccac agagacatac gagccgt                         37

<210> SEQ ID NO 42
<211> LENGTH: 44
<212> TYPE: DNA
<213> ORGANISM: Artificial sequence
<220> FEATURE:
<223> OTHER INFORMATION: Synthetic primer

<400> SEQUENCE: 42 cccccctcgag actagtaaca cctgcgttag ccatctcttg attc                44
```

```
<210> SEQ ID NO 43
<211> LENGTH: 33
<212> TYPE: DNA
<213> ORGANISM: Artificial sequence
<220> FEATURE:
<223> OTHER INFORMATION: Synthetic primer

<400> SEQUENCE: 43
caccatggtt agtcagaaag agaccgtgtg tgt                              33

<210> SEQ ID NO 44
<211> LENGTH: 39
<212> TYPE: DNA
<213> ORGANISM: Artificial sequence
<220> FEATURE:
<223> OTHER INFORMATION: Synthetic primer

<400> SEQUENCE: 44
cctctagact aggcacacat ctgttgtgct agcatggga                        39

<210> SEQ ID NO 45
<211> LENGTH: 33
<212> TYPE: DNA
<213> ORGANISM: Artificial sequence
<220> FEATURE:
<223> OTHER INFORMATION: Synthetic primer

<400> SEQUENCE: 45
caccatggtt gcggttgaaa gagttgagag ttt                              33

<210> SEQ ID NO 46
<211> LENGTH: 34
<212> TYPE: DNA
<213> ORGANISM: Artificial sequence
<220> FEATURE:
<223> OTHER INFORMATION: Synthetic primer

<400> SEQUENCE: 46
actagttaat cattttctc ggataccaat tcct                              34

<210> SEQ ID NO 47
<211> LENGTH: 33
<212> TYPE: DNA
<213> ORGANISM: Artificial sequence
<220> FEATURE:
<223> OTHER INFORMATION: Synthetic primer

<400> SEQUENCE: 47
caccatggtt gtgaaactat atggacaggt aac                              33

<210> SEQ ID NO 48
<211> LENGTH: 36
<212> TYPE: DNA
<213> ORGANISM: Artificial Sequence
<220> FEATURE:
<223> OTHER INFORMATION: Synthetic primer

<400> SEQUENCE: 48
gccactagtc agtgaccagc cagcaccata agcttc                           36

<210> SEQ ID NO 49
<211> LENGTH: 35
<212> TYPE: DNA
<213> ORGANISM: Artificial sequence
<220> FEATURE:
<223> OTHER INFORMATION: Synthetic primer

<400> SEQUENCE: 49
```

```
caccatggtg atggctggtg cttcttcttt ggatg                                    35

<210> SEQ ID NO 50
<211> LENGTH: 34
<212> TYPE: DNA
<213> ORGANISM: Artificial sequence
<220> FEATURE:
<223> OTHER INFORMATION: Synthetic primer

<400> SEQUENCE: 50
ccactagtta gagaggaacg ctgtgcaaga cgac                                     34

<210> SEQ ID NO 51
<211> LENGTH: 32
<212> TYPE: DNA
<213> ORGANISM: Artificial sequence
<220> FEATURE:
<223> OTHER INFORMATION: Synthetic primer

<400> SEQUENCE: 51
ggatccatgg agggttcgtc caaagggctg cg                                       32

<210> SEQ ID NO 52
<211> LENGTH: 33
<212> TYPE: DNA
<213> ORGANISM: Artificial sequence
<220> FEATURE:
<223> OTHER INFORMATION: Synthetic primer

<400> SEQUENCE: 52
tctagactcg agatcaaatt tcacagtctc tcc                                      33

<210> SEQ ID NO 53
<211> LENGTH: 24
<212> TYPE: DNA
<213> ORGANISM: Artificial sequence
<220> FEATURE:
<223> OTHER INFORMATION: Synthetic primer

<400> SEQUENCE: 53
gatatggaaa agatctggca tcac                                                24

<210> SEQ ID NO 54
<211> LENGTH: 24
<212> TYPE: DNA
<213> ORGANISM: Artificial sequence
<220> FEATURE:
<223> OTHER INFORMATION: Synthetic primer

<400> SEQUENCE: 54
tcatactcgg ccttggagat ccac                                                24

<210> SEQ ID NO 55
<211> LENGTH: 35
<212> TYPE: DNA
<213> ORGANISM: Artificial sequence
<220> FEATURE:
<223> OTHER INFORMATION: Synthetic primer

<400> SEQUENCE: 55
ggggccatgg gaaagagagc aactactagt gtgag                                    35

<210> SEQ ID NO 56
<211> LENGTH: 40
<212> TYPE: DNA
<213> ORGANISM: Artificial sequence
```

<220> FEATURE:
<223> OTHER INFORMATION: Synthetic primer

<400> SEQUENCE: 56 cccectcgag tctagaggct caacaagtga agtctcggag                    40

<210> SEQ ID NO 57
<211> LENGTH: 33
<212> TYPE: DNA
<213> ORGANISM: Artificial sequence
<220> FEATURE:
<223> OTHER INFORMATION: Synthetic primer

<400> SEQUENCE: 57
caccatggag tcaccaccac tatacgagat atc                           33

<210> SEQ ID NO 58
<211> LENGTH: 29
<212> TYPE: DNA
<213> ORGANISM: Artificial sequence
<220> FEATURE:
<223> OTHER INFORMATION: Synthetic primer

<400> SEQUENCE: 58
ctcgagcttc agtcatcgca atccactct                                29

<210> SEQ ID NO 59
<211> LENGTH: 39
<212> TYPE: DNA
<213> ORGANISM: Artificial sequence
<220> FEATURE:
<223> OTHER INFORMATION: Synthetic primer

<400> SEQUENCE: 59
gggggatcca tggatgaatc aagtattatt ccggcagag                     39

<210> SEQ ID NO 60
<211> LENGTH: 43
<212> TYPE: DNA
<213> ORGANISM: Artificial sequence
<220> FEATURE:
<223> OTHER INFORMATION: Synthetic primer

<400> SEQUENCE: 60
cccctcgaga ctagttagat tagtatcatg tattatgact tgg                43

<210> SEQ ID NO 61
<211> LENGTH: 29
<212> TYPE: DNA
<213> ORGANISM: Artificial sequence
<220> FEATURE:
<223> OTHER INFORMATION: Synthetic primer

<400> SEQUENCE: 61
caccatgggt agagggaaga tagagataa                                29

<210> SEQ ID NO 62
<211> LENGTH: 34
<212> TYPE: DNA
<213> ORGANISM: Artificial sequence
<220> FEATURE:
<223> OTHER INFORMATION: Synthetic primer

<400> SEQUENCE: 62
ctcgagaatt gtattaatca ttctgggccg ttgg                          34

```
<210> SEQ ID NO 63
<211> LENGTH: 33
<212> TYPE: DNA
<213> ORGANISM: Artificial sequence
<220> FEATURE:
<223> OTHER INFORMATION: Synthetic primer

<400> SEQUENCE: 63
caccatggat aattcagctc cagattcgtt atc                              33

<210> SEQ ID NO 64
<211> LENGTH: 38
<212> TYPE: DNA
<213> ORGANISM: Artificial sequence
<220> FEATURE:
<223> OTHER INFORMATION: Synthetic primer

<400> SEQUENCE: 64
gtctagatca aactctaagg agctgcattt tgttagca                         38

<210> SEQ ID NO 65
<211> LENGTH: 33
<212> TYPE: DNA
<213> ORGANISM: Artificial sequence
<220> FEATURE:
<223> OTHER INFORMATION: Synthetic primer

<400> SEQUENCE: 65
caccatgtct tgtgatgatg attcagatag cag                              33

<210> SEQ ID NO 66
<211> LENGTH: 37
<212> TYPE: DNA
<213> ORGANISM: Artificial sequence
<220> FEATURE:
<223> OTHER INFORMATION: Synthetic primer

<400> SEQUENCE: 66
tctagatcaa attgtttgct tagaaagttg tggggag                          37
```